United States Patent
Bouillot et al.

(10) Patent No.: US 9,051,281 B2
(45) Date of Patent: Jun. 9, 2015

(54) COMPOUNDS

(71) Applicant: GlaxoSmithKline LLC, Philadelphia, PA (US)

(72) Inventors: Anne Marie Jeanne Bouillot, Les Ulis (FR); Alain Laroze, Les Ulis (FR); Lionel Trottet, Les Ulis (FR)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 0 days.

(21) Appl. No.: 13/923,420

(22) Filed: Jun. 21, 2013

(65) Prior Publication Data

US 2013/0281499 A1   Oct. 24, 2013

Related U.S. Application Data

(62) Division of application No. 12/741,637, filed as application No. PCT/EP2008/065104 on Nov. 7, 2008, now Pat. No. 8,486,977.

(30) Foreign Application Priority Data

Nov. 9, 2007   (GB) .................................. 0722077.5

(51) Int. Cl.
  *C07D 249/04*   (2006.01)
  *A61K 31/4192*   (2006.01)
  *C07D 413/12*   (2006.01)

(52) U.S. Cl.
  CPC ............ *C07D 249/04* (2013.01); *C07D 413/12* (2013.01)

(58) Field of Classification Search
  None
  See application file for complete search history.

(56) References Cited

U.S. PATENT DOCUMENTS

| | | | |
|---|---|---|---|
| 4,460,372 A | 7/1984 | Campbell et al. | |
| 4,573,996 A | 3/1986 | Kwiatek et al. | |
| 4,624,665 A | 11/1986 | Nuwayser | |
| 4,722,941 A | 2/1988 | Eckert et al. | |
| 5,223,261 A | 6/1993 | Nelson et al. | |
| 7,320,994 B2 | 1/2008 | Amegadzie et al. | |
| 8,207,204 B2 | 6/2012 | Bouillot et al. | |
| 8,486,977 B2 * | 7/2013 | Bouillot et al. ............... | 514/359 |
| 2005/0239786 A1 | 10/2005 | Amegadzie et al. | |
| 2006/0160794 A1 | 7/2006 | Amegadzie et al. | |
| 2006/0205713 A1 | 9/2006 | Gschwend et al. | |
| 2007/0087363 A1 | 4/2007 | Bartel et al. | |
| 2010/0022486 A1 | 1/2010 | Bouillot et al. | |
| 2010/0041590 A1 | 2/2010 | Bouillot | |
| 2010/0048617 A1 | 2/2010 | Daugan | |
| 2010/0120669 A1 | 5/2010 | Bouillot et al. | |
| 2010/0297097 A1 | 11/2010 | Bouillot et al. | |
| 2012/0225878 A1 | 9/2012 | Bouillot et al. | |

FOREIGN PATENT DOCUMENTS

| | | |
|---|---|---|
| WO | WO 01/62954 A2 | 8/2001 |
| WO | WO 02/26944 A2 | 4/2002 |
| WO | WO 2005/000821 A1 | 1/2005 |
| WO | WO 2005/011657 A | 2/2005 |
| WO | WO 2007/046867 A2 | 4/2007 |
| WO | WO 2007/046868 A2 | 4/2007 |
| WO | WO 2008/073461 A | 6/2008 |
| WO | WO 2008/138917 A | 11/2008 |
| WO | WO 2009/010560 A1 | 1/2009 |
| WO | WO 2009/016216 A1 | 2/2009 |
| WO | WO 2009/056556 A1 | 5/2009 |
| WO | WO 2009/150196 A1 | 12/2009 |

OTHER PUBLICATIONS

Hörig et al., J. Translational Med. 2:44 (2004).*
Paton, et al., Am. J. Physiol. Endocrinol. Metab., 297: E28-E37 (2009).*
Patani, et al. Chem. Rev., 98(8): 3147-3176 (1996).
Jeffcoat, et al. S. Numa (Ed). *Fatty Acid Metabolism and Its Regulation* Chapter 4, pp. 85-112 (1984).
Calderone, et al. Eur. J. Med. Chem. 43(11): 2618-2626 (Mar. 7, 2008).
Database Registry [Online]. Chemical Abstracts Services, Columbus, Ohio, USA; Oct. 10, 2007. Registry No. 950075-10-2.
Database Registry. Chemical Abstracts Services, Columbus, Ohio, USA; Oct. 10, 2007. Registry No. 949879-07-6.
Database Registry. Chemical Abstracts Services, Columbus, Ohio, USA; Apr. 23, 2007. Registry No. 931967-53-2.
de Antueno, et al. Lipids, 28(4): 285-290 (1993).
Miyazaki, et al. J. Nutrition, 131(9): 2260-2268 (2001).
Harrison, et al. J. Invest. Dermatol., 127(6): 1309-1317 (2007).
Morgan-Lappe, et al. Cancer Res., 67(9): 4390-4398 (2007).
Berge, et al. J. Pharin. Sci., 66: 1-19 (1977).
Fleishner, et al. Adv. Drug Delivery Rev., 19(2): 115-130 (1996).

* cited by examiner (Continued)

Primary Examiner — Michael Barker
(74) Attorney, Agent, or Firm — Dara L. Dinner; Theodore R. Furman

(57) ABSTRACT

The present invention relates to substituted triazole compounds of the formula (I):

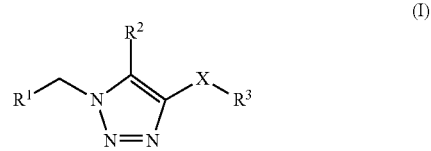

and pharmaceutically acceptable salts thereof, to pharmaceutical compositions containing them and their use in medicine. In particular, the invention relates to compounds for modulating SCD activity.

21 Claims, No Drawings

COMPOUNDS

FIELD OF THE INVENTION

The present invention relates to a novel class of compounds believed to be inhibitors of stearoyl-CoA desaturase (SCD), compositions comprising said compounds, methods of synthesis and uses for such compounds in treating and/or preventing various diseases, including those mediated by SCD enzyme, such as diseases related to elevated lipid levels, cardiovascular disease, diabetes, obesity, metabolic syndrome, skin disorders such as acne, diseases or conditions related to cancer and the treatment of symptoms linked to the production of the amyloid plaque-forming Aβ42 peptide such as Alzheimer's disease and the like.

BACKGROUND OF THE INVENTION

Acyl desaturase enzymes catalyze the formation of double bonds in fatty acids derived from either dietary sources or de novo synthesis in the liver. Mammals synthesise at least three fatty acid desaturases of differing chain length that specifically catalyze the addition of double bonds at the delta-9, delta-6, and delta-5 positions. Stearoyl-CoA desaturases (SCDs) introduce a double bond in the C9-C10 position of saturated fatty acids. The preferred substrates for the enzymes are palmitoyl-CoA (16:0) and stearoyl-CoA (18:0), which are converted to palmitoleoyl-CoA (16:1) and oleoyl-CoA (18:1), respectively. The resulting mono-unsaturated fatty acids may then be employed in the preparation of phospholipids, triglycerides, and cholesteryl esters, in vivo.

A number of mammalian SCD genes have been cloned. For example, two genes have been cloned from rats (SCD1, SCD2) and four SCD genes have been isolated from mice (SCD1, 2, 3 and 4). While the basic biochemical roles of SCD has been known in rats and mice since the 1970's (Jeffcoat, R et al., *Elsevier Science* (1984), Vol 4, pp. 85-112; de Antueno, R J, *Lipids* (1993), Vol. 28, No. 4, pp. 285-290), it has only recently been directly implicated in human diseases processes.

A single SCD gene, SCD1, has been characterized in humans. SCD1 is described in Brownlie et al, WO 01/62954. A second human SCD isoform has been identified, and because it bears little sequence homology to known mouse or rat isoforms it has been named human SCD5 or hSCD5 (WO 02/26944).

Whilst not wishing to be bound by theory, it is thought that inhibition of the activity of SCD in vivo can be used to ameliorate and/or treat one or more diseases such as dyslipidemia, hypoalphalipoproteinemia, hyperbetalipoproteinemia, hypercholesterolemia, hypertriglyceridemia, familial hypercholesterolemia, angina, ischemia, cardiac ischemia, stroke, myocardial infarction, atherosclerosis, obesity, Type I diabetes, Type II diabetes, insulin resistance, hyperinsulinaemia, metabolic syndrome; other cardiovascular diseases e.g. peripheral vascular disease, reperfusion injury, angioplastic restenosis, hypertension, vascular complications of diabetes, thrombosis; hepatic steatosis, non-alcoholic steatohepatitis (NASH) and other diseases related to accumulation of lipids in the liver.

An SCD-mediated disease or condition also includes a disorder of polyunsaturated fatty acid (PUFA) disorder, or a skin disorder, including but not limited to eczema, acne, psoriasis, keloid scar formation or prevention, diseases related to production or secretions from mucous membranes, such as monounsaturated fatty acids, wax esters, and the like (US2006/0205713A1, WO2007/046868, WO2007/046867).

SCD has been shown to play a physiological role in cholesterol homeostasis and the de novo biosynthesis of cholesterol esters, triglycerides and wax esters required for normal skin and eyelid function and therefore may be useful in the treatment of acne and other skin conditions (Makoto et al. J of Nutrition (2001), 131(9), 2260-2268, Harrison et al. J of Investigative Dermatology (2007) 127(6), 1309-1317).

An SCD-mediated disease or condition also includes but is not limited to a disease or condition which is, or is related to cancer, neoplasia, malignancy, metastases, tumours (benign or malignant), carcinogenesis, hepatomas and the like (US2006/0205713A1, WO2007/046868, WO2007/046867). Recently, SCD-1 has been identified as playing a role in human tumor cell survival and therefore has potential as an anticancer target (Morgan-Lappe et al. 2007 Cancer Res. 67(9) 4390-4398).

It has been shown that overexpression of Steroyl-CoA desaturase (SCD) in human cells in culture leads to a specific increase in the production of the amyloid plaque-forming Aβ42 peptide, and conversely, that reductions in SCD activity in human cells in culture leads to a specific decrease in the production of Aβ42. Therefore, SCD inhibitors may also be useful for treating, delaying the onset of symptoms, or slowing the progression of symptoms of mild cognitive impairment (MCI), Alzheimer's Disease (AD), cerebral amyloid angiopathy (CAA) or dementia associated with Down Syndrome (DS) and other neurodegenerative diseases characterized by the formation or accumulation of amyloid plaques comprising Aβ42 (US2007/0087363A1; Myriad Genetics).

WO2005/011657 describes certain piperazine derivatives useful for inhibiting SCD activity.

The present invention provides a compound of formula (I) for inhibiting SCD activity:

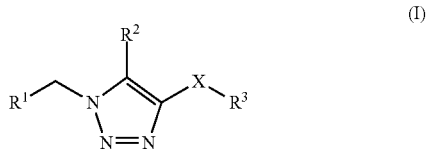

wherein:
X represents —CONH—, —NHCO— or —CH$_2$NH—;
R$^1$ represents:
—C$_{6-10}$aryl (such as phenyl) optionally substituted by one, two or three groups independently selected from:
(a) —C$_{1-6}$alkyl (such as —CH$_3$, or —CH(CH$_3$)$_2$), —OCH$_3$, —C$_{1-6}$haloalkyl (such as —CF$_3$), —OC$_{1-6}$haloalkyl (such as —OCF$_3$), —C$_{3-6}$cycloalkyl, —OC$_{3-6}$cycloalkyl or halogen (such as chloro, bromo or fluoro);
(b) phenyl optionally substituted by one, two or three groups independently selected from: halogen (such as chloro, bromo or fluoro);
R$^2$ represents hydrogen or —C$_{1-6}$alkyl (such as —CH$_3$);
R$^3$ represents:
—C$_{6-10}$aryl (such as phenyl) optionally substituted by one, two or three groups independently selected from:
(a) —C$_{1-6}$alkyl (such as —CH$_3$), —C$_{1-6}$alkenyl, —C$_{1-6}$alkoxy (such as —OCH$_3$ or —OC$_2$H$_4$CH(CH$_3$)$_2$), —O(CH$_2$)$_m$R$^4$, —(CH$_2$)$_m$OC(=O)R$^4$, —(CH$_2$)$_n$CO$_2$R$^5$, —(CH$_2$)$_n$OC(=O)R$^5$, —C$_{0-6}$alkylOH (such as —CH$_2$OH, —C(CH$_3$)$_2$OH or —CH(CH$_3$)OH), —C(=O)NHR$^6$, —(CH$_2$)$_p$NHC(=O)R$^7$, —O(CH$_2$)$_q$NR$^8$R$^9$, —OC$_{1-6}$alkylOH, —C$_{1-6}$haloalkyl (such as —CF$_3$), —OC$_{1-6}$haloalkyl (such as —OCF$_3$), —C$_{3-6}$cycloalkyl, —OC$_{3-6}$cycloalkyl or halogen (such as chloro, bromo or fluoro);
(b) —C$_5$heteroaryl (such as oxazole);
R$^4$ represents —C$_{6-10}$aryl (such as phenyl);
R$^5$ represents —H or —C$_{1-6}$alkyl (such as —CH$_3$);
R$^6$ represents —H or —C$_{1-3}$alkyl (such as —CH$_3$) or —C$_{1-3}$alkylOH;
R$^7$ represents —H or —C$_{1-3}$alkyl (such as —CH$_3$);
R$^8$ represents —H or —C$_{1-3}$alkyl (such as —CH$_3$);
R$^9$ represents —H or —C$_{1-3}$alkyl (such as —CH$_3$);
m represents 1-3;
n represents 0-3;
p represents 0-3; and
q represents 1-3;
or a pharmaceutically acceptable salt thereof;
with the proviso that the compound of formula (I) is not N-[3,5-bis(trifluoromethyl)phenyl]-1-(phenylmethyl)-1H-1,2,3-triazole-4-carboxamide,

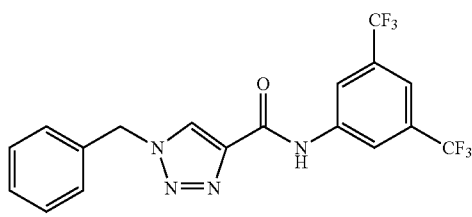 [SMILES: O=C(Nc1cc(C(F)(F)F)cc(C(F)(F)F)c1)c1cn(Cc2ccccc2)nn1]

N-[2-(5-methyl-2-furanyl)phenyl]-1-[(4-methylphenyl)methyl]-1H-1,2,3-triazole-4-carboxamide,

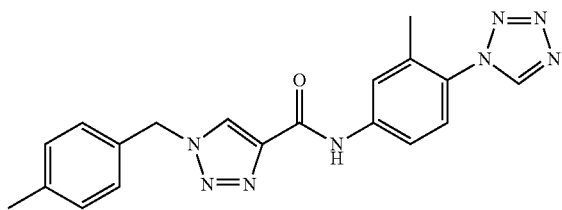 [SMILES: Cc1ccc(Cn2cc(C(=O)Nc3ccc(-n4cnnn4)c(C)c3)nn2)cc1]

or, N-phenyl-1-(phenylmethyl)-1H-1,2,3-triazole-4-carboxamide.

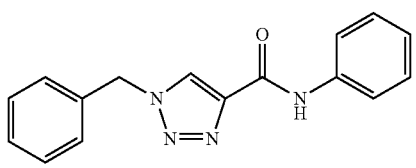 [SMILES: O=C(Nc1ccccc1)c1cn(Cc2ccccc2)nn1]

The said compounds have been found to inhibit SCD activity and may therefore be useful in the treatment of SCD-mediated diseases such as diseases or conditions caused by or associated with an abnormal plasma lipid profile including dyslipidemia, hypoalphalipoproteinemia, hyperbetalipoproteinemia, hypercholesterolemia, hypertriglyceridemia, familial hypercholesterolemia, angina, ischemia, cardiac ischemia, stroke, myocardial infarction, atherosclerosis, obesity, Type I diabetes, Type II diabetes, insulin resistance, hyperinsulinaemia and metabolic syndrome; other cardiovascular diseases e.g. peripheral vascular disease, reperfusion injury, angioplastic restenosis, hypertension, vascular complications of diabetes, thrombosis, hepatic steatosis, non-alcoholic steatoheptatis (NASH) and other diseases related to accumulation of lipids in the liver; skin disorders e.g. eczema, acne, psoriasis, skin ageing, keloid scar formation or prevention, and diseases related to production or secretions from mucous membranes; cancer, neoplasia, malignancy, metastases, tumours (benign or malignant), carcinogenesis, hepatomas and the like; mild cognitive impairment (MCI), Alzheimer's Disease (AD), cerebral amyloid angiopathy (CAA) or dementia associated with Down Syndrome (DS) and other neurodegenerative diseases characterized by the formation or accumulation of amyloid plaques comprising Aβ42.

In one aspect of the invention, X represents —CONH—. In another aspect of the invention, X represents —NHCO—. In another aspect of the invention, X represents —CH$_2$NH—. In another aspect of the invention, X represents —CONH— or —CH$_2$NH—.

In one aspect of the invention, R$^1$ represents phenyl substituted by one, two or three groups independently selected from:
(a) —C$_{1-6}$alkyl (such as —CH$_3$ or —CH(CH$_3$)$_2$), —OCH$_3$, —C$_{1-6}$haloalkyl (such as —CF$_3$), —OC$_{1-6}$haloalkyl (such as —OCF$_3$), —C$_{3-6}$cycloalkyl, —OC$_{3-6}$cycloalkyl or halogen (such as chloro, bromo or fluoro),
(b) phenyl optionally substituted by one, two or three groups selected from: halogen (such as chloro, bromo or fluoro).

In another aspect of the invention, R$^1$ represents phenyl optionally substituted by one, two or three groups independently selected from:
(a) —C$_{1-6}$alkyl (such as —CH$_3$ or —CH(CH$_3$)$_2$), —OCH$_3$, —C$_{1-6}$haloalkyl (such as —CF$_3$), —OC$_{1-6}$haloalkyl (such as —OCF$_3$), —C$_{3-6}$cycloalkyl, —OC$_{3-6}$cycloalkyl or halogen (such as chloro, bromo or fluoro),
(b) phenyl optionally substituted by one, two or three groups selected from: halogen (such as chloro, bromo or fluoro).

In another aspect of the invention, R$^1$ represents phenyl optionally substituted by one or two groups independently selected from: —C$_{1-6}$alkyl (such as —CH$_3$ or CH(CH$_3$)$_2$), —OCH$_3$, —C$_{1-6}$haloalkyl (such as —CF$_3$), —OC$_{1-6}$haloalkyl (such as —OCF$_3$), —C$_{3-6}$cycloalkyl, —OC$_{3-6}$cycloalkyl or halogen (such as chloro, bromo or fluoro), or phenyl optionally substituted by one or two groups selected from: halogen (such as chloro, bromo or fluoro).

In another aspect of the invention, R$^1$ represents phenyl optionally substituted by one, two or three groups independently selected from: —C$_{1-3}$alkyl (such as —CH$_3$ or —CH(CH$_3$)$_2$), —OCH$_3$, —C$_{1-3}$haloalkyl (such as —CF$_3$), —OC$_{1-3}$haloalkyl (such as —OCF$_3$), —C$_{3-6}$cycloalkyl, —OC$_{3-6}$cycloalkyl or halogen (such as chloro, bromo or fluoro), or phenyl optionally substituted by one, two or three groups selected from: halogen (such as chloro, bromo or fluoro).

In another aspect of the invention, R$^1$ represents phenyl optionally substituted by one or two groups independently selected from: —C$_{1-3}$alkyl (such as —CH$_3$ or —CH(CH$_3$)$_2$), —OCH$_3$, —C$_{1-3}$haloalkyl (such as —CF$_3$), —OC$_{1-3}$haloalkyl (such as —OCF$_3$), —C$_{3-6}$cycloalkyl, —OC$_{3-6}$cycloalkyl or halogen (such as chloro, bromo or fluoro), or phenyl optionally substituted by one or two groups selected from: halogen (such as chloro, bromo or fluoro).

In another aspect of the invention, R$^1$ represents phenyl optionally substituted by one, two or three groups independently selected from: —C$_{1-6}$alkyl (such as —CH$_3$ or —CH(CH$_3$)$_2$) or halogen (such as chloro, bromo or fluoro) or phenyl optionally substituted by one, two or three groups selected from: halogen (such as chloro, bromo or fluoro).

In another aspect of the invention, $R^1$ represents phenyl optionally substituted by one or two groups independently selected from: —$C_{1-6}$alkyl (such as —$CH_3$ or —$CH(CH_3)_2$) or halogen (such as chloro, bromo or fluoro) or phenyl optionally substituted by one or two groups selected from: halogen (such as chloro, bromo or fluoro).

In another aspect of the invention, $R^1$ represents phenyl optionally substituted by one, two or three groups independently selected from: —$C_{1-3}$alkyl (such as —$CH_3$ or —$CH(CH_3)_2$) or halogen (such as chloro, bromo or fluoro) or phenyl optionally substituted by one, two or three groups selected from: halogen (such as chloro, bromo or fluoro).

In another aspect of the invention, $R^1$ represents phenyl optionally substituted by one or two groups independently selected from: —$C_{1-3}$alkyl (such as —$CH_3$ or —$CH(CH_3)_2$) or halogen (such as chloro, bromo or fluoro) or phenyl optionally substituted by one or two groups selected from: halogen (such as chloro, bromo or fluoro).

In another aspect of the invention, $R^1$ represents phenyl optionally substituted by one, two or three groups independently selected from: —$CH_3$, —$CH(CH_3)_2$ or halogen (such as chloro, bromo or fluoro) or phenyl optionally substituted by one, two or three groups selected from: halogen (such as chloro, bromo or fluoro).

In another aspect of the invention, $R^1$ represents phenyl optionally substituted by one or two groups independently selected from: —$CH_3$, —$CH(CH_3)_2$ or halogen (such as chloro, bromo or fluoro) or phenyl optionally substituted by one or two groups selected from: halogen (such as chloro, bromo or fluoro).

In another aspect of the invention, $R^1$ represents phenyl substituted by two groups independently selected from halogen (such as chloro, bromo or fluoro).

In another aspect of the invention, $R^1$ represents phenyl substituted by a group independently selected from halogen (such as chloro, bromo or fluoro).

In another aspect of the invention, $R^1$ represents phenyl substituted by phenyl optionally substituted by halogen (such as chloro, bromo or fluoro).

In another aspect of the invention, $R^1$ represents phenyl substituted by phenyl.

In another aspect of the invention, $R^1$ represents phenyl substituted by two chloro groups.

In another aspect of the invention, $R^1$ is phenyl substituted in the meta position, that is in the 3 position, and the para position, that is in the 4 position, by halogen e.g chloro i.e.

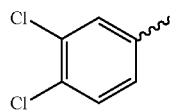

In another aspect of the invention, $R^1$ is phenyl substituted in the meta position, that is in the 3 position and 5 position, by halogen e.g chloro i.e

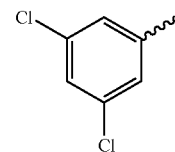

In another aspect of the invention, $R^1$ is phenyl.

In one aspect of the invention, $R^2$ represents hydrogen. In another aspect of the invention, $R^2$ represents —$C_{1-6}$alkyl. In another aspect of the invention, $R^2$ represents —$C_{1-3}$alkyl. In another aspect of the invention, $R^2$ represents —$CH_3$ (methyl). In another aspect of the invention, $R^2$ represents hydrogen or —$C_{1-3}$alkyl.

In one aspect of the invention, $R^3$ represents phenyl optionally substituted by one, two or three groups independently selected from:
  (a) —$C_{1-6}$alkyl (such as —$CH_3$), —$C_{1-6}$alkenyl, —$C_{1-6}$alkoxy (such as —$OCH_3$ or —$OC_2H_4CH(CH_3)_2$), —$O(CH_2)_mR^4$, —$(CH_2)_mOC(=O)R^4$, —$(CH_2)_nCO_2R^5$, —$(CH_2)_nOC(=O)R^5$, —$C_{0-6}$alkylOH (such as —$CH_2OH$, —$C(CH_3)_2OH$ or —$CH(CH_3)OH$), —$C(=O)NHR^6$, —$(CH_2)_pNHC(=O)R^7$, —$O(CH_2)_qNR^8R^9$, —$OC_{1-6}$alkylOH, —$C_{1-6}$haloalkyl (such as —$CF_3$), —$OC_{1-6}$haloalkyl (such as —$OCF_3$), —$C_{3-6}$cycloalkyl, —$OC_{3-6}$cycloalkyl or halogen (such as chloro, bromo or fluoro),
  (b) —$C_5$heteroaryl (such as oxazole).

In another aspect of the invention, $R^3$ represents phenyl optionally substituted by one or two groups independently selected from:
  (a) —$C_{1-6}$alkyl (such as —$CH_3$), —$C_{1-6}$alkenyl, —$C_{1-6}$alkoxy (such as —$OCH_3$ or —$OC_2H_4CH(CH_3)_2$), —$O(CH_2)_mR^4$, —$(CH_2)_mOC(=O)R^4$, —$(CH_2)_nCO_2R^5$, —$(CH_2)_nOC(=O)R^5$, —$C_{0-6}$alkylOH (such as —$CH_2OH$, —$C(CH_3)_2OH$ or —$CH(CH_3)OH$), —$C(=O)NHR^6$, —$(CH_2)_pNHC(=O)R^7$, —$O(CH_2)_qNR^8R^9$, —$OC_{1-6}$alkylOH, —$C_{1-6}$haloalkyl (such as —$CF_3$), —$OC_{1-6}$haloalkyl (such as —$OCF_3$), —$C_{3-6}$cycloalkyl, —$OC_{3-6}$cycloalkyl or halogen (such as chloro, bromo or fluoro),
  (b) —$C_5$heteroaryl (such as oxazole).

In another aspect of the invention, $R^3$ represents phenyl optionally substituted by:
  (i) one group independently selected from —$(CH_2)_nCO_2R^5$ or —$C(=O)NHR^6$ and/or,
  (ii) one, two or three groups independently selected from:
    (a) —$C_{1-6}$alkyl (such as —$CH_3$), —$C_{1-6}$alkenyl, —$C_{1-6}$alkoxy (such as —$OCH_3$ or —$OC_2H_4CH(CH_3)_2$), —$O(CH_2)_mR^4$, —$(CH_2)_mOC(=O)R^4$, —$(CH_2)_nOC(=O)R^5$, —$C_{0-6}$alkylOH (such as —$CH_2OH$, —$C(CH_3)_2OH$ or —$CH(CH_3)OH$), —$(CH_2)_pNHC(=O)R^7$, —$O(CH_2)_qNR^8R^9$, —$OC_{1-6}$alkylOH, —$C_{1-6}$haloalkyl (such as —$CF_3$), —$OC_{1-6}$haloalkyl (such as —$OCF_3$), —$C_{3-6}$cycloalkyl, —$OC_{3-6}$cycloalkyl or halogen (such as chloro, bromo or fluoro),
    (b) —$C_5$heteroaryl (such as oxazole).

In another aspect of the invention, $R^3$ represents phenyl optionally substituted by:
  (i) one group independently selected from —$(CH_2)_nCO_2R^5$ or —$C(=O)NHR^6$ and/or,
  (ii) one or two groups independently selected from:
    (a) —$C_{1-6}$alkyl (such as —$CH_3$), —$C_{1-6}$alkenyl, —$C_{1-6}$alkoxy (such as —$OCH_3$ or —$OC_2H_4CH(CH_3)_2$), —$O(CH_2)_mR^4$, —$(CH_2)_mOC(=O)R^4$, —$(CH_2)_nOC$ (=O)R⁵, —C₀₋₆alkylOH (such as —CH₂OH, —C(CH₃)₂OH or —CH(CH₃)OH), —(CH₂)ₚNHC(=O)R⁷, —O(CH₂)qNR⁸R⁹, —OC₁₋₆alkylOH, —C₁₋₆haloalkyl (such as —CF₃), —OC₁₋₆haloalkyl (such as —OCF₃), —C₃₋₆cycloalkyl, —OC₃₋₆cycloalkyl or halogen (such as chloro, bromo or fluoro), (b) —C₅heteroaryl (such as oxazole).

In another aspect of the invention, R³ represents phenyl optionally substituted by:

(i) one group independently selected from —(CH₂)ₙCO₂R⁵ or —C(=O)NHR⁶ and/or, (ii) one, two or three groups independently selected from:
(a) —C₁₋₃alkyl (such as —CH₃), —C₁₋₃alkenyl, —C₁₋₆alkoxy (such as —OCH₃ or —OC₂H₄CH(CH₃)₂), —O(CH₂)ₘR⁴, —(CH₂)ₘOC(=O)R⁴, —(CH₂)ₙOC(=O)R⁵, —C₀₋₃alkylOH (such as —CH₂OH, —C(CH₃)₂OH or —CH(CH₃)OH), —(CH₂)ₚNHC(=O)R⁷, —O(CH₂)qNR⁸R⁹, —OC₁₋₆alkylOH, —C₁₋₃haloalkyl (such as —CF₃), —OC₁₋₃haloalkyl (such as —OCF₃), —C₃₋₆cycloalkyl, —OC₃₋₆cycloalkyl or halogen (such as chloro, bromo or fluoro), (b) —C₅heteroaryl (such as oxazole).

In another aspect of the invention, R³ represents phenyl optionally substituted by:

(i) one group independently selected from —(CH₂)ₙCO₂R⁵ or —C(=O)NHR⁶ and/or, (ii) one or two groups independently selected from:
(a) —C₁₋₃alkyl (such as —CH₃), —C₁₋₃alkenyl, —C₁₋₆alkoxy (such as —OCH₃ or —OC₂H₄CH(CH₃)₂), —O(CH₂)ₘR⁴, —(CH₂)ₘOC(=O)R⁴, —(CH₂)ₙOC(=O)R⁵, —C₀₋₃alkylOH (such as —CH₂OH, —C(CH₃)₂OH or —CH(CH₃)OH), —(CH₂)ₚNHC(=O)R⁷, —O(CH₂)qNR⁸R⁹, —OC₁₋₆alkylOH, —C₁₋₃haloalkyl (such as —CF₃), —OC₁₋₃haloalkyl (such as —OCF₃), —C₃₋₆cycloalkyl, —OC₃₋₆cycloalkyl or halogen (such as chloro, bromo or fluoro), (b) —C₅heteroaryl (such as oxazole).

In another aspect of the invention, R³ represents phenyl optionally substituted by:

(i) one group independently selected from —(CH₂)ₙCO₂R⁵ or —C(=O)NHR⁶ and/or, (ii) one, two or three groups independently selected from:
(a) —C₁₋₃alkyl (such as —CH₃), —C₁₋₃alkenyl, —C₁₋₆alkoxy (such as —OCH₃ or —OC₂H₄CH(CH₃)₂), —O(CH₂)ₘR⁴, —(CH₂)ₘOC(=O)R⁴, —(CH₂)ₙOC(=O)R⁵, —C₀₋₃alkylOH (such as —CH₂OH, —CH(CH₃)₂OH or —CH(CH₃)OH), —(CH₂)ₚNHC(=O)R⁷, —O(CH₂)qNR⁸R⁹, —OC₁₋₆alkylOH or halogen (such as chloro, bromo or fluoro), (b) —C₅heteroaryl (such as oxazole).

In another aspect of the invention, R³ represents phenyl optionally substituted by:

(i) one group independently selected from —(CH₂)ₙCO₂R⁵ or —C(=O)NHR⁶ and/or, (ii) one or two groups independently selected from:
(a) —C₁₋₃alkyl (such as —CH₃), —C₁₋₃alkenyl, —C₁₋₆alkoxy (such as —OCH₃ or —OC₂H₄CH(CH₃)₂), —O(CH₂)ₘR⁴, —(CH₂)ₘOC(=O)R⁴, —(CH₂)ₙOC(=O)R⁵, —C₀₋₃alkylOH (such as —CH₂OH, —C(CH₃)₂OH or —CH(CH₃)OH), —(CH₂)ₚNHC(=O)R⁷, —O(CH₂)qNR⁸R⁹, —OC₁₋₆alkylOH or halogen (such as chloro, bromo or fluoro), (b) oxazole.

In another aspect of the invention, R³ represents phenyl optionally substituted by:

(i) one group independently selected from —CO₂H, —CO₂CH₃, —CO₂C₂H₅, —CH₂CO₂CH₃, —CH₂CO₂C₂H₅, —C(=O)NH₂, —C(=O)NHCH₃, —C(=O)NHC₂H₅ or —C(=O)NHC₂H₄OH and/or, (ii) one, two or three groups independently selected from:
(a) —CH₃, —C(=CH₂)CH₃, —OCH₃, —OC₂H₄CH(CH₃)₂, —OCH₂R⁴, —CH₂OC(=O)R⁴, —CH₂C(=O)CH₃, —CH₂OH, —C₂H₄OH, —CH(CH₃)OH, —C(CH₃)₂OH, —OH, —CH₂NHC(=O)CH₃, —NHC(=O)CH₃, —OC₂H₄N(CH₃)₂, —OC₂H₄OH or halogen (such as chloro, bromo or fluoro), (b) oxazole.

In another aspect of the invention, R³ represents phenyl optionally substituted by:

(i) one group independently selected from —CO₂H, —CO₂CH₃, —CO₂C₂H₅, —CH₂CO₂CH₃, —CH₂CO₂C₂H₅, —C(=O)NH₂, —C(=O)NHCH₃, —C(=O)NHC₂H₅ or —C(=O)NHC₂H₄OH and/or, (ii) one or two groups independently selected from:
(a) —CH₃, —C(=CH₂)CH₃, —OCH₃, —OC₂H₄CH(CH₃)₂, —OCH₂R⁴, —CH₂C(=O)R⁴, —CH₂C(=O)CH₃, —CH₂OH, —C₂H₄OH, —CH(CH₃)OH, —C(CH₃)₂OH, —OH, —CH₂NHC(=O)CH₃, NHC(=O)CH₃ —OC₂H₄N(CH₃)₂, —OC₂H₄OH or halogen (such as chloro, bromo or fluoro), (b) oxazole.

In another aspect of the invention, R³ represents phenyl optionally substituted by one or two —CH₂OH groups.

In another aspect of the invention, R³ represents phenyl substituted by one or two —CH₂OH groups.

In another aspect of the invention, R³ is phenyl substituted in the meta position, that is in the 3 and 5 position, by —CH₂OH i.e.

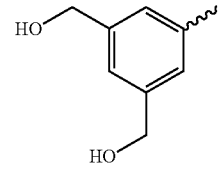

In another aspect of the invention, R¹ is phenyl substituted in the meta position, that is in the 3 position and the para position, that is in the 4 position, by —CH₂OH i.e

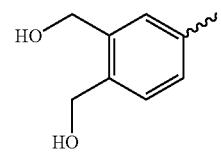

In another aspect of the invention, $R^3$ represents phenyl substituted by —$CH_2OH$.

In one aspect of the invention, $R^4$ represents phenyl.

In one aspect of the invention, $R^5$ represents hydrogen. In another aspect of the invention, $R^5$ represents —$C_{1-6}$alkyl. In another aspect of the invention, $R^5$ represents —$C_{1-3}$alkyl. In another aspect of the invention, $R^5$ represents —$C_2H_5$ (ethyl). In another aspect of the invention, $R^5$ represents —$CH_3$ (methyl).

In one aspect of the invention, $R^6$ represents hydrogen. In another aspect of the invention, $R^6$ represents —$C_{1-3}$alkyl. In another aspect of the invention, $R^6$ represents —$C_2H_5$ (ethyl). In another aspect of the invention, $R^6$ represents —$CH_3$ (methyl). In another aspect of the invention, $R^6$ represents —$C_{1-3}$alkylOH. In another aspect of the invention, $R^6$ represents —$C_2H_4OH$.

In one aspect of the invention, $R^7$ represents hydrogen. In another aspect of the invention, $R^7$ represents —$C_{1-3}$alkyl. In another aspect of the invention, $R^7$ represents —$CH_3$ (methyl).

In one aspect of the invention, $R^9$ represents hydrogen. In another aspect of the invention, $R^9$ represents —$C_{1-3}$alkyl. In another aspect of the invention, $R^9$ represents —$CH_3$ (methyl).

In one aspect of the invention, $R^9$ represents hydrogen. In another aspect of the invention, $R^9$ represents —$C_{1-3}$alkyl. In another aspect of the invention, $R^9$ represents —$CH_3$ (methyl).

In one aspect of the invention, m represents 1 or 2. In another aspect of the invention, m represents 2. In another aspect of the invention, m represents 1.

In one aspect of the invention, n represents 0, 1 or 2. In another aspect of the invention, n represents 3. In another aspect of the invention, n represents 2. In another aspect of the invention, n represents 1. In another aspect of the invention, n represents 0.

In one aspect of the invention, p represents 0, 1 or 2. In another aspect of the invention, p represents 2. In another aspect of the invention, p represents 1. In another aspect of the invention, p represents 0.

In one aspect of the invention, q represents 1 or 2. In another aspect of the invention, q represents 2. In another aspect of the invention, q represents 1.

Each of the aspects of the invention are independent unless stated otherwise. Nevertheless the skilled person will understand that all the permutations of the aspects of described are within the scope of the invention. Thus it is to be understood that the present invention covers all combinations of suitable, convenient and exemplified groups described herein. For example, in one aspect the invention provides a compound of formula (I) wherein X represents —CONH— and $R^2$ represents —$CH_3$.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The invention also extends to conformational isomers of compounds of formula (I) and any geometric (cis and/or trans) isomers of said compounds. Likewise, it is understood that compounds of formula (I) may exist in tautomeric forms other than that shown in the formula and these are also included within the scope of the present invention.

It will be appreciated that racemic compounds of formula (I) may be optionally resolved into their individual enantiomers. Such resolutions may conveniently be accomplished by standard methods known in the art. For example, a racemic compound of formula (I) may be resolved by chiral preparative HPLC.

It will also be appreciated that compounds of the invention which exist as polymorphs, and mixtures thereof, are within the scope of the present invention.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl. However, when a moiety is defined such that alkyl bears a substituent it will be clear to the skilled person from the context that alkyl may include alkylene, for example methylene (—$CH_2$—), ethylene (—$CH_2CH_2$—) and propylene (—$CH_2CH_2CH_2$—).

As used herein, the term "alkylOH" refers to straight or branched hydrocarbon chains containing the specified number of carbon atoms and a hydroxyl group. For example, —$C_{1-6}$alkylOH means a straight or branched alkyl containing at least 1, and at most 6, carbon atoms and OH.

In one aspect of the invention, the term "alkylOH" refers to straight hydrocarbon chains containing the specified number of carbon atoms and a hydroxyl group. For example, —$C_{1-6}$alkylOH means a straight alkyl containing at least 1, and at most 6, carbon atoms and OH. In one aspect of the invention, the alkyl chain in —$C_{1-6}$alkylOH is a straight hydrocarbon chain containing the specified number of carbon atoms and a hydroxyl group.

As used herein, the term "alkenyl" refers to straight or branched chain hydrocarbon chains containing the specified number of carbon atoms and one or more double bonds. For example, —$C_{1-6}$alkenyl means a straight or branched alkyl containing at least 1, and at most 6, carbon atoms and at least one double bond. Examples of "alkenyl" as used herein include, but are not limited to, ethenyl, 1-methylethenyl, propyl-2-ene, 2-propenyl, 3-butenyl, 2-butenyl, 2-pentenyl, 3-pentenyl, 3-methyl-2-butenyl or 3-hexenyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. The point of attachment may be on the oxygen or carbon atom.

As used herein, the term "halogen" or "halo" refers to a fluorine (fluoro), chlorine (chloro), bromine (bromo) or iodine (iodo) atom.

As used herein, the term "haloalkyl" refers to an alkyl group having one or more carbon atoms and wherein at least one hydrogen atom is replaced with a halogen atom, for example a trifluoromethyl group and the like.

As used herein, the term "cycloalkyl" refers to a saturated cyclic group containing 3 to 6 carbon ring-atoms. Examples include cyclopropyl, cyclopentyl and cyclohexyl.

As used herein, the term "$C_{5-10}$heteroaryl" refers to an aromatic cyclic group containing 5 to 10 ring-atoms 1, 2, 3 or 4 of which are hetero-atoms independently selected from nitrogen, oxygen and sulphur and the remaining ring-atoms are carbon, e.g. benzothiophenyl, indolyl or thienyl. This definition includes both monocyclic and bicyclic ring systems and bicyclic structures at least a portion of which is aromatic and the other part is saturated, partially or fully unsaturated.

As used herein, the term 'aryl' means an aromatic carbocyclic moiety. The definition includes both monocyclic and bicyclic ring systems and bicyclic structures at least a portion of which is aromatic and the other part is saturated, partially or fully unsaturated. Examples of aromatic, aryl groups include naphthyl, anthryl, phenanthryl, indanyl, indenyl, azulenyl, azulanyl, fluorenyl, phenyl and napthyl, and more specifically phenyl.

Examples of heteroaryl groups include: furyl, thienyl, pyrrolyl, pyrrolinyl, imidazolyl, oxazolyl, thiazolyl, imidazolyl, pyrazolyl, pyrazolinyl, isoxazolyl, isothiazolyl, oxadiazolyl, triazolyl, thiadiazolyl, pyranyl, pyridyl, pyridazinyl, pyrimidinyl, pyrazinyl, sulfolanyl, tetrazolyl, triazinyl, azepinyl, oxazepinyl, thiazepinyl, diazepinyl and thiazolinyl, benzimidazolyl, benzoxazolyl, imidazopyridinyl, benzoxazinyl, benzothiazinyl, benzothiophenyl oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl.

In one aspect of the invention, —$C_5$heteroaryl is a 5 membered aromatic cyclic group containing 5 ring-atoms 1, 2 or 3 of which are hetero-atoms independently selected from nitrogen, oxygen and sulphur and the remaining ring-atoms are carbon, e.g. oxazole.

As used herein, the term "substituted" refers to substitution with the named substituent or substituents, multiple degrees of substitution being allowed unless otherwise stated. For the avoidance of doubt, the term "independently" means that where more than one substituent is selected from a number of possible substituents, those substituents may be the same or different.

As used herein, the term "pharmaceutically acceptable" means a compound which is suitable for pharmaceutical use.

Salts of compounds of formula (I) which are suitable for use in medicine are those wherein the counterion is pharmaceutically acceptable. However, salts having non-pharmaceutically acceptable counterions are within the scope of the present invention, for example, for use as intermediates in the preparation of other compounds of formula (I) and their pharmaceutically acceptable salts.

Suitable pharmaceutically acceptable salts will be apparent to those skilled in the art and include for example acid addition salts formed with inorganic acids e.g. hydrochloric, hydrobromic, sulfuric, nitric or phosphoric acid; and organic acids e.g. succinic, maleic, malic, mandelic, acetic, fumaric, glutamic, lactic, citric, tartaric, benzoic, benzenesulfonic, p-toluenesulfonic, methanesulfonic, ethanesulfonic or naphthalenesulfonic acid. Other non-pharmaceutically acceptable salts e.g. oxalates, may be used, for example in the isolation of compounds of formula (I) and are included within the scope of this invention. Reference is made to Berge et al. J. Pharm. Sci., 1977, 66, 1-19.

Certain of the compounds of formula (I) may form acid addition salts with one or more equivalents of the acid. The present invention includes within its scope all possible stoichiometric and non-stoichiometric forms thereof.

Solvates of the compounds of formula (I) and solvates of the salts of the compounds of formula (I) are included within the scope of the present invention.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include, but are not limited to, water, methanol, ethanol and acetic acid. In one aspect of the invention, the solvent used is a pharmaceutically acceptable solvent. In another aspect of the invention, the solvent used is water and the solvate may also be referred to as a hydrate.

Solvates of compounds of formula (I) which are suitable for use in medicine are those wherein the solvent is pharmaceutically acceptable. However, solvates having non-pharmaceutically acceptable solvents are within the scope of the present invention, for example, for use as intermediates in the preparation of other compounds of formula (I) and their pharmaceutically acceptable salts.

Prodrugs of the compounds of formula (I) are included within the scope of the present invention.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987 and in D. Fleishner, S. Ramon and H. Barba "Improved oral drug delivery: solubility limitations overcome by the use of prodrugs", Advanced Drug Delivery Reviews (1996) 19(2) 115-130. Prodrugs are any covalently bonded carriers that release a compound of structure (I) in vivo when such prodrug is administered to a patient. Prodrugs are generally prepared by modifying functional groups in a way such that the modification is cleaved in vivo yielding the parent compound. Prodrugs may include, for example, compounds of this invention wherein hydroxyl or amine groups are bonded to any group that, when administered to a patient, cleaves to form the hydroxy or amine groups. Thus, representative examples of prodrugs include (but are not limited to) phosphonate, carbamate, acetate, formate and benzoate derivatives of hydroxy and amine functional groups of the compounds of formula (I).

Phosphonates, acetates, benzoates and carbamates may be active in their own right and/or be hydrolysable under in vivo conditions in the human body. Suitable pharmaceutically acceptable in vivo hydrolysable ester groups include those which break down readily in the human body to leave the parent acid or its salt. A phosphonate is formed by reaction with phosphorous (phosphonic) acid, by methods well known in the art. For example, phosphonates may be derivatives such as $RP(O)(OR)_2$ and the like. A acetate is an ester of acetic acid. A benzoate is an ester of benzenecarboxylic acid. A carbamate is an ester of carbamic acid.

In one aspect of the invention there is provided a compound, or a pharmaceutically acceptable salt thereof, wherein the compound is selected from the group consisting of:

N-[3,4-bis(methyloxy)phenyl]-1-[(4-fluorophenyl)methyl]-5-methyl-1H-1,2,3-triazole-4-carboxamide, N-[3,4-bis(methyloxy)phenyl]-1-[(4-bromophenyl)methyl]-5-methyl-1H-1,2,3-triazole-4-carboxamide, 1-[(4-Bromophenyl)methyl]-5-methyl-N-{4-[(phenylmethyl)oxy]phenyl}-1H-1,2,3-triazole-4-carboxamide, 1-[(4-Fluorophenyl)methyl]-5-methyl-N-{4-[(phenylmethyl)oxy]phenyl}-1H-1,2,3-triazole-4-carboxamide, 1-[(4-Fluorophenyl)methyl]-5-methyl-N-{4-[(3-methylbutyl)oxy]phenyl}-1H-1,2,3-triazole-4-carboxamide, 1-[(4-Bromophenyl)methyl]-5-methyl-N-{4-[(3-methylbutyl)oxy]phenyl}-1H-1,2,3-triazole-4-carboxamide, 5-Methyl-1-(phenylmethyl)-N-{4-[(phenylmethyl)oxy]phenyl}-1H-1,2,3-triazole-4-carboxamide, 5-Methyl-N-{4-[(3-methylbutyl)oxy]phenyl}-1-(phenylmethyl)-1H-1,2,3-triazole-4-carboxamide, 1-[(2'-Chloro-4-biphenylyl)methyl]-5-methyl-N-{4-[(3-methylbutyl)oxy]phenyl}-1H-1,2,3-triazole-4-carboxamide, 5-Methyl-N-{4-[(3-methylbutyl)oxy]phenyl}-1-[(4-methylphenyl)methyl]-1H-1,2,3-triazole-4-carboxamide, 5-Methyl-N-{4-[(3-methylbutyl)oxy]phenyl}-1-{[4-(1-methylethyl)phenyl]methyl}-1H-1,2,3-triazole-4-carboxamide, N-[3,4-Bis(methyloxy)phenyl]-5-methyl-1-[(4-methylphenyl)methyl]-1H-1,2,3-triazole-4-carboxamide, 1-(2-Biphenylylmethyl)-N-[3,4-bis(methyloxy)phenyl]-5-methyl-1H-1,2,3-triazole-4-carboxamide, N-[3,4-Bis(methyloxy)phenyl]-1-[(4-fluorophenyl)methyl]-1H-1,2,3-triazole-4-carboxamide, 1-[(3,4-Dichlorophenyl)methyl]-5-methyl-N-[4-(1,3-oxazol-2-yl)phenyl]-1H-1,2,3-triazole-4-carboxamide, 1-[(3,4-Dichlorophenyl)methyl]-N-[4-(hydroxymethyl)phenyl]-5-methyl-1H-1,2,3-triazole-4-carboxamide, Methyl 4-[({1-[(3,4-dichlorophenyl)methyl]-5-methyl-1H-1,2,3-triazol-4-yl}carbonyl)amino]-3-(methyloxy)benzoate, 1-[(3,4-Dichlorophenyl)methyl]-5-methyl-N-{3-[(methylamino)carbonyl]phenyl}-1H-1,2,3-triazole-4-carboxamide, 1-[(3,4-Dichlorophenyl)methyl]-5-methyl-N-{4-[(methylamino)carbonyl]phenyl}-1H-1,2,3-triazole-4-carboxamide, Ethyl 3-[({1-[(3,4-dichlorophenyl)methyl]-5-methyl-1H-1,2,3-triazol-4-yl}carbonyl)amino]benzoate, N-[3-(acetylamino)phenyl]-1-[(3,4-dichlorophenyl)methyl]-5-methyl-1H-1,2,3-triazole-4-carboxamide, N-[4-(acetylamino)phenyl]-1-[(3,4-dichlorophenyl)methyl]-5-methyl-1H-1,2,3-triazole-4-carboxamide, 1-[(3,4-Dichlorophenyl)methyl]-N-[3-(hydroxymethyl)-2-methylphenyl]-5-methyl-1H-1,2,3-triazole-4-carboxamide, 1-[(3,4-Dichlorophenyl)methyl]-N-[3-(hydroxymethyl)phenyl]-5-methyl-1H-1,2,3-triazole-4-carboxamide, Methyl 3-[({1-[(3,4-dichlorophenyl)methyl]-5-methyl-1H-1,2,3-triazol-4-yl}carbonyl)amino]-4-(methyloxy)benzoate, 1-[(3,4-Dichlorophenyl)methyl]-N-[4-hydroxy-3-(hydroxymethyl)phenyl]-5-methyl-1H-1,2,3-triazole-4-carboxamide, Ethyl {4-[({1-[(3,4-dichlorophenyl)methyl]-5-methyl-1H-1,2,3-triazol-4-yl}carbonyl)amino]phenyl}acetate, Methyl 4-[({1-[(3,4-dichlorophenyl)methyl]-5-methyl-1H-1,2,3-triazol-4-yl}carbonyl)amino]-2-(methyloxy)benzoate, Methyl 5-[({1-[(3,4-dichlorophenyl)methyl]-5-methyl-1H-1,2,3-triazol-4-yl}carbonyl)amino]-2-hydroxybenzoate, Methyl {3-[({1-[(3,4-dichlorophenyl)methyl]-5-methyl-1H-1,2,3-triazol-4-yl}carbonyl)amino]phenyl}acetate, 1-[(3,4-Dichlorophenyl)methyl]-N-(3-hydroxyphenyl)-5-methyl-1H-1,2,3-triazole-4-carboxamide, Methyl 5-[({1-[(3,4-dichlorophenyl)methyl]-5-methyl-1H-1,2,3-triazol-4-yl}carbonyl)amino]-2-fluorobenzoate, N-[5-(Aminocarbonyl)-2-(methyloxy)phenyl]-1-[(3,4-dichlorophenyl)methyl]-5-methyl-1H-1,2,3-triazole-4-carboxamide, Methyl 4-chloro-3-[({1-[(3,4-dichlorophenyl)methyl]-5-methyl-1H-1,2,3-triazol-4-yl}carbonyl)amino]benzoate, Methyl [3-[({1-[(3,4-dichlorophenyl)methyl]-5-methyl-1H-1,2,3-triazol-4-yl}carbonyl)amino]-4-(methyloxy)phenyl]acetate, Methyl 3-[({1-[(3,4-dichlorophenyl)methyl]-5-methyl-1H-1,2,3-triazol-4-yl}carbonyl)amino]-4-fluorobenzoate, N-[3-(hydroxymethyl)phenyl]-5-methyl-1-(phenylmethyl)-1H-1,2,3-triazole-4-carboxamide, N-[4-(hydroxymethyl)phenyl]-5-methyl-1-(phenylmethyl)-1H-1,2,3-triazole-4-carboxamide, N-[3-(hydroxymethyl)-2-methylphenyl]-5-methyl-1-(phenylmethyl)-1H-1,2,3-triazole-4-carboxamide, 1-[(3,5-Dichlorophenyl)methyl]-N-[3-(hydroxymethyl)phenyl]-5-methyl-1H-1,2,3-triazole-4-carboxamide, Methyl 3-[({1-[(3,5-dichlorophenyl)methyl]-5-methyl-1H-1,2,3-triazol-4-yl}carbonyl)amino]-4-(methyloxy)benzoate, 1-[(3,5-Dichlorophenyl)methyl]-N-[3-(hydroxymethyl)-2-methylphenyl]-5-methyl-1H-1,2,3-triazole-4-carboxamide, N-{3-[(Acetylamino)methyl]phenyl}-1-[(3,4-dichlorophenyl)methyl]-5-methyl-1H-1,2,3-triazole-4-carboxamide, 1-[(3,4-Dichlorophenyl)methyl]-N-[3-(1-hydroxyethyl)phenyl]-5-methyl-1H-1,2,3-triazole-4-carboxamide, N-[4-chloro-3-(hydroxymethyl)phenyl]-1-[(3,4-dichlorophenyl)methyl]-5-methyl-1H-1,2,3-triazole-4-carboxamide, Dimethyl 4-[({1-[(3,4-dichlorophenyl)methyl]-5-methyl-1H-1,2,3-triazol-4-yl}carbonyl)amino]-1,2-benzenedicarboxylate, Methyl 5-[({1-[(3,5-dichlorophenyl)methyl]-5-methyl-1H-1,2,3-triazol-4-yl}carbonyl)amino]-2-fluorobenzoate, Ethyl 4-[({1-[(3,4-dichlorophenyl)methyl]-5-methyl-1H-1,2,3-triazol-4-yl}carbonyl)amino]benzoate, 1-[(3,4-Dichlorophenyl)methyl]-N-[4-(hydroxymethyl)-2-(methyloxy)phenyl]-5-methyl-1H-1,2,3-triazole-4-carboxamide, 1-[(3,4-Dichlorophenyl)methyl]-N-[4-(2-hydroxyethyl)phenyl]-5-methyl-1H-1,2,3-triazole-4-carboxamide, 1-[(3,4-Dichlorophenyl)methyl]-N-[5-(hydroxymethyl)-2-(methyloxy)phenyl]-5-methyl-1H-1,2,3-triazole-4-carboxamide, N-[3,5-Bis(hydroxymethyl)phenyl]-1-[(3,4-dichlorophenyl)methyl]-5-methyl-1H-1,2,3-triazole-4-carboxamide, 1-[(3,4-Dichlorophenyl)methyl]-N-[4-fluoro-3-(hydroxymethyl)phenyl]-5-methyl-1H-1,2,3-triazole-4-carboxamide, 1-[(3,4-Dichlorophenyl)methyl]-N-[5-(2-hydroxyethyl)-2-(methyloxy)phenyl]-5-methyl-1H-1,2,3-triazole-4-carboxamide, 1-[(3,4-Dichlorophenyl)methyl]-N-[2-fluoro-5-(hydroxymethyl)phenyl]-5-methyl-1H-1,2,3-triazole-4-carboxamide, N-[2-chloro-5-(hydroxymethyl)phenyl]-1-[(3,4-dichlorophenyl)methyl]-5-methyl-1H-1,2,3-triazole-4-carboxamide, 1-[(3,5-Dichlorophenyl)methyl]-N-[5-(hydroxymethyl)-2-(methyloxy)phenyl]-5-methyl-1H-1,2,3-triazole-4-carboxamide, N-[3,4-Bis(hydroxymethyl)phenyl]-1-[(3,4-dichlorophenyl)methyl]-5-methyl-1H-1,2,3-triazole-4-carboxamide, 1-[(3,5-Dichlorophenyl)methyl]-N-[4-fluoro-3-(hydroxymethyl)phenyl]-5-methyl-1H-1,2,3-triazole-4-carboxamide, N-[3,5-bis(hydroxymethyl)phenyl]-5-methyl-1-(phenylmethyl)-1H-1,2,3-triazole-4-carboxamide, N-[3,5-bis(hydroxymethyl)phenyl]-1-[(3-chlorophenyl)methyl]-5-methyl-1H-1,2,3-triazole-4-carboxamide, 1-[(3,4-Dichlorophenyl)methyl]-N-[3-(2-hydroxyethyl)phenyl]-5-methyl-1H-1,2,3-triazole-4-carboxamide, 3-[({1-[(3,4-Dichlorophenyl)methyl]-5-methyl-1H-1,2,3-triazol-4-yl}carbonyl)amino]benzoic acid, 3-[({1-[(3,4-Dichlorophenyl)methyl]-5-methyl-1H-1,2,3-triazol-4-yl}carbonyl)amino]-4-(methyloxy)benzoic acid,
5-({[5-Methyl-1-(phenylmethyl)-1H-1,2,3-triazol-4-yl]carbonyl}amino)-1,3-benzenedicarboxylic acid,
4-[({1-[(3,4-Dichlorophenyl)methyl]-5-methyl-1H-1,2,3-triazol-4-yl}carbonyl)amino]benzoic acid,
1-[(3,4-Dichlorophenyl)methyl]-N-{3-[(ethylamino)carbonyl]phenyl}-5-methyl-1H-1,2,3-triazole-4-carboxamide,
1-[(3,4-Dichlorophenyl)methyl]-N-(3-{[(2-hydroxyethyl)amino]carbonyl}phenyl)-5-methyl-1H-1,2,3-triazole-4-carboxamide,
1-[(3,4-Dichlorophenyl)methyl]-5-methyl-N-[5-[(methylamino)carbonyl]-2-(methyloxy)phenyl]-1H-1,2,3-triazole-4-carboxamide,
{3-[({1-[(3,4-Dichlorophenyl)methyl]-5-methyl-1H-1,2,3-triazol-4-yl}carbonyl)amino]phenyl}methyl acetate,
{3-[({1-[(3,5-Dichlorophenyl)methyl]-5-methyl-1H-1,2,3-triazol-4-yl}carbonyl)amino]phenyl}methyl acetate,
{3-[({1-[(3,4-Dichlorophenyl)methyl]-5-methyl-1H-1,2,3-triazol-4-yl}carbonyl)amino]phenyl}methyl benzoate,
{3-[({1-[(3,5-Dichlorophenyl)methyl]-5-methyl-1H-1,2,3-triazol-4-yl}carbonyl)amino]phenyl}methyl benzoate,
1-[(3,4-Dichlorophenyl)methyl]-N-{4-[(2-hydroxyethyl)oxy]phenyl}-5-methyl-1H-1,2,3-triazole-4-carboxamide,
1-[(3,4-Dichlorophenyl)methyl]-5-methyl-N-[4-(1-methylethenyl)-2-(methyloxy)phenyl]-1H-1,2,3-triazole-4-carboxamide,
1-[(3,4-Dichlorophenyl)methyl]-N-[3-(1-hydroxy-1-methylethyl)phenyl]-5-methyl-1H-1,2,3-triazole-4-carboxamide,
1-[(3,4-Dichlorophenyl)methyl]-N-[4-{[2-(dimethylamino)ethyl]oxy}-3-(hydroxymethyl)phenyl]-5-methyl-1H-1,2,3-triazole-4-carboxamide,
1-[(3,4-Dichlorophenyl)methyl]-N-{3-[(2-hydroxyethyl)oxy]phenyl}-5-methyl-1H-1,2,3-triazole-4-carboxamide, or
{5-[({1-[(3,4-Dichlorophenyl)methyl]-5-methyl-1H-1,2,3-triazol-4-yl}methyl)amino]benzene-1,3-diyl}dimethanol.

In another aspect of the invention there is provided a compound, or a pharmaceutically acceptable salt thereof, wherein the compound is selected from the group consisting of:
N-[3,4-bis(hydroxymethyl)phenyl]-5-methyl-1-(phenylmethyl)-1H-1,2,3-triazole-4-carboxamide,
N-[3,5-bis(hydroxymethyl)phenyl]-1-[(4-fluorophenyl)methyl]-5-methyl-1H-1,2,3-triazole-4-carboxamide,
N-[3,4-bis(hydroxymethyl)phenyl]-1-[(3-chlorophenyl)methyl]-5-methyl-1H-1,2,3-triazole-4-carboxamide,
N-[3,4-bis(hydroxymethyl)phenyl]-1-[(4-fluorophenyl)methyl]-5-methyl-1H-1,2,3-triazole-4-carboxamide,
N-[3,5-bis(hydroxymethyl)phenyl]-1-[(3-fluorophenyl)methyl]-5-methyl-1H-1,2,3-triazole-4-carboxamide,
N-[3,4-bis(hydroxymethyl)phenyl]-1-[(3-fluorophenyl)methyl]-5-methyl-1H-1,2,3-triazole-4-carboxamide,
1-[(3-chlorophenyl)methyl]-N-[3-(hydroxymethyl)phenyl]-5-methyl-1H-1,2,3-triazole-4-carboxamide,
1-[(4-fluorophenyl)methyl]-N-[3-(hydroxymethyl)phenyl]-5-methyl-1H-1,2,3-triazole-4-carboxamide,
1-[(3-chlorophenyl)methyl]-N-[4-(hydroxymethyl)phenyl]-5-methyl-1H-1,2,3-triazole-4-carboxamide,
1-[(3-fluorophenyl)methyl]-N-[3-(hydroxymethyl)phenyl]-5-methyl-1H-1,2,3-triazole-4-carboxamide,
1-[(4-fluorophenyl)methyl]-N-[4-(hydroxymethyl)phenyl]-5-methyl-1H-1,2,3-triazole-4-carboxamide,
1-[(3-fluorophenyl)methyl]-N-[4-(hydroxymethyl)phenyl]-5-methyl-1H-1,2,3-triazole-4-carboxamide
1-[(3,4-dichlorophenyl)methyl]-N-{3-(hydroxymethyl)-5-[(methylamino)carbonyl]phenyl}-5-methyl-1H-1,2,3-triazole-4-carboxamide, or
N-{1-[(3,4-dichlorophenyl)methyl]-5-methyl-1H-1,2,3-triazol-4-yl}-4-(hydroxymethyl)benzamide.

The compounds of the invention have been found to inhibit SCD activity and may therefore be useful in regulating lipid levels, e.g. plasma lipid levels. Diseases or conditions caused by or associated with an abnormal plasma lipid profile and for the treatment of which the compounds of the invention may be useful include; dyslipidemia, hypoalphalipoproteinemia, hyperbetalipoproteinemia, hypercholesterolemia, hypertriglyceridemia, familial hypercholesterolemia, angina, ischemia, cardiac ischemia, stroke, myocardial infarction, atherosclerosis, obesity, Type I diabetes, Type II diabetes, insulin resistance, hyperinsulinaemia and metabolic syndrome. Other cardiovascular diseases for which the compounds of the present invention are useful include peripheral vascular disease, reperfusion injury, angioplastic restenosis, hypertension, vascular complications of diabetes and thrombosis. Other diseases or conditions include hepatic steatosis, non-alcoholic steatohepatitis (NASH) and other diseases related to accumulation of lipids in the liver.

The compounds of the invention may also be useful in the treatment of skin disorders e.g. eczema, acne, psoriasis, skin ageing, keloid scar formation or prevention, and diseases related to production or secretions from mucous membranes.

The compounds of the invention may also be useful in the treatment of cancer, neoplasia, malignancy, metastases, tumours (benign or malignant), carcinogenesis, hepatomas and the like.

The compounds of the invention may also be useful in the treatment of mild cognitive impairment (MCI), Alzheimer's disease (AD), cerebral amyloid angiopathy (CAA) or dementia associated with Down Syndrome (DS) and other neurodegenerative diseases characterized by the formation or accumulation of amyloid plaques comprising Aβ42.

Within the context of the present invention, the terms describing the indications used herein are classified in the Merck Manual of Diagnosis and Therapy, 17$^{th}$ Edition and/or the International Classification of Diseases 10$^{th}$ Edition (ICD-10). The various subtypes of the disorders mentioned herein are contemplated as part of the present invention.

In one aspect, the invention provides a compound of formula (I) or a pharmaceutically acceptable salt thereof for use in medical therapy.

In one aspect, the invention provides the use of a compound of formula (I) or a pharmaceutically acceptable salt thereof for the manufacture of a medicament for treating and/or preventing a disease or a condition susceptible to amelioration by an SCD inhibitor.

In another aspect, the invention provides the use of a compound of formula (I) or a pharmaceutically acceptable salt thereof for the manufacture of a medicament for treating and/or preventing acne, psoriasis, skin ageing, cancer, dyslipidemia, hypertriglyceridemia, atherosclerosis, obesity, Type II diabetes, insulin resistance, hyperinsulinaemia, hepatic steatosis and/or non-alcoholic steatohepatitis (NASH).

In another aspect, the invention provides the use of a compound of formula (I) or a pharmaceutically acceptable salt thereof for the manufacture of a medicament for treating and/or preventing acne, psoriasis, skin ageing, cancer, dyslipidemia, atherosclerosis, insulin resistance, hyperinsulinaemia, Type II diabetes and/or hepatic steatosis.

In another aspect, the invention provides the use of a compound of formula (I) or a pharmaceutically acceptable salt thereof for the manufacture of a medicament for treating and/or preventing acne.

In one aspect, the invention provides a compound of formula (I) or a pharmaceutically acceptable salt thereof for use in treating and/or preventing a disease or a condition susceptible to amelioration by an SCD inhibitor in a mammal, including human.

In another aspect, the invention provides a compound of formula (I) or a pharmaceutically acceptable salt thereof for use in treating and/or preventing acne, psoriasis, skin ageing, cancer, dyslipidemia, hypertriglyceridemia, atherosclerosis, obesity, Type II diabetes, insulin resistance, hyperinsulinaemia, hepatic steatosis and/or non-alcoholic steatohepatitis (NASH).

In another aspect, the invention provides a compound of formula (I) or a pharmaceutically acceptable salt thereof for use in treating and/or preventing acne, psoriasis, skin ageing, cancer, dyslipidemia, atherosclerosis, insulin resistance, hyperinsulinaemia, Type II diabetes and/or hepatic steatosis.

In another aspect, the invention provides a compound of formula (I) or a pharmaceutically acceptable salt thereof for use in treating and/or preventing acne.

In one aspect, the invention provides a method for treating and/or preventing a disease or a condition susceptible to amelioration by an SCD inhibitor, which method comprises administering to a subject, for example a mammal, including human, a therapeutically effective amount of a compound of formula (I) or a pharmaceutically acceptable salt thereof.

In another aspect, the invention provides a method for treating and/or preventing a acne, psoriasis, skin ageing, cancer, dyslipidemia, hypertriglyceridemia, atherosclerosis, obesity, Type II diabetes, insulin resistance, hyperinsulinaemia, hepatic steatosis and/or non-alcoholic steatohepatitis (NASH), which method comprises administering to a subject, for example a mammal, including human, a therapeutically effective amount of a compound of formula (I) or a pharmaceutically acceptable salt thereof.

In another aspect, the invention provides a method for treating and/or preventing acne, psoriasis, skin ageing, cancer, dyslipidemia, atherosclerosis, insulin resistance, hyperinsulinaemia, Type II diabetes and/or hepatic steatosis, which method comprises administering to a subject, for example a mammal, including human, a therapeutically effective amount of a compound of formula (I) or a pharmaceutically acceptable salt thereof.

In another aspect, the invention provides a method for treating and/or preventing acne, which method comprises administering to a subject, for example a mammal, including human, a therapeutically effective amount of a compound of formula (I) or a pharmaceutically acceptable salt thereof.

It will be appreciated that reference to "treatment" and "therapy" includes acute treatment or prophylaxis as well as the alleviation of established symptoms.

Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

Processes for the preparation of the compounds of formula (I) form further aspects of the invention. $R^1$, $R^2$, $R^3$, $R^4$, $R^5$, $R^6$, $R^7$ and X are as defined above unless otherwise specified. Throughout the specification, general formulae are designated by Roman numerals (I), (II), (III), (IV) etc.

In certain instances final compounds of formula (I) can be converted into other compounds of formula (I) by techniques known to those in the art, for example, carboxylic acid substituents can be converted to esters or amides by routine techniques.

In a general process, compounds of formula (I), wherein X represents —CONH— and $R^3$ represents,

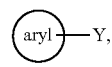

wherein

represents —$C_{6-10}$aryl and Y represents —$C_{1-6}$alkyl, —$C_{1-6}$alkoxy, —$O(CH_2)_mR^4$, —$C_{0-6}$alkylOH, —$(CH_2)_nCO_2R^6$, —(C=O)NHR$^6$, —$(CH_2)_p$NHC(=O)R$^7$, —$O(CH_2)_q$NR$^8$R$^9$, —$C_{1-6}$haloalkyl, —$OC_{1-6}$haloalkyl, —$C_{3-6}$cycloalkyl, —$OC_{3-6}$cycloalkyl, halogen or —$C_5$heteroaryl, (formula (Ia)), may be prepared according to reaction scheme 1 by reacting compounds of formula (II) and compounds of formula (III). The reaction is suitably carried out in the presence of a coupling reagent such as HATU or EDCI and HOBt and base such as DIPEA or NEt$_3$ in a suitable solvent such as DMF (suitably at room temperature to 40° C.).

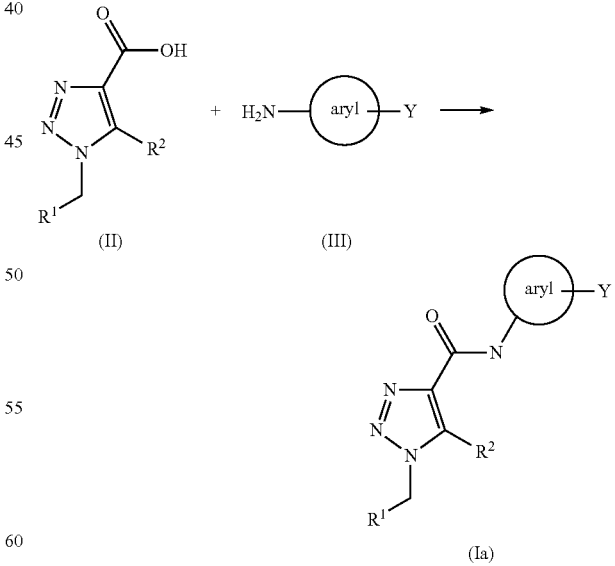

Accordingly, in one aspect the invention provides a process for the preparation of compounds of the formula (Ia) by reacting a compound of formula (II), wherein $R^1$ and $R^2$ are defined above, with a compound of formula (III) wherein Y and are defined above, in the presence of a coupling agent.

Compounds of formula (II) may be prepared according to reaction scheme 2 by reacting compounds of formula (IVa) and compounds of formula (IVb). The reaction is suitably carried out in the presence of base such as potassium carbonate in a suitable solvent such as DMF or DMSO (suitably at 40-80° C.), and is followed by saponification of compounds of formula (IV) in basic conditions such as sodium hydroxide in a suitable solvent, such as ethanol or methanol (to reflux).

Scheme 2

Compounds of formula (II), wherein $R^2$ represents H (formula (IIa)), may be prepared according to reaction scheme 3 by reacting compounds of formula (IVa) and ethyl 2-propynoate in a suitable solvent such as ethanol to reflux, and is followed by saponification of compounds of formula (V) in basic conditions such as sodium hydroxide in a suitable solvent, such as ethanol or methanol (suitably at reflux).

Scheme 3

Compounds of formula (IVa) may be prepared according to reaction scheme 4 by the reaction of benzyl halide chlorine or bromine (VI) with sodium azide in a suitable solvent such as DMSO or DMF (suitably at room temperature to 80° C.).

Scheme 4

Compounds of formula (I), wherein $R^3$ represents aryl—($C_{1-6}$alkyl)—OH and aryl is defined above (formula (Ib)), may also be prepared according to reaction scheme 5 by reduction of the ester function ($Y$=—$(CH_2)_n COOR^5$) of compounds of formula (VII) in the presence of DIBAL-H in solution of toluene. The reaction is suitably carried out in a suitable solvent such as THF at room temperature.

Scheme 5

Accordingly, in another aspect the invention provides a process for the preparation of compounds of the formula (Ib) by reduction of the ester function ($Y$=—$(CH_2)_n COOR^5$) of compounds of the formula (VII), wherein $R^1$, $R^2$ and aryl are defined above.

Compounds of formula (I), wherein $R^3$ represents

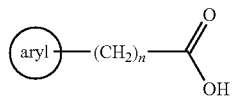

and

is defined above (formula (Ic)), may be prepared according to reaction scheme 6 by saponification of the ester function ($Y=\!\!-\!\!(CH_2)_n COOR^5$) of compounds of the formula (VII) in basic conditions in a suitable solvent such as methanol or ethanol, suitably at reflux.

Scheme 6

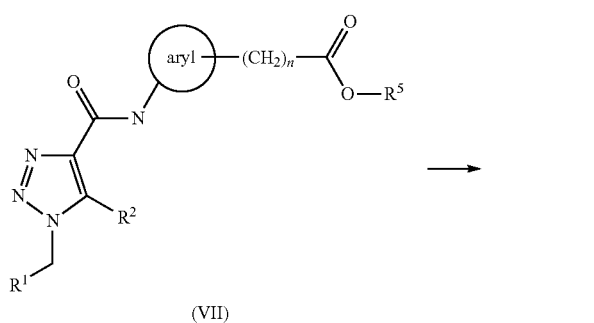

Accordingly, in another aspect the invention provides a process for the preparation of compounds of the formula (Ic) by saponification of the ester function ($Y=\!\!-\!\!(CH_2)_n COOR^5$) of compounds of the formula (VII), wherein $R^1$, $R^2$ and

are defined above, in basic conditions.

Compounds of formula (I), wherein $R^3$ represents

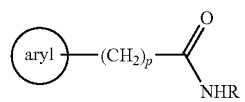

and

is defined above formula (Id)), may be prepared according to reaction scheme 7 by reacting compounds of formula (Ic) and compounds of formula (VIII), wherein R represents $R^6$ or $R^7$, in the presence of a coupling reagent such as HATU, HOBt or EDCI, and a base such as DIPEA or $NEt_3$ in a suitable solvent such as DMF (suitably at room temperature to 40° C.).

Scheme 7

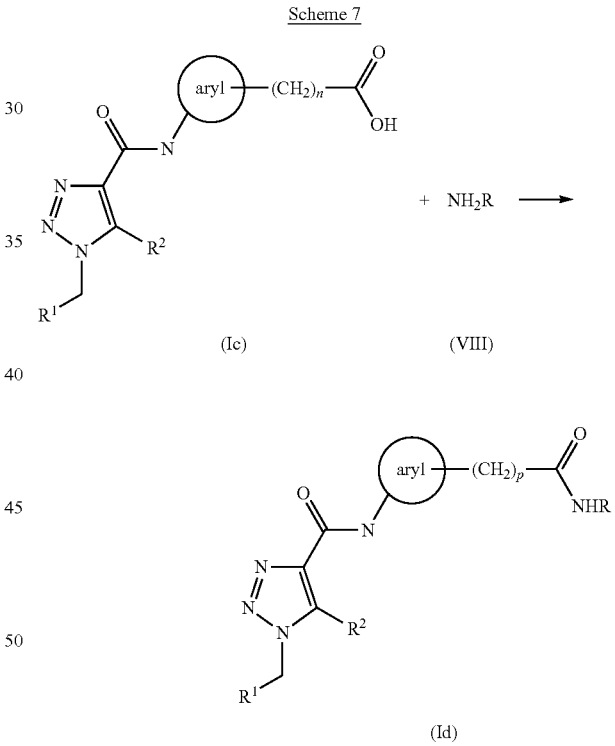

Accordingly, in another aspect the invention provides a process for the preparation of compounds of the formula (Id) by reacting compounds of formula (Ic), wherein $R^1$, $R^2$ and

are defined above, with compounds of formula (VIII) wherein R is defined above, in the presence of a coupling agent.

Compounds of formula (I), wherein $R^3$ represents

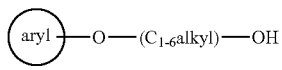

and

is defined above (formula (Ie)), may be prepared according to reaction scheme 8 by reacting compounds of formula (IX) and compounds of formula (II). The reaction is suitably carried out in the presence of a coupling reagent such as HATU and base such as DIPEA in a suitable solvent such as DMF (suitably at room temperature or at 40° C.), and is followed by deprotection of compounds of formula (X) with a of a concentrated HCl solution in AcOEt.

Compounds of formula (I), wherein $R^3$ represents

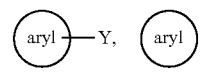

is defined above and Y represents branched —$C_{0-6}$alkylOH (such as —$C(CH)_3OH$) (formula (If)), may be prepared according to reaction scheme 9 by reacting compounds of formula (VII) in the presence of a solution of methyl magnesium bromide in THF (suitably at room temperature or at 60° C.).

Scheme 8

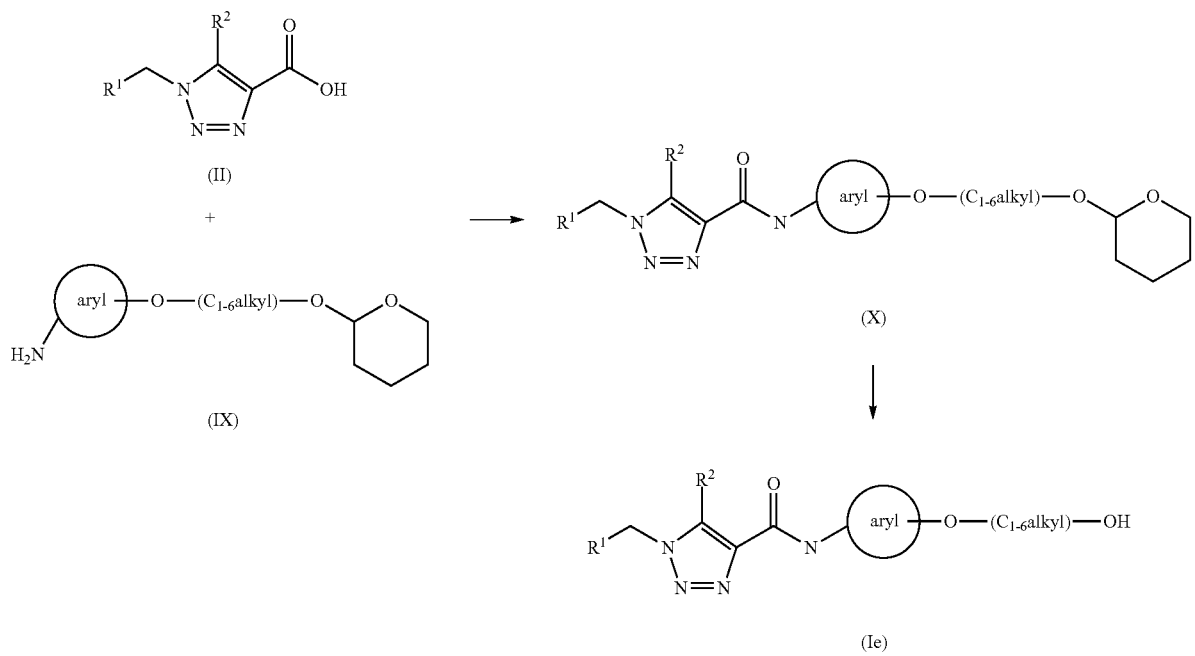

Accordingly, in another aspect the invention provides a process for the preparation of compounds of the formula (Ie) by reacting compounds of formula (II), wherein $R^1$ and $R^2$ are defined above, with compounds of formula (IX), wherein

is defined above, in the presence of a coupling agent, followed by the deprotection of compounds of formula (X).

Scheme 9

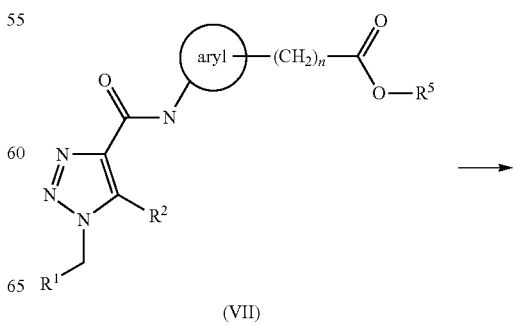

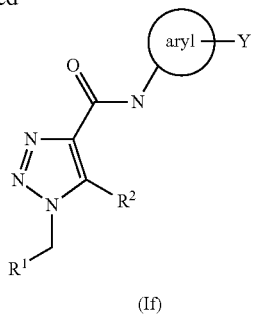

(If)

Accordingly, in another aspect the invention provides a process for the preparation of compounds of the formula (If), wherein

and Y are defined above, by reacting compounds of formula (VII), wherein $R^1$ and $R^2$ are defined above, in the presence of methyl magnesium bromide.

Compounds of formula (I), wherein $R^3$ represents

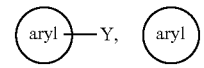

is defined above and Y represents —$C_{1-6}$alkenyl (formula (Ig)), may be prepared according to reaction scheme 10 by reacting compounds of formula (VII) in the presence of a solution of methyl magnesium bromide in THF (suitably at room temperature or at 60° C.).

Scheme 10

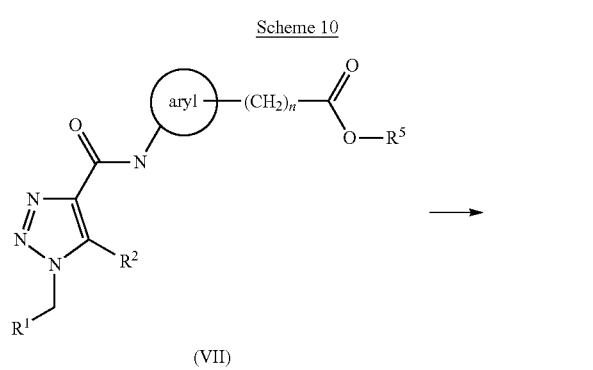

(VII)

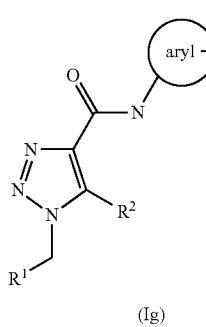

(Ig)

Accordingly, in another aspect the invention provides a process for the preparation of compounds of the formula (Ig), wherein

and Y are defined above, by reacting compounds of formula (VII), wherein $R^1$ and $R^2$ are defined above, in the presence of methyl magnesium bromide.

Compounds of formula (I), wherein $R^3$ represents

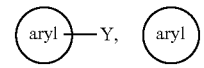

is defined above and Y represents —$(CH_2)_mOC(=O)R^4$ or —$(CH_2)_nOC(=O)R^5$ (formula (Ih)), may be prepared according to reaction scheme 11 by reaction of compounds of the formula (Ib) with compounds of the formula (XI), wherein R represents $R^4$ or $R^5$, in a suitable solvent such as a mixture of DCM and THF (suitably at suitable room temperature).

Scheme 11

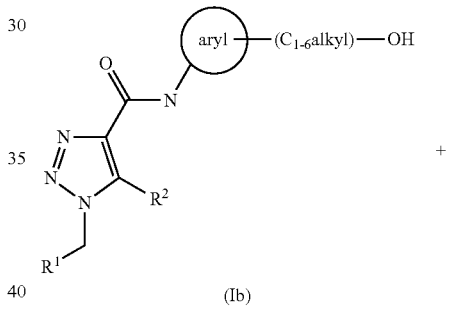

Accordingly, in another aspect the invention provides a process for the preparation of compounds of the formula (Ih), wherein

and Y are defined above, by reacting compounds of formula (Ib), wherein $R^1$ and $R^2$ are defined above, with compounds of the formula (XI), wherein R is defined above.

Compounds of formula (I), wherein X represents —NHCO— and $R^3$ represents wherein

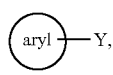

and Y are defined as above ((formula (Ii), may be prepared according to reaction scheme 12 by reacting compounds of formula (XII) and compounds of formula (XIII). The reaction is suitably carried out in the presence of a coupling reagent such as HATU and a base such as DIPEA in a suitable solvent such as DCM or DMF (suitably at room temperature to 40° C.).

Scheme 12

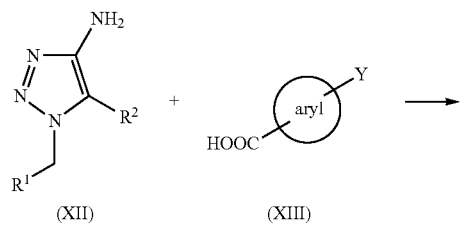

Accordingly, in another aspect the invention provides a process for the preparation of compounds of the formula (Ii) by reacting compounds of formula (XII), wherein $R^1$ and $R^2$ and $R^3$ represents

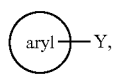

wherein

and Y are defined as above, with compounds of formula (XIII) wherein and Y are defined above, in the presence of a coupling reagent.

Compounds of formula (XII), wherein $R^1$ and $R^2$, are defined above may be prepared according to reaction scheme 13 by reacting compounds of formula (XIIa) in the presence of bromine and a base such as potassium hydroxide in a suitable solvent such as water (suitably at 40° to 80° C.).

Scheme 13

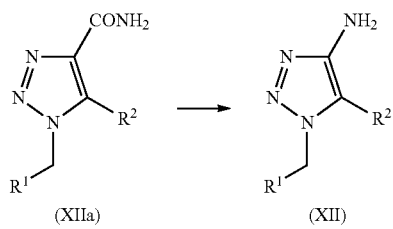

Compounds of formula (XIIa), wherein $R^1$ and $R^2$, are defined above may be prepared according to reaction scheme 14 by reacting compounds of formula (II), in the presence of thionyl chloride in chloroform at room temperature, followed by reaction with aqueous ammonia in acetonitrile on ice (e.g. −5 to 5° C.).

Scheme 14

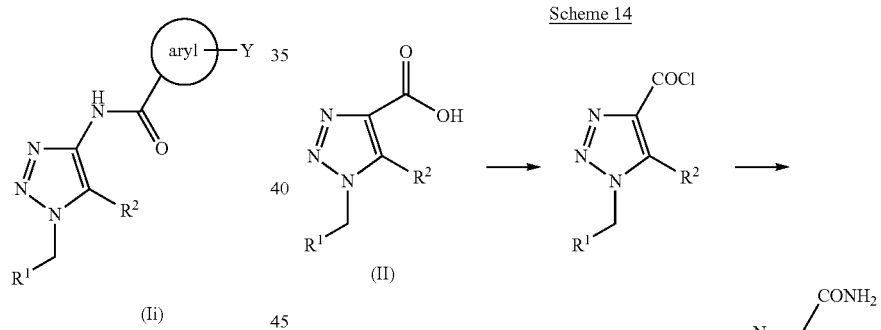

Compounds of the formula (III) (IVb), (VI), (VIII), (IX), (XI) and (XIII) are commercially available compounds or may be prepared by methods known in the literature or processes known to those skilled in the art. Compounds of the formula (VII) may be prepared according to the general reaction scheme 1.

Further details for the preparation of compounds of formula (I) are found in the examples section hereinafter.

The compounds of the invention may be prepared singly or as compound libraries comprising at least 2, for example 5 to 1,000 compounds, and more preferably 10 to 100 compounds. Libraries of compounds of the invention may be prepared by a combinatorial 'split and mix' approach or by multiple parallel syntheses using either solution phase or solid phase chemistry, by procedures known to those skilled in the art. Thus according to a further aspect there is provided a compound library comprising at least 2 compounds of the invention.

Those skilled in the art will appreciate that in the preparation of compounds of formula (I) and/or solvates thereof it may be necessary and/or desirable to protect one or more sensitive groups in the molecule or the appropriate intermediate to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl or aralkyl type protecting groups (e.g. benzyl, trityl, chlorotrityl).

Various intermediate compounds used in the above-mentioned process, including but not limited to certain compounds of formulae (IV), (V) and (X), constitute a further aspect of the present invention.

The compounds of formula (I) or pharmaceutically acceptable salt(s) thereof may also be used in combination with other therapeutic agents. The invention thus provides, in a further aspect, a combination comprising a compound of formula (I) or pharmaceutically acceptable salts thereof together with one or more further therapeutic agent(s).

Compounds of the invention may be administered in combination with other therapeutic agents. Preferred therapeutic agents are selected from the list: an inhibitor of cholesteryl ester transferase (CETP inhibitors), a HMG-CoA reductase inhibitor, a microsomal triglyceride transfer protein, a peroxisome proliferator-activated receptor activator (PPAR), a bile acid reuptake inhibitor, a cholesterol absorption inhibitor, a cholesterol synthesis inhibitor, a fibrate, niacin, an ion-exchange resin, an antioxidant, an inhibitor of AcylCoA: cholesterol acyltransferase (ACAT inhibitor), a cannabinoid 1 antagonist a bile acid sequestrant. Other preferred therapeutic agents are selected from the list: a corticosteroid, a vitamin D3 derivative, a retinoid, an immunomodulator, an anti androgen, a keratolytic agent, an anti-microbial, a platinum chemotherapeutic, an antimetabolite, hydroxyurea, a taxane, a mitotic disrupter, an anthracycline, dactinomycin, an alkylating agent and a cholinesterase inhibitor.

When the compound of formula (I) or pharmaceutically acceptable salt thereof is used in combination with a second therapeutic agent the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The combinations referred to above may conveniently be presented for use in the form of a pharmaceutical formulation and thus pharmaceutical formulations comprising a combination as defined above together with at least one pharmaceutically acceptable carrier and/or excipient comprise a further aspect of the invention. The individual components of such combinations may be administered either sequentially or simultaneously in separate or combined pharmaceutical formulations by any convenient route.

When administration is sequential, either the SCD inhibitor or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The invention also includes a pharmaceutical composition comprising one or more compounds of formula (I) or pharmaceutically acceptable salt (s) in combination with one or more excipients.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

Creams, lotions, or ointments, may be prepared as rinse-off or leave-on products, as well as two stage treatment products for use with other skin cleansing or managing compositions. The compositions can be administered as a rinse-off product in a higher concentration form, such as a gel, and then a leave-on product in a lower concentration to avoid irritation of the skin. Each of these forms is well understood by those of ordinary skill in the art, such that dosages may be easily prepared to incorporate the pharmaceutical composition of the invention.

Ointments are hydrocarbon-based semisolid formulations containing dissolved or suspended drugs. Creams and lotions are semi-solid emulsion systems and the term is applied both to water/oil or oil/water. Gel formulations are semi-solid systems in which a liquid phase is trapped in a polymeric matrix.

By way of non-limiting example, the ointments may contain one or more hydrophobic carriers selected from, for example, white soft paraffin or other mineral waxes, liquid paraffin, non-mineral waxes, long chain alcohols, long chain acids and silicones. The ointment may contain in addition to the hydrophobic carriers some hydrophillic carriers selected from, for example, propylene glycol and polyethylene glycol in combination with an appropriate surfactant/co-surfactant system. The carrier compositions of the creams or lotions are typically based on water, white soft paraffin and an appropriate surfactant/co-surfactant system, in combination with other carriers/components selected from, for example, propylene glycol, butylene glycol glycerinemonostearate, PEG-glycerinemonostearate, esters such as $C_{12-15}$ alkyl benzoate, liquid paraffin, non-mineral waxes, long chain alcohols, long chain acids silicones, non-silicone polymers. The gels may by way of example be formulated using isopropyl alcohol or ethyl alcohol, propylene glycol and water with a gelling agent such as hydroxyethyl cellulose, suitably in combination with minor components, for example one or more of butylene glycol and a wetting agent such as a poloxamer.

An ointment, cream, lotion, gel, and the like, can further comprise a moisturizing agent. The moisturizing agent can be a hydrophobic moisturizing agent such as ceramide, borage oil, tocopherol, tocopherol linoleate, dimethicone or a mixture thereof or a hydrophilic moisturizing agent such as glycerine, hyaluronic acid, sodium peroxylinecarbolic acid, wheat protein, hair keratin amino acids, or a mixture thereof.

The compositions according to the invention may also comprise conventional additives and adjuvants for dermatological applications, such as preservatives, acids or bases used as pH buffer excipients and antioxidants.

The present invention encompasses administration via a transdermal patch or other forms of transdermal administration. Suitable formulations for transdermal administration are known in the art, and may be employed in the methods of the present invention. For example, suitable transdermal patch formulations for the administration of a pharmaceutical compound are described in, for example, U.S. Pat. No. 4,460,372 to Campbell et al., U.S. Pat. No. 4,573,996 to Kwiatek et al., U.S. Pat. No. 4,624,665 to Nuwayser, U.S. Pat. No. 4,722,941 to Eckert et al., and U.S. Pat. No. 5,223,261 to Nelson et al.

One suitable type of transdermal patch for use in the methods of the present invention encompasses a suitable transdermal patch includes a backing layer which is non-permeable, a permeable surface layer, an adhesive layer substantially continuously coating the permeable surface layer, and a reservoir located or sandwiched between the backing layer and the permeable surface layer such that the backing layer extends around the sides of the reservoir and is joined to the permeable surface layer at the edges of the permeable surface layer. The reservoir contains a compound of formula (I) or pharmaceutically acceptable salt thereof, alone or in combination, and is in fluid contact with the permeable surface layer. The transdermal patch is adhered to the skin by the adhesive layer on the permeable surface layer, such that the permeable surface layer is in substantially continuous contact with the skin when the transdermal patch is adhered to the skin. While the transdermal patch is adhered to the skin of the subject, the compound of formula (I) or pharmaceutically acceptable salt thereof contained in the reservoir of the transdermal patch is transferred via the permeable surface layer, from the reservoir, through the adhesive layer, and to the skin of the patient. The transdermal patch may optionally also include one or more penetration-enhancing agents in the reservoir that enhance the penetration of the compound of formula (I) or pharmaceutically acceptable salt thereof through the skin.

Examples of suitable materials which may comprise the backing layer are well known in the art of transdermal patch delivery, and any conventional backing layer material may be employed in the transdermal patch of the instant invention.

Suitable penetration-enhancing agents are well known in the art as well. Examples of conventional penetration-enhancing agents include alkanols such as ethanol, hexanol, cyclohexanol, and the like, hydrocarbons such as hexane, cyclohexaue, isopropylbenzene; aldehydes and ketones such as cyclohexanone, acetamide, N,N-di(lower alkyl)acetamides such as N,N-diethylacetamide, N,N-dimethyl acetamide, N-(2-hydroxyethyl) acetamide, esters such as N,N-di-lower alkyl sulfoxides; essential oils such as propylene glycol, glycerine, glycerol monolaurate, isopropyl myristate, and ethyl oleate, salicylates, and mixtures of any of the above.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Preparations for oral administration may be suitably formulated to give controlled/extended release of the active compound.

Suppositories will contain conventional suppository bases, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active ingredient, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

The invention also extends to novel intermediates disclosed herein, used in the preparation of compounds of formula (I) or salts thereof.

The following is a list of the used definitions:

DEFINITIONS

APTS para toluene sulfonic acid
AcOEt ethyl acetate
DCM dichloromethane
DIBAL-H diisobutylaluminium hydride solution
DIPEA diisopropylethylamine
DME 1,2-dimethoxy ethane
DMF dimethylformamide
DMSO dimethyl sulfoxyde
EDCl 1,3-Propanediamine, N3-(ethylcarbonimidoyl)-N1, N1-dimethyl-, hydrochloride
$NEt_3$ triethylamine
EtOH ethanol
HATU O-(7-Azabenzotriazol-1-yl)-1,1,3,3-tetramethyluronium hexafluorophosphate
HCl hydrochloric acid
HOBt 1-hydroxy benzotriazole
NaOH sodium hydroxide
$NH_4Cl$ ammonium chloride
$PBr_3$ phosphorus tribromine
Pd tetrakis tetrakis(triphenylphosphine)palladium (0)
Pd/C palladium (0) on carbon
RT room temperature
THF tetrahydrofuran Regardless of how the preparation of compounds are represented in the present specification no inference can be drawn that particular batches (or mixtures of two or more batches) of intermediates were used in the next stage of the preparation. The examples and intermediates are intended to illustrate the synthetic routes suitable for preparation of the same, to assist the skilled persons understanding of the present invention.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

Analytical Methods LC-MS

Analytical HPLC was conducted on a X-terra MS C18 column (2.5 µm 3*30 mm id) eluting with 0.01M ammonium acetate in water (solvent A) and 100% acetonitrile using the following elution gradient: 0 to 4 minutes, 5 to 100% B; 4 to 5 minutes, 100% B at a flowrate of 1.1 mL/min with a temperature of 40° C.

The mass spectra (MS) were recorded on a micromass ZQ-LC mass spectrometer using electrospray positive ionisation [ES+ve to give $MH^+$ molecular ion] or electrospray negative ionisation [ES−ve to give $(M-H)^-$ molecular ion] modes.

Analytical Methods LC-HRMS

Analytical HPLC was conducted on an Uptisphere-hsc column (3 µm 30*3 mm id) eluting with 0.01M ammonium acetate in water (solvent A) and 100% acetonitrile (solvent B) using the following elution gradient: 0 to 0.5 minutes, 5% B; 0.5 to 3.5 minutes, 5 to 100% B; 3.5 to 4 minutes, 100% B; 4 to 4.5 minutes, 100 to 5% B; 4.5 to 5.5 minutes, 5% B at a flowrate of 1.3 mL/min with a temperature of 40° C.

The mass spectra (MS) were recorded on a micromass LCT, mass spectrometer using electrospray positive ionisation [ES+ve to give $MH^+$ molecular ion] or electrospray negative ionisation [ES−ve to give $(M-H)^-$ molecular ion] modes.

Analytical Method GC-MS

Analytical GC was conducted on a DB-1 ms column (Agilent Technologies), 0.1 µm 10 m*0.1 mm id) eluting with an Helium flow of 0.5 ml/min and pressure at 3.4 bar and with a gradient temperature: 0 to 0.35 min, 100° C.; 0.35 min to 6 min, 100° C. to 250° C. (ramp of 80° C./min).

The mass spectra (MS) were recorded on a Agilent Technologies G5973 mass spectrometer using electronic impact ionisation.

SUPPORTING EXAMPLES AND INTERMEDIATES

The invention is illustrated by the non-limiting Examples described below.

Intermediate 1

1-[(2'-Chloro-4-biphenylyl)methyl]-5-methyl-1H-1, 2,3-triazole-4-carboxylic acid

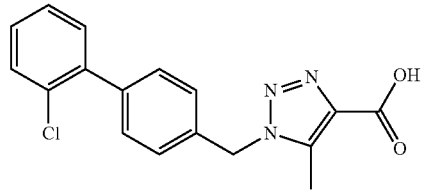 [SMILES: Cc1c(C(=O)O)nnn1Cc1ccc(-c2ccccc2Cl)cc1]

To a solution of 1-[(4-bromophenyl)methyl]-5-methyl-1H-1,2,3-triazole-4-carboxylic acid (0.2 g, 0.67 mmol) in DME (10 mL) were added (2-chlorophenyl)boronic acid, (0.137 g, 0.88 mmol), Pd tetrakis (20 mg, 10% mol/mol) and a 2M solution of sodium carbonate (1.34 mL, 4 eq). The reaction was heated at 85° C. for 48 hours. After evaporation of DME, water was added and the reaction was extracted with ethyl acetate (2×40 mL). The aqueous phase was adjusted to PH=7 by addition of a 1N HCl solution and extracted with ethyl acetate. The combined organic phases were dried over sodium sulphate and evaporated in vacuo to give the title compound as a solid (117 mg, 40%). HRMS calculated for $C_{17}H_{14}ClN_3O_2(M+H)^+$ 328.0853. found: 328.0865, Rt: 2.04 min.

Intermediate 2

2-Biphenylylmethyl azide

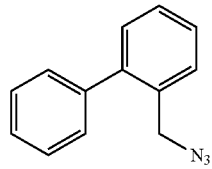 [SMILES: [N-]=[N+]=NCc1ccccc1-c1ccccc1]

To a solution of 2-(bromomethyl)biphenyl (1.5 g, 6 mmol) in DMSO (15 mL) was added sodium azide (0.59 g, 9 mmol) and a catalytic amount of sodium iodide. The mixture was stirred at room temperature for 2 days. After concentration under reduced pressure, the residue was diluted with ethyl acetate. The organic layer was washed with brine (2×60 mL), dried on sodium sulphate and after filtration was evaporated to dryness to give the title compound as an oil (1.1 g, 87%). $^1$H NMR (300 MHz, CDCl$_3$, ppm) δ: 7.56-7.38 (m, 9H), 4.37 (s, 2H).

Intermediate 3

(3,4-Dichlorophenyl)methyl azide

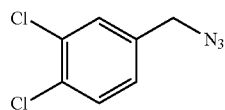

A mixture of 3,4-dichlorobenzyl chloride (10 g, 0.05 mol), sodium azide (5 g, 0.08 mol) in DMSO (100 mL) was stirred at room temperature overnight. The mixture was poured into water (150 mL). The water layer was extracted with ethyl acetate (100 ml×3). The combined organic phases were dried over sodium sulfate, filtered and concentrated in vacuo. The residue was purified by distillation to give the title compound as an oil (14 g, quantitative yield). LC/MS: m/z 203 (M+H)$^+$, Rt: 2.26 min.

The following compounds were similarly prepared by a method analogous to that described for Intermediate 3:

TABLE 1

| Compound | Structure | From | Physical data |
|---|---|---|---|
| Intermediate 4 (3,5-Diclorophenyl) methyl azide | 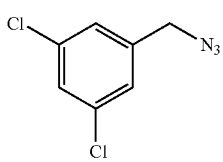 [SMILES: [N-]=[N+]=NCc1cc(Cl)cc(Cl)c1] | 3,4-dichlorobenzyl chloride | Not isolated |
| Interrmediate 5 (3-Chlorophenyl) methyl azide | | 3-chlorobenzyl bromide | LC/MS: m/z 168 (M + H)$^+$, Rt: 2.54 min |

Intermediate 6

Methyl 1-(2-biphenylylmethyl)-5-methyl-1H-1,2,3-triazole-4-carboxylate

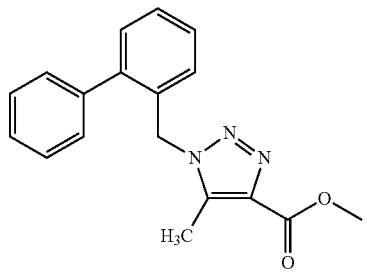 [SMILES: COC(=O)c1nnn(Cc2ccccc2-c2ccccc2)c1C]

To a solution of 2-biphenylylmethyl azide (Intermediate 2) (1.1 g, 5.2 mmol) and methyl acetoacetate (0.9 g, 7.8 mmol) in DMSO (10 mL) was added potassium carbonate (2.9 g, 20 mmol). The reaction mixture was stirred at 40° C. for 48 hours. After cooling, water was added and the mixture was extracted with ethyl acetate, the organic layer was dried on sodium sulphate and after filtration was evaporated to dryness. The residue was purified by flash column chromatography eluting with DCM and DCM/MeOH: 98/2 to give the title compound as an oil (1.1 g, 68.7%). LC/MS: m/z 308 (M+H)$^+$, Rt: 3.14 min.

Intermediate 7

Methyl 1-[(3,4-dichlorophenyl)methyl]-5-methyl-1H-1,2,3-triazole-4-carboxylate

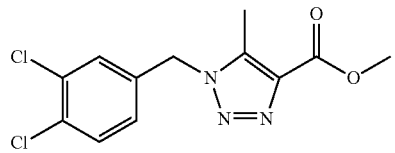 [SMILES: COC(=O)c1nnn(Cc2ccc(Cl)c(Cl)c2)c1C]

To a suspension of milled potassium carbonate (38.7 g, 0.28 mol) in DMSO (100 mL) was added (3,4-dichlorophenyl)methyl azide (Intermediate 3) (14 g, 0.07 mol) and methyl acetoacetate (12.1 g, 0.1 mol). The mixture was stirred at 40° C. for 48 hours. The mixture was poured into a mixture of ice and water (100 mL). The water was extracted with ethyl acetate (100 mL×2). The combined organic phases were dried over sodium sulfate, filtered and concentrated. The residue was purified by distillation to give the title compound as white solid crystals (14 g, 67%). LC/MS: m/z 301 (M+H)$^+$, Rt: 1.97 min.

The following compounds were similarly prepared by a method analogous to that described for Intermediate 7:

TABLE 2

| Compound | Structure | From | Physical data |
|---|---|---|---|
| Intermediate 8 Methyl 1-[(3,5-dichlorophenyl)methyl]-5-methyl-1H-1,2,3-triazole-4-carboxylate | 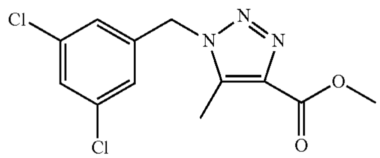 [SMILES: COC(=O)c1nnn(Cc2cc(Cl)cc(Cl)c2)c1C] | (3,5-dichlorophenyl) methyl azide (Intermediate 4) | LC/MS: m/z 300 (M + H)+, Rt: 3.01 min |
| Intermediate 9 Methyl 1-[(3-chlorophenyl)methyl]-5-methyl-1H-1,2,3-triazole-4-carboxylate | 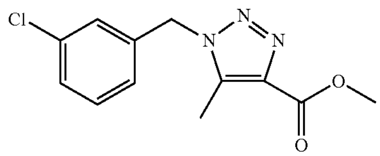 [SMILES: COC(=O)c1nnn(Cc2cccc(Cl)c2)c1C] | (3-chlorophenyl) methyl azide (Intermediate 5) | 1H NMR (300 MHz, DMSO, ppm) δ: 7.39 (dd, 2H), 7.3 (s, 1H) 5.65 (s, 2H), 3.81 (s, 3H), 2.46 (s, 3H). |

Intermediate 10

1-(2-Biphenylylmethyl)-5-methyl-1H-1,2,3-triazole-4-carboxylic acid

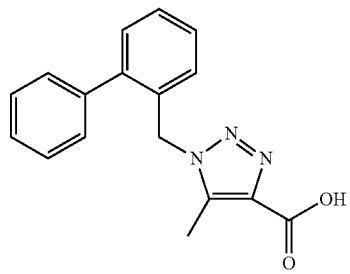 [SMILES: Cc1c(C(=O)O)nnn1Cc1ccccc1-c1ccccc1]

To a solution of methyl 1-(2-biphenylylmethyl)-5-methyl-1H-1,2,3-triazole-4-carboxylate (Intermediate 6) (1.1 g, 3.58 mmol) in methanol was added an aqueous solution of sodium hydroxide (7.2 mL, 6 mmol). The solution was heated at reflux for 3 hours. After concentration under reduced pressure, a 1N HCl solution (8 mL) was added. The resulting solid material was filtered, washed with water and dried to give the title compound as a cream solid (810 mg, 77%). LC/MS: m/z 294 (M+H)+, Rt: 2.23 min.

Intermediate 11

1-[(3,4-Dichlorophenyl)methyl]-5-methyl-1H-1,2,3-triazole-4-carboxylic acid

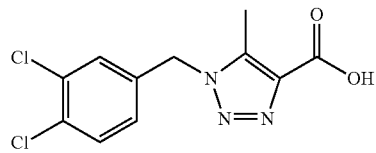 [SMILES: Cc1c(C(=O)O)nnn1Cc1ccc(Cl)c(Cl)c1]

To a mixture of methyl 1-[(3,4-dichlorophenyl)methyl]-5-methyl-1H-1,2,3-triazole-4-carboxylate (Intermediate 7) (9 g, 0.03 mol) in methanol (200 mL) was added NaOH (2.4 g) and water. The mixture was stirred overnight. Water was added and the solvent was evaporated. The residue was extracted with DCM (twice). The aqueous phase was adjusted to pH=2 with a 2N HCl solution. The formed precipitate was filtered to give the title compound as a white solid (7.29 g, 84%). LC/MS: m/z 287 (M+H)+, Rt: 2.52 min.

The following compounds were similarly prepared by a method analogous to that described for Intermediate 11:

TABLE 3

| Compound | Structure | From | Physical data |
|---|---|---|---|
| Intermediate 12 1-[(3,5-Dichlorophenyl)methyl]-5-methyl-1H-1,2,3-triazole-4-carboxylic acid | 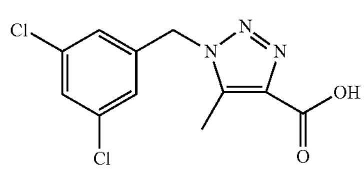 [SMILES: Cc1c(C(=O)O)nnn1Cc1cc(Cl)cc(Cl)c1] | Methyl 1-[(3,5-dichlorophenyl)methyl]-5-methyl-1H-1,2,3-triazole-4-carboxylate (Intermediate 8) | LC/MS: m/z 286 (M + H)+, Rt: 2.22 min |
| Intermediate 13 1-[(3-Chlorophenyl)methyl]-5-methyl-1H-1,2,3-triazole-4-carboxylic acid | 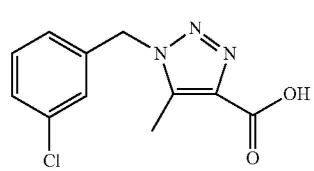 [SMILES: Cc1c(C(=O)O)nnn1Cc1cccc(Cl)c1] | Methyl 1-[(3-chlorophenyl)methyl]-5-methyl-1H-1,2,3-triazole-4-carboxylate (Intermediate 9) | 1H NMR (300 MHz, DMSO, ppm) δ: 7.37-7.27 (dd, 2H), 7.11 (s, 1H) 5.63 (s, 2H), 2.44 (s, 3H). |

Intermediate 14

Dimethyl 5[({1-[(3,4-dichlorophenyl)methyl]-5-methyl-1H-1,2,3-triazol-4-yl}carbonyl)amino]-1,3-benzenedicarboxylate

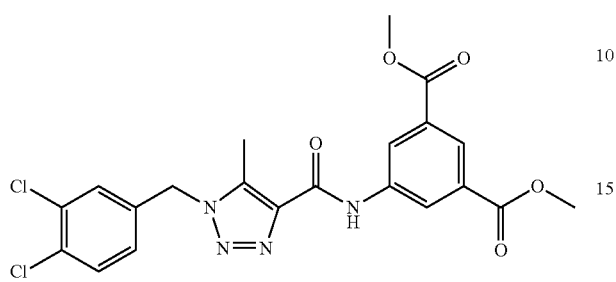

A mixture of 1-[(3,4-dichlorophenyl)methyl]-5-methyl-1H-1,2,3-triazole-4-carboxylic acid (Intermediate 11) (0.4 g, 1.3 mmol), dimethyl 5-amino-1,3-benzenedicarboxylate (0.29 g, 1 eq), HATU (0.69 g, 1.3 eq) and DIPEA (0.34 mL, 1.3 eq) in DMF (10 mL) was stirred at 45° C. for 24 hours. The solvent was evaporated and the residue was washed with water and extracted with DCM. The organic phase was dried over sodium sulphate and concentrated. The title compound was obtained as a white solid (650 mg, 95%) after recrystallisation from acetonitrile. LC/MS: m/z 477 (M+H)$^+$, Rt: 3.81 min.

The following compounds were similarly prepared by a method analogous to that described for Intermediate 14:

Intermediate 17

2-({2-[(4-Nitrophenyl)oxy]ethyl}oxy)tetrahydro-2H-pyran

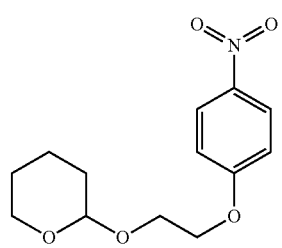

To a solution of 2-[(4-Nitrophenyl)oxy]ethanol (1 g, 5.4 mmol), in toluene (50 mL) was added 3,4-dihydro-2H-pyran (1.5 mL) and APTS (catalytic amount). The reaction was stirred at 60° C. for 3 hours. The dark solution was then concentrated and purified by flash chromatography using DCM/cyclohexane 30/70 as eluent. The title compound was obtained as an oil (1.33 g, 92%). LC: Rt: 3.12 min.

TABLE 4

| Compound | Structure | From | Physical data |
|---|---|---|---|
| Intermediate 15 Dimethyl 5-({[5-methyl-1-(phenylmethyl)-1H-1,2,3-triazol-4-yl]carbonyl}amino)-1,3-benzenedicarboxylate | 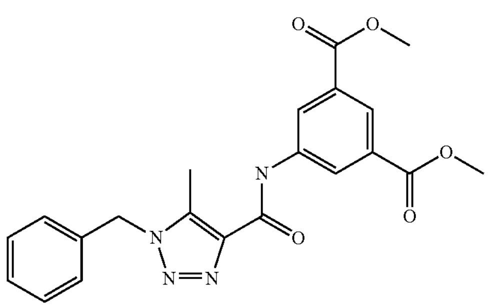 [SMILES: COC(=O)c1cc(NC(=O)c2nnn(Cc3ccccc3)c2C)cc(C(=O)OC)c1] | 5-methyl-1-(phenylmethyl)-1H-1,2,3-triazole-4-carboxylic acid and dimethyl 5-amino-1,3-benzene dicarboxylate | LC/MS: m/z 409 (M + H)$^+$, Rt: 3.34 min |
| Intermediate 16 Dimethyl 5-[({1-[(3-chlorophenyl)methyl]-5-methyl-1H-1,2,3-triazol-4-yl}carbonyl)amino]-1,3-benzenedicarboxylate | 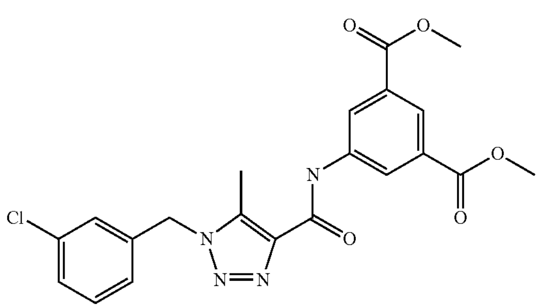 [SMILES: COC(=O)c1cc(NC(=O)c2nnn(Cc3cccc(Cl)c3)c2C)cc(C(=O)OC)c1] | 1-[(3-Chlorophenyl)methyl]-5-methyl-1H-1,2,3-triazole-4-carboxylic acid (Intermediate 13) and dimethyl 5-amino-1,3-benzene dicarboxylate | LC/MS: m/z 443 (M + H)$^+$, Rt: 3.54 min |

Intermediate 18

4-{[2-(Tetrahydro-2H-pyran-2-yloxy)ethyl]oxy}aniline

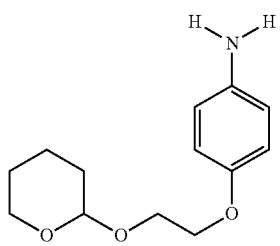 [SMILES: Nc1ccc(OCCOC2CCCCO2)cc1]

To a solution of 2-({2-[(4-nitrophenyl)oxy]ethyl}oxy)tetrahydro-2H-pyran (Intermediate 17) (1.33 g, 5 mmol) in EtOH (50 mL) was added Pd/C (catalytic amount) and ammonium formate (0.9 g, 10 eq). The reaction was stirred to 40° C. for 2 hours. After filtration on celite, the solvent was evaporated and the residue was poured in water, extracted with ether and dried over sodium sulphate and evaporated. The title compound was obtained as a dark oil (0.8 g, 68%). LC/MS: m/z 238 (M+H)+, Rt: 2.38 min.

Intermediate 19

1-[(3,4-Dichlorophenyl)methyl]-5-methyl-N-(4-{[2-(tetrahydro-2H-pyran-2-yloxy)ethyl]oxy}phenyl)-1H-1,2,3-triazole-4-carboxamide

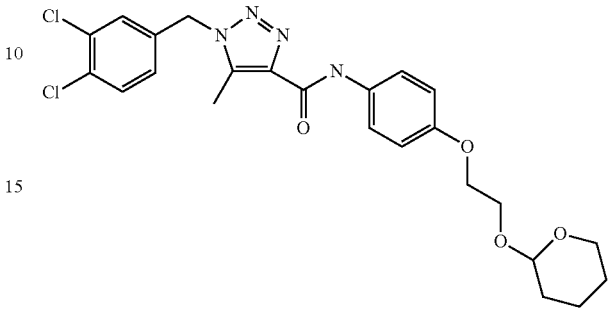

A mixture of 1-[(3,4-dichlorophenyl)methyl]-5-methyl-1H-1,2,3-triazole-4-carboxylic acid (Intermediate 11) (0.3 g, 1 mmol), 4-{[2-(tetrahydro-2H-pyran-2-yloxy)ethyl]oxy}aniline (Intermediate 18) (0.28 g, 1.2 eq), HATU (0.8 g, 2 eq), and NEt₃ (440 μL, 3 eq) in DMF was stirred at 45° C. for 18 hours. The solvent was evaporated and the residue was washed with water and extracted with a mixture of ether and ethyl acetate. The organic phase was dried over sodium sulfate, filtered and concentrated in vacuo. The title compound was obtained and used in the next step without purification and isolation.

The following compounds were similarly prepared by a method analogous to that described for Intermediate 14:

TABLE 5

| Compound | Structure | From | Physical data |
|---|---|---|---|
| Intermediate 20 Dimethyl 4-({[5-methyl-1-(phenylmethyl)-1H-1,2,3-triazol-4-yl]carbonyl}amino)-1,2-benzenedicarboxylate | 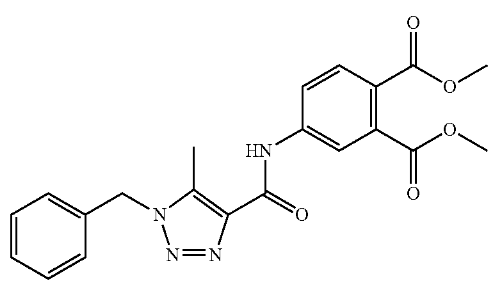 [SMILES: COC(=O)c1ccc(NC(=O)c2nnn(Cc3ccccc3)c2C)cc1C(=O)OC] | 5-methyl-1-(phenylmethyl)-1H-1,2,3-triazole-4-carboxylic acid and dimethyl 4-amino-1,2-benzenedicarboxylate | LC/MS: m/z 407 (M − H)+, Rt: 2.74 min |
| Intermediate 21 Dimethyl 5-[({1-[(4-fluorophenyl)methyl]-5-methyl-1H-1,2,3-triazol-4-yl}carbonyl)amino]-1,3-benzenedicarboxylate | 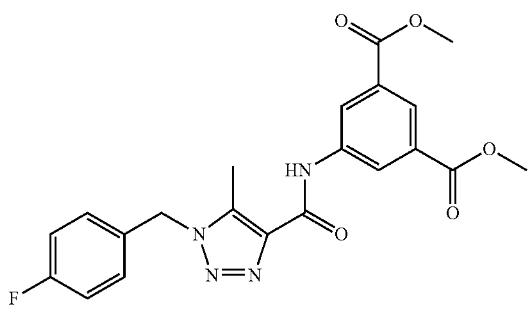 [SMILES: COC(=O)c1cc(NC(=O)c2nnn(Cc3ccc(F)cc3)c2C)cc(C(=O)OC)c1] | 1-[(4-fluorophenyl)methyl]-5-methyl-1H-1,2,3-triazole-4-carboxylic acid and dimethyl 5-amino-1,3-benzenedicarboxylate | LC/MS: m/z 427 (M + H)+, Rt: 3.44 min |

TABLE 5-continued

| Compound | Structure | From | Physical data |
|---|---|---|---|
| Intermediate 22 Dimethyl 4-[({1-[(3-chlorophenyl)methyl]-5-methyl-1H-1,2,3-triazol-4-yl}carbonyl)amino]-1,2-benzenedicarboxylate | 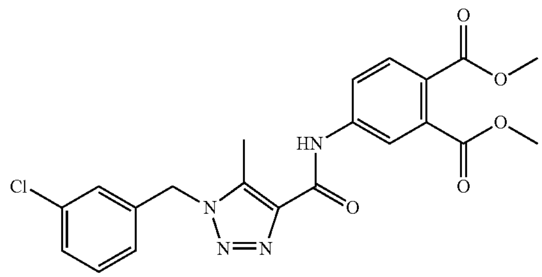 [SMILES: COC(=O)c1ccc(NC(=O)c2nnn(Cc3cccc(Cl)c3)c2C)cc1C(=O)OC] | 1-[(3-chlorophenyl)methyl]-5-methyl-1H-1,2,3-triazole-4-carboxylic acid (Intermediate 13) and dimethyl 4-amino-1,2-benzenedicarboxylate | LC/MS: m/z 443 (M + H)+, Rt: 3.36 min |
| Intermediate 23 Dimethyl 4-[({1-[(4-fluorophenyl)methyl]-5-methyl-1H-1,2,3-triazol-4-yl}carbonyl)amino]-1,2-benzenedicarboxylate | | 1-[(4-fluorophenyl)methyl]-5-methyl-1H-1,2,3-triazole-4-carboxylic acid and dimethyl 4-amino-1,2-benzenedicarboxylate | LC/MS: m/z 427 (M + H)+, Rt: 3.22 min |

The following compound was similarly prepared by a method analogous to that described for Intermediate 3:

TABLE 6

| Compound | Structure | From | Physical data |
|---|---|---|---|
| Intermedieate 24 (3-fluorophenyl) methyl azide | 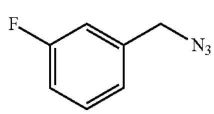 [SMILES: [N-]=[N+]=NCc1cccc(F)c1] | 3-fluorobenzyl bromide | Not isolated |

The following compound was similarly prepared by a method analogous to that described for Intermediate 7:

TABLE 7

| Compound | Structure | From | Physical data |
|---|---|---|---|
| Intermediate 25 Methyl 1-[(3-fluorophenyl)methyl]-5-methyl-1H-1,2,3-triazole-4-carboxylate | 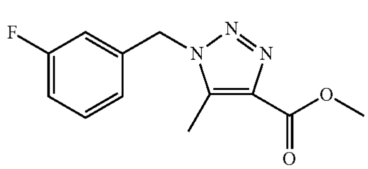 [SMILES: COC(=O)c1nnn(Cc2cccc(F)c2)c1C] | (3-fluorophenyl) methyl azide (Intermediate 24) | LC/MS: m/z 250 (M + H)+, Rt: 2.61 min |

The following compound was similarly prepared by a method analogous to that described for Intermediate 11:

TABLE 8

| Compound | Structure | From | Physical data |
|---|---|---|---|
| Intermediate 26 1-[(3-Fluorophenyl)methyl]-5-methyl-1H-1,2,3-triazole-4-carboxylic acid | 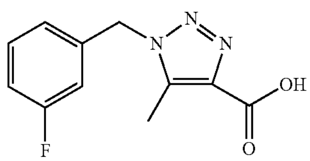 [SMILES: Cc1c(C(=O)O)nnn1Cc1cccc(F)c1] | methyl 1-[(3-fluorophenyl)methyl]-5-methyl-1H-1,2,3-triazole-4-carboxylate (Intermediate 25) | LC/MS: m/z 236 (M + H)+, Rt: 1.56 min |

The following compounds were similarly prepared by a method analogous to that described for Intermediate 14

TABLE 9

| Compound | Structure | From | Physical data |
|---|---|---|---|
| Intermediate 27 Dimethyl 5-[({1-[(3-fluorophenyl)methyl]-5-methyl-1H-1,2,3-triazol-4-yl}carbonyl)amino]-1,3-benzenedicarboxylate | 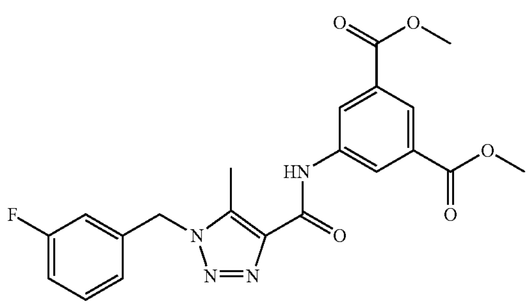 [SMILES: COC(=O)c1cc(NC(=O)c2nnn(Cc3cccc(F)c3)c2C)cc(C(=O)OC)c1] | 1-[(3-fluorophenyl)methyl]-5-methyl-1H-1,2,3-triazole-4-carboxylic acid (Intermediate 26) and dimethyl 5-amino-1,3-benzenedicarboxylate | LC/MS: m/z 427 (M + H)+, Rt: 3.35 min |
| Intermediate 28 Dimethyl 4-[({1-[(3-fluorophenyl)methyl]-5-methyl-1H-1,2,3-triazol-4-yl}carbonyl)amino]-1,2-benzenedicarboxylate | 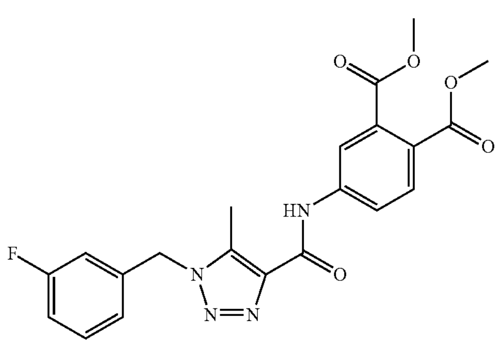 [SMILES: COC(=O)c1ccc(NC(=O)c2nnn(Cc3cccc(F)c3)c2C)cc1C(=O)OC] | 1-[(3-fluorophenyl)methyl]-5-methyl-1H-1,2,3-triazole-4-carboxylic acid (Intermediate 26) and dimethyl 5-amino-1,2-benzenedicarboxylate | LC/MS: m/z 427 (M + H)+, Rt: 3.21 min |

The following compound was similarly prepared by a method analogous to that described for Intermediate 19:

TABLE 10

| Compound | Structure | From | Physical data |
|---|---|---|---|
| Intermediate 29 Methyl 3-[(methylamino) carbonyl]-5-nitrobenzoate | 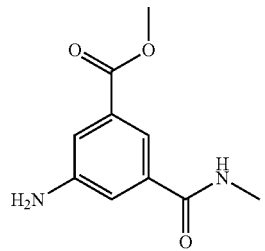 | 3-[(methyloxy) carbonyl]-5-nitrobenzoic acid and methylamine | LC/MS: m/z 239 $(M + H)^+$, Rt: 2.26 min |

Intermediate 30

Methyl 3-amino-5-[(methylamino)carbonyl]benzoate

To a solution of methyl 3-[(methylamino)carbonyl]-5-nitrobenzoate (Intermediate 29) (1.33 g, 5.59 mmol), in ethanol (30 mL) were added ammonium formiate (3.52 g, 1 eq.) and Pd/C (catalytic quantity). The reaction was stirred at 40° C. for one night. After filtration on celite, the solvent was evaporated in vacuo. The residue was dissolved in DCM, washed with water, dried over sodium sulfate and concentrated to give the title compound as a white solid (0.56 g, 48.3%). LC/MS: m/z 209 $(M+H)^+$, Rt: 1.50 min.

The following compound was similarly prepared by a method analogous to that described for Intermediate 14

Intermediate 32

1-[(3,4-Dichlorophenyl)methyl]-5-methyl-1H-1,2,3-triazole-4-carboxamide

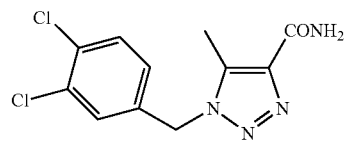 [SMILES: Cc1c(C(N)=O)nnn1Cc1ccc(Cl)c(Cl)c1]

To a solution of (1-[(3,4-Dichlorophenyl)methyl]-5-methyl-1H-1,2,3-triazole-4-carboxylic acid) (Intermediate 11) (14 g, 48.93 mmol), in chloroform (200 mL) was added thionyl chloride (30 mL) at room temperature. The reaction mixture was stirred to reflux for 4 hours and concentrated in vacuum. The mixture was then dissolved in acetonitrile (50 mL) and aqueous ammonia (50 mL) was added at 0° C. for 30 min. The resulting solid was filtered and dried to give the title compound as white crystals. (12.7 g, 91.1%). LC/MS: m/z 285 $(M+H)^+$, Rt: 2.53 min.

Intermediate 33

1-[(3,4-Dichlorophenyl)methyl]-5-methyl-1H-1,2,3-triazol-4-amine

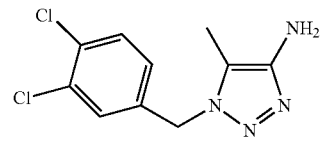 [SMILES: Cc1c(N)nnn1Cc1ccc(Cl)c(Cl)c1]

To a solution of potassium hydroxide (10.96 g, 195.8 mmol) in water (50 mL), cooled in an ice-salt bath, was added bromine (6.3 g, 32.16 mmol) and at 0° C., 1-[(3,4-dichlorophenyl)methyl]-5-methyl-1H-1,2,3-triazole-4-carboxamide (Intermediate 32) (9.3 g, 32.63 mmol) was added for 4 hours under vigorous stirring. The reaction mixture was then warmed at 80° C. for 2 days and stirred at room temperature for 12 hours. The resulting solid was filtered and purified by HPLC to give the title compound (3.45 g, 41.14%). LC/MS: m/z 257 $(M+H)^+$. Rt: 2.25 min.

TABLE 11

| Compound | Structure | From | Physical data |
|---|---|---|---|
| Intermediate 31 Methyl 3-[({1-[(3,4-dichlorophenyl)methyl]-5-methyl-1H-1,2,3-triazol-4-yl}carbonyl)amino]-5-[(methylamino) carbonyl]benzoate | 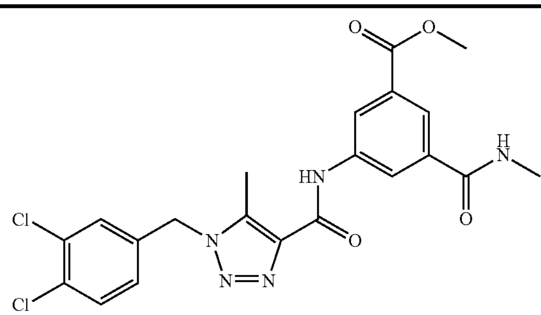 | 1-[(3,4-Dichlorophenyl)methyl]-5-methyl-1H-1,2,3-triazole-4-carboxylic acid (Intermediate 11) and methyl 3-amino-5-[(methylamino) carbonyl]benzoate (Intermediate 30) | LC/MS: m/z 476 $(M + H)+$, Rt: 3.15 min |

The following compounds were similarly prepared by a method analogous to that described for Intermediate 14

TABLE 12

| Compound | Structure | From | Physical data |
|---|---|---|---|
| Intermediate 34 Methyl 4-[({1-[(3,4-dichlorophenyl)methyl]-5-methyl-1H-1,2,3-triazol-4-yl}amino)carbonyl]benzoate | 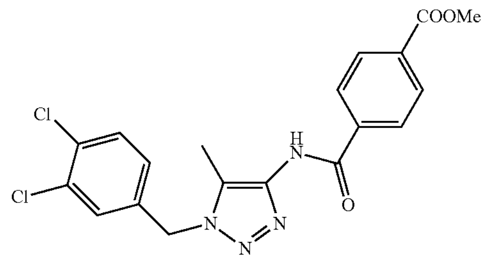 [SMILES: COC(=O)c1ccc(C(=O)Nc2nnn(Cc3ccc(Cl)c(Cl)c3)c2C)cc1] | 1-[(3,4-dichlorophenyl)methyl]-5-methyl-1H-1,2,3-triazol-4-amine (Intermediate 33) and 4-[(methyloxy)carbonyl]benzoic acid | LC/MS: m/z 419 (M + H)+, Rt: 3.11 min |

Example 1

N-[3,4-bis(Methyloxy)phenyl]-1-[(4-fluorophenyl)methyl]-5-methyl-1H-1,2,3-triazole-4-carboxamide

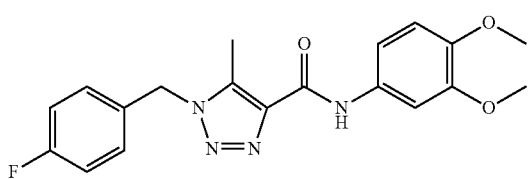 [SMILES: COc1ccc(NC(=O)c2nnn(Cc3ccc(F)cc3)c2C)cc1OC]

A mixture of 1-[(4-fluorophenyl)methyl]-5-methyl-1H-1,2,3-triazole-4-carboxylic acid (0.2 g, 0.85 mmol), 3,4-bis(methyloxy)aniline (0.156 g, 1.2 eq), HATU (0.485 g, 1.5 eq) and DIPEA (240 µL, 1.5 eq) in DMF was stirred at room temperature overnight. The solvent was evaporated and the residue was washed with water and extracted with DCM. The organic phase was dried over sodium sulphate, filtered and concentrated in vacuo. The residue was purified by flash column chromatography eluting with DCM to give after precipitation from ether, the title compound as a white solid (180 mg, 57%). HRMS calculated for $C_{19}H_{19}FN_4O_3$ $(M+H)^+$ 371.1519. found: 371.1500, Rt: 2.78 min. MP: 119.7° C.

The following compounds were similarly prepared by analogous method to that described for Example 1:

TABLE 13

| Compound | Structure | From | Physical data |
|---|---|---|---|
| Example 2 N-[3,4-bis(methyloxy)phenyl]-1-[(4-bromophenyl)methyl]-5-methyl-1H-1,2,3-triazole-4-carboxamide | 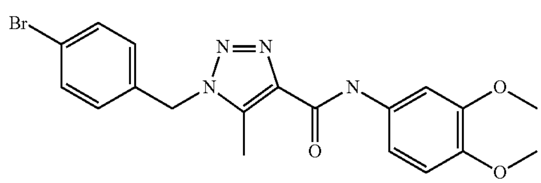 [SMILES: COc1ccc(NC(=O)c2nnn(Cc3ccc(Br)cc3)c2C)cc1OC] | 1-[(4-bromophenyl)methyl]-5-methyl-1H-1,2,3-triazole-4-carboxylic acid and 3,4-bis(methyloxy)aniline | HRMS calculated for $C_{19}H_{19}BrN_4O_3$ Theo: 431.0719 Found: 431.0684 Rt: 2.93 min. MP: 173° C. |
| Example 3 1-[(4-Bromophenyl)methyl]-5-methyl-N-{4-[(phenylmethyl)oxy]phenyl}-1H-1,2,3-triazole-4-carboxamide | 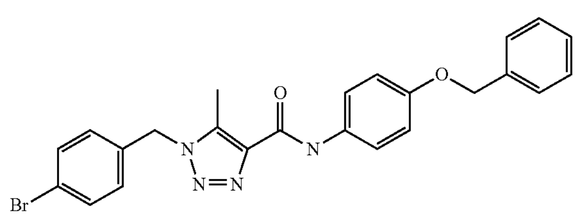 [SMILES: Cc1c(C(=O)Nc2ccc(OCc3ccccc3)cc2)nnn1Cc1ccc(Br)cc1] | 1-[(4-bromophenyl)methyl]-5-methyl-1H-1,2,3-triazole-4-carboxylic acid and 4-[(phenylmethyl)oxy]aniline | HRMS calculated for $C_{24}H_{21}BrN_4O_2$ Theo: 477.0926 Found: 477.0963 Rt: 3.49 min. MP: 168.7° C. |
| Example 4 1-[(4-Fluorophenyl)methyl]-5-methyl-N-{4-[(phenylmethyl)oxy]phenyl}-1H-1,2,3-triazole-4-carboxamide | 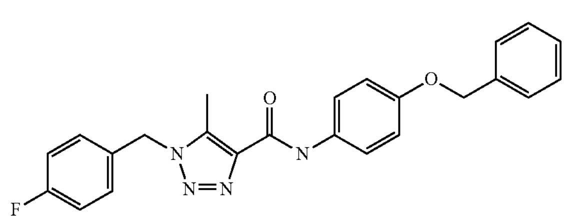 [SMILES: Cc1c(C(=O)Nc2ccc(OCc3ccccc3)cc2)nnn1Cc1ccc(F)cc1] | 1-[(4-fluorophenyl)methyl]-5-methyl-1H-1,2,3-triazole-4-carboxylic acid and 4-[(phenylmethyl)oxy]aniline | HRMS calculated for $C_{24}H_{21}FN_4O_2$ Theo: 417.1727 Found: 417.1768 Rt: 3.32 min. MP: 139.4° C. |

TABLE 13-continued

| Compound | Structure | From | Physical data |
|---|---|---|---|
| Example 5<br>1-[(4-Fluorophenyl)methyl]-5-methyl-N-{4-[(3-methylbutyl)oxy]phenyl}-1H-1,2,3-triazole-4-carboxamide | 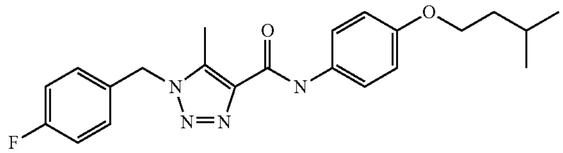 [SMILES: Cc1c(C(=O)Nc2ccc(OCCC(C)C)cc2)nnn1Cc1ccc(F)cc1] | 1-[(4-fluorophenyl)methyl]-5-methyl-1H-1,2,3-triazole-4-carboxylic acid and 4-[(3-methylbutyl)oxy]aniline | HRMS calculated for $C_{22}H_{25}FN_4O_2$<br>Theo: 397.2040<br>Found: 397.2061<br>Rt: 3.58 min<br>MP: 114° C. |
| Example 6<br>1-[(4-Bromophenyl)methyl]-5-methyl-N-{4-[(3-methylbutyl)oxy]phenyl}-1H-1,2,3-triazole-4-carboxamide | 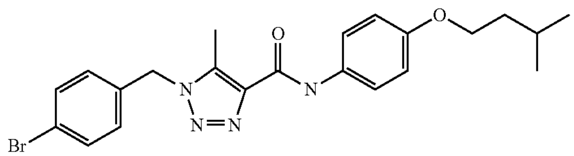 [SMILES: Cc1c(C(=O)Nc2ccc(OCCC(C)C)cc2)nnn1Cc1ccc(Br)cc1] | 1-[(4-bromophenyl)methyl]-5-methyl-1H-1,2,3-triazole-4-carboxylic acid and 4-[(3-methylbutyl)oxy]aniline | HRMS calculated for $C_{22}H_{25}BrN_4O_2$<br>Theo: 457.1239<br>Found: 457.1256<br>Rt: 3.76 min<br>MP: 137° C. |
| Example 7<br>5-Methyl-1-(phenylmethyl)-N-{4-[(phenylmethyl)oxy]phenyl}-1H-1,2,3-triazole-4-carboxamide | 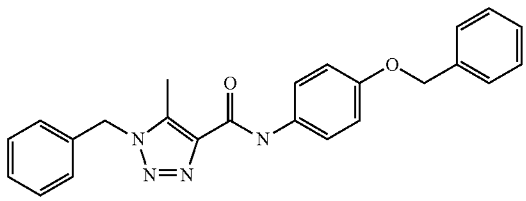 [SMILES: Cc1c(C(=O)Nc2ccc(OCc3ccccc3)cc2)nnn1Cc1ccccc1] | 5-methyl-1-(phenylmethyl)-1H-1,2,3-triazole-4-carboxylic acid and 4-[(phenylmethyl)oxy]aniline | HRMS calculated for $C_{24}H_{22}N_4O_2$<br>Theo: 399.1821<br>Found: 399.1819<br>Rt: 3.34 min<br>MP: 125° C. |
| Example 8<br>5-Methyl-N-{4-[(3-methylbutyl)oxy]phenyl}-1-(phenylmethyl)-1H-1,2,3-triazole-4-carboxamide | | 5-methyl-1-(phenylmethyl)-1H-1,2,3-triazole-4-carboxylic acid and 4-[(3-methylbutyl)oxy]aniline | HRMS calculated for $C_{22}H_{26}N_4O_2$<br>Theo: 379.2134<br>Found: 379.2165<br>Rt: 3.55 min<br>MP: 124° C. |
| Example 9<br>1-[(2'-Chloro-4-biphenylyl)methyl]-5-methyl-N-{4-[(3-methylbutyl)oxy]phenyl}-1H-1,2,3-triazole-4-carboxamide | 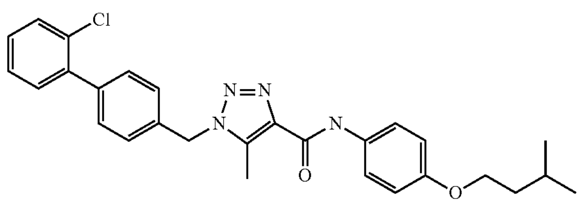 [SMILES: Cc1c(C(=O)Nc2ccc(OCCC(C)C)cc2)nnn1Cc1ccc(-c2ccccc2Cl)cc1] | 1-[(2'-chloro-4-biphenylyl)methyl]-5-methyl-1H-1,2,3-triazole-4-carboxylic acid (Intermediate 1) and 4-[(3-methylbutyl)oxy]aniline | HRMS calculated for $C_{28}H_{29}ClN_4O_2$<br>Theo: 489.2057<br>Found: 489.2104<br>Rt: 3.99 min<br>MP: 125° C. (decomposition) |
| Example 10<br>5-Methyl-N-{4-[(3-methylbutyl)oxy]phenyl}-1-[(4-methylphenyl)methyl]-1H-1,2,3-triazole-4-carboxamide | 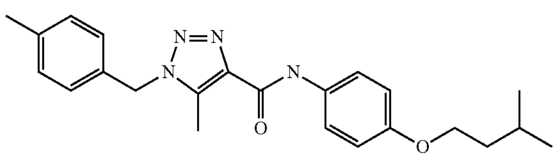 [SMILES: Cc1ccc(Cn2nnc(C(=O)Nc3ccc(OCCC(C)C)cc3)c2C)cc1] | 5-methyl-1-[(4-methylphenyl)methyl]-1H-1,2,3-triazole-4-carboxylic acid and 4-[(3-methylbutyl)oxy]aniline | HRMS calculated for $C_{23}H_{28}N_4O_2$<br>Theo: 393.2290<br>Found: 393.2285<br>Rt: 3.70 min<br>MP: 105° C. |
| Example 11<br>5-Methyl-N-{4-[(3-methylbutyl)oxy]phenyl}-1-{[4-(1-methylethyl)phenyl]methyl}-1H-1,2,3-triazole-4-carboxamide | 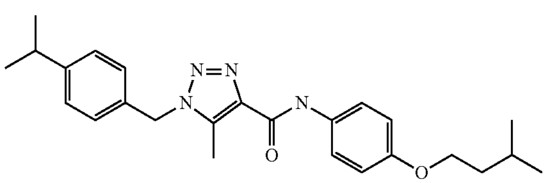 [SMILES: Cc1c(C(=O)Nc2ccc(OCCC(C)C)cc2)nnn1Cc1ccc(C(C)C)cc1] | 5-methyl-1-{[4-(1-methylethyl)phenyl]methyl}-1H-1,2,3-triazole-4-carboxylic acid and 4-[(3-methylbutyl)oxy]aniline | HRMS calculated for $C_{25}H_{32}N_4O_2$<br>Theo: 421.2603<br>Found: 421.2585<br>Rt: 3.93 min<br>MP: 114° C. (decomposition) |
| Example 12<br>N-[3,4-bis(Methyloxy)phenyl]-5-methyl-1-[(4-methylphenyl)methyl]-1H-1,2,3-triazole-4-carboxamide | 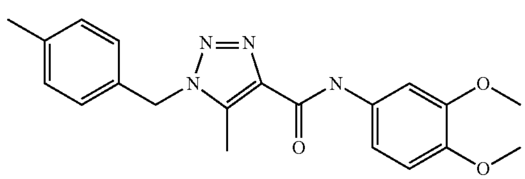 | 5-methyl-1-[(4-methylphenyl)methyl]-1H-1,2,3-triazole-4-carboxylic acid and 3,4-bis(methyloxy)aniline | HRMS calculated for $C_{20}H_{22}N_4O_3$<br>Theo: 367.1770<br>Found: 367.1751<br>Rt: 2.88 min<br>MP: 156° C. (decomposition) |

TABLE 13-continued

| Compound | Structure | From | Physical data |
|---|---|---|---|
| Example 13 1-(2-biphenylylmethyl)-N-[3,4-bis(methyloxy)phenyl]-5-methyl-1H-1,2,3-triazole-4-carboxamide | 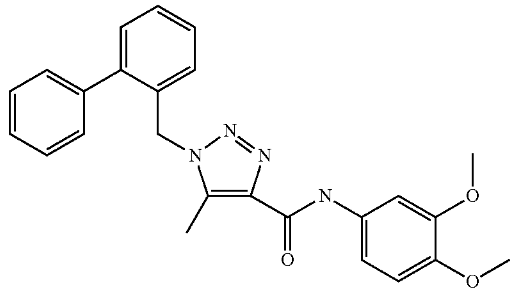 [SMILES: COc1ccc(NC(=O)c2nnn(Cc3ccccc3-c3ccccc3)c2C)cc1OC] | 1-(2-biphenylylmethyl)-5-methyl-1H-1,2,3-triazole-4-carboxylic acid (Intermediate 10) and 3,4-bis(methyloxy)aniline | HRMS calculated for $C_{25}H_{24}N_4O_3$ Theo: 429.1927 Found: 429.1937 Rt: 3.2 min MP: 121° C. |
| Example 14 N-[3,4-bis(Methyloxy)phenyl]-1-[(4-fluorophenyl)methyl]-1H-1,2,3-triazole-4-carboxamide | 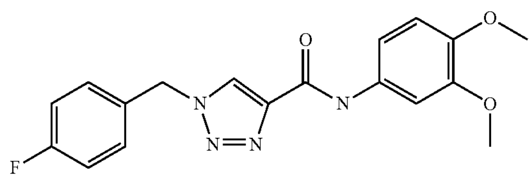 [SMILES: COc1ccc(NC(=O)c2cn(Cc3ccc(F)cc3)nn2)cc1OC] | 1-[(4-fluorophenyl)methyl]-1H-1,2,3-triazole-4-carboxylic acid 3,4-bis(methyloxy)aniline | HRMS calculated for $C_{18}H_{17}N_4O_3$ Theo: 357.1363 Found: 357.1355 Rt: 2.55 min MP: 197.8° C. |
| Example 15 1-[(3,4-Dichlorophenyl)methyl]-5-methyl-N-[4-(1,3-oxazol-2-yl)phenyl]-1H-1,2,3-triazole-4-carboxamide | 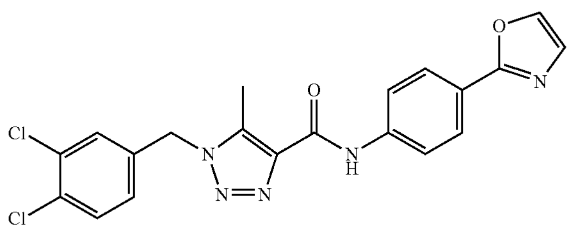 [SMILES: Cc1c(C(=O)Nc2ccc(-c3ncco3)cc2)nnn1Cc1ccc(Cl)c(Cl)c1] | 1-[(3,4-dichlorophenyl)methyl]-5-methyl-1H-1,2,3-triazole-4-carboxylic acid (Intermediate 11) and 4-(1,3-oxazol-2-yl)aniline | HRMS calculated for $C_{20}H_{15}Cl_2N_5O_2$ Theo: 428.0681 Found: 428.0716 Rt: 3.14 min MP: 218° C. |
| Example 16 1-[(3,4-Dichlorophenyl)methyl]-N-[4-(hydroxymethyl)phenyl]-5-methyl-1H-1,2,3-triazole-4-carboxamide | 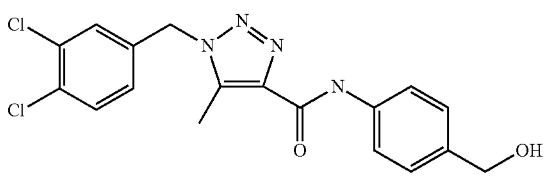 [SMILES: Cc1c(C(=O)Nc2ccc(CO)cc2)nnn1Cc1ccc(Cl)c(Cl)c1] | 1-[(3,4-dichlorophenyl)methyl]-5-methyl-1H-1,2,3-triazole-4-carboxylic acid (Intermediate 11) and (4-aminophenyl)methanol | HRMS calculated for $C_{18}H_{16}Cl_2N_4O_2$ Theo: 391.0728 Found: 391.0755 Rt: 2.77 min MP: 183° C. |
| Example 17 Methyl 4-[({1-[(3,4-dichlorophenyl)methyl]-5-methyl-1H-1,2,3-triazol-4-yl}carbonyl)amino]-3-(methyloxy)benzoate | 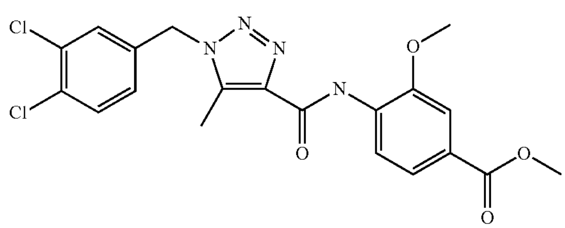 [SMILES: COC(=O)c1ccc(NC(=O)c2nnn(Cc3ccc(Cl)c(Cl)c3)c2C)c(OC)c1] | 1-[(3,4-dichlorophenyl)methyl]-5-methyl-1H-1,2,3-triazole-4-carboxylic acid (Intermediate 11) and methyl 4-amino-3-(methyloxy)benzoate | HRMS calculated for $C_{20}H_{18}Cl_2N_4O_4$ Theo: 449.0783 Found: 449.0813 Rt: 3.42 min MP: 212° C. |
| Example 18 1-[(3,4-Dichlorophenyl)methyl]-5-methyl-N-{3-[(methylamino)carbonyl]phenyl}-1H-1,2,3-triazole-4-carboxamide | 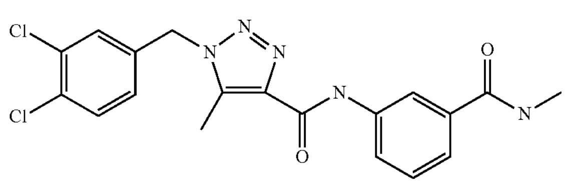 [SMILES: CNC(=O)c1cccc(NC(=O)c2nnn(Cc3ccc(Cl)c(Cl)c3)c2C)c1] | methyl 1-(2-biphenylylmethyl)-5-methyl-1H-1,2,3-triazole-4-carboxylate (Intermediate 6) and 3-amino-N-methylbenzamide | HRMS calculated for $C_{19}H_{17}Cl_2N_5O_2$ Theo: 418.0837 Found: 418.0851 Rt: 2.74 min MP: 203.9° C. |
| Example 19 1-[(3,4-Dichlorophenyl)methyl]-5-methyl-N-{4-[(methylamino)carbonyl]phenyl}-1H-1,2,3-triazole-4-carboxamide | 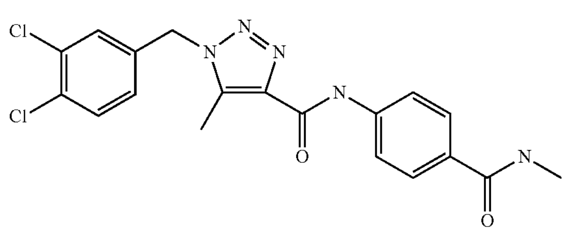 [SMILES: CNC(=O)c1ccc(NC(=O)c2nnn(Cc3ccc(Cl)c(Cl)c3)c2C)cc1] | 1-[(3,4-dichlorophenyl)methyl]-5-methyl-1H-1,2,3-triazole-4-carboxylic acid (Intermediate 11) and 4-amino-N-methylbenzamide | HRMS calculated for $C_{19}H_{17}Cl_2N_5O_2$ Theo: 418.0837 Found: 418.0839 Rt: 2.71 min MP: 183.7° C. |

TABLE 13-continued

| Compound | Structure | From | Physical data |
|---|---|---|---|
| Example 20 Ethyl 3-[({1-[(3,4-dichlorophenyl)methyl]-5-methyl-1H-1,2,3-triazol-4-yl}carbonyl)amino]benzoate | 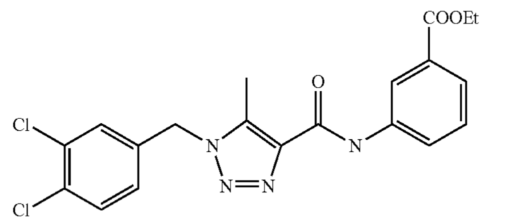 [SMILES: CCOC(=O)c1cccc(NC(=O)c2nnn(Cc3ccc(Cl)c(Cl)c3)c2C)c1] | 1-[(3,4-dichlorophenyl)methyl]-5-methyl-1H-1,2,3-triazole-4-carboxylic acid (Intermediate 11) and ethyl 3-aminobenzoate | HRMS calculated for $C_{20}H_{18}Cl_2N_4O_3$ Theo: 433.0834 Found: 433.0797 Rt: 3.38 min MP: 131.8° C. |
| Example 21 N-[3-(Acetylamino)phenyl]-1-[(3,4-dichlorophenyl)methyl]-5-methyl-1H-1,2,3-triazole-4-carboxamide | 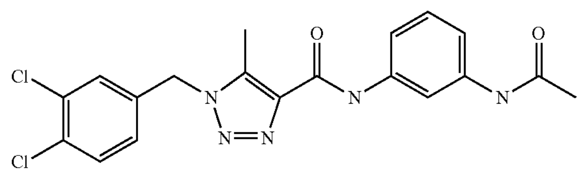 [SMILES: CC(=O)Nc1cccc(NC(=O)c2nnn(Cc3ccc(Cl)c(Cl)c3)c2C)c1] | 1-[(3,4-dichlorophenyl)methyl]-5-methyl-1H-1,2,3-triazole-4-carboxylic acid (Intermediate 11) and N-(3-aminophenyl)acetamide | HRMS calculated for $C_{19}H_{17}Cl_2N_5O_2$ Theo: 418.0837 Found: 418.0830 Rt: 2.78 min MP: 203.4° C. |
| Example 22 N-[4-(Acetylamino)phenyl]-1-[(3,4-dichlorophenyl)methyl]-5-methyl-1H-1,2,3-triazole-4-carboxamide | 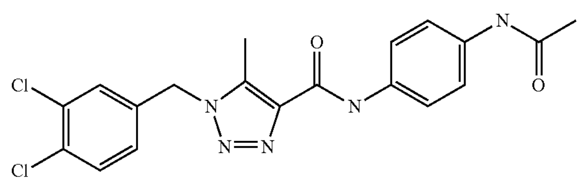 [SMILES: CC(=O)Nc1ccc(NC(=O)c2nnn(Cc3ccc(Cl)c(Cl)c3)c2C)cc1] | 1-[(3,4-dichlorophenyl)methyl]-5-methyl-1H-1,2,3-triazole-4-carboxylic acid (Intermediate 11) and N-(4-aminophenyl)acetamide | HRMS calculated for $C_{19}H_{17}Cl_2N_5O_2$ Theo: 418.0837 Found: 418.0840 Rt: 2.72 min MP: 202.4° C. |
| Example 23 1-[(3,4-Dichlorophenyl)methyl]-N-[3-(hydroxymethyl)-2-methylphenyl]-5-methyl-1H-1,2,3-triazole-4-carboxamide | 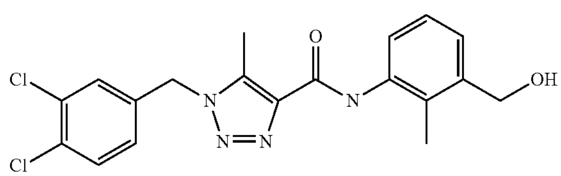 [SMILES: Cc1c(CO)cccc1NC(=O)c1nnn(Cc2ccc(Cl)c(Cl)c2)c1C] | 1-[(3,4-dichlorophenyl)methyl]-5-methyl-1H-1,2,3-triazole-4-carboxylic acid (Intermediate 11) and (3-amino-2-methylphenyl)methanol | HRMS calculated for $C_{19}H_{18}Cl_2N_4O_2$ Theo: 405.0885 Found: 405.0878 Rt: 2.78 min MP: 174.3° C. |
| Example 24 1-[(3,4-Dichlorophenyl)methyl]-N-[3-(hydroxymethyl)phenyl]-5-methyl-1H-1,2,3-triazole-4-carboxamide | 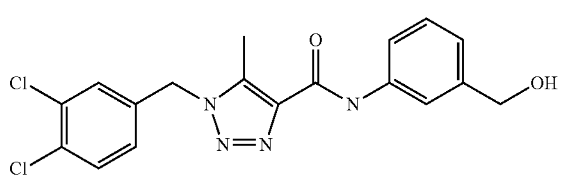 [SMILES: Cc1c(C(=O)Nc2cccc(CO)c2)nnn1Cc1ccc(Cl)c(Cl)c1] | 1-[(3,4-dichlorophenyl)methyl]-5-methyl-1H-1,2,3-triazole-4-carboxylic acid (Intermediate 11) and (3-aminophenyl)methanol | HRMS calculated for $C_{18}H_{16}Cl_2N_4O_2$ Theo: 391.0728 Found: 391.0695 Rt: 2.78 min MP: 185.2° C. |
| Example 25 Methyl 3-[({1-[(3,4-dichlorophenyl)methyl]-5-methyl-1H-1,2,3-triazol-4-yl}carbonyl)amino]-4-(methyloxy)benzoate | 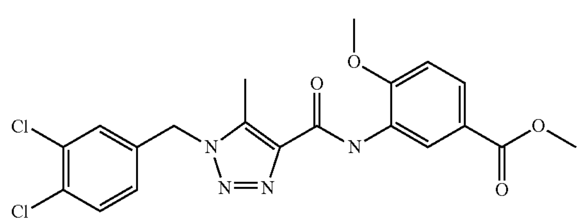 [SMILES: COC(=O)c1ccc(OC)c(NC(=O)c2nnn(Cc3ccc(Cl)c(Cl)c3)c2C)c1] | 1-[(3,4-dichlorophenyl)methyl]-5-methyl-1H-1,2,3-triazole-4-carboxylic acid (Intermediate 11) and methyl 3-amino-4-(methyloxy)benzoate | HRMS calculated for $C_{20}H_{18}Cl_2N_4O_4$ Theo: 449.0783 Found: 449.0802 Rt: 3.36 min MP: 203° C. |
| Example 26 1-[(3,4-Dichlorophenyl)methyl]-N-[4-hydroxy-3-(hydroxymethyl)phenyl]-5-methyl-1H-1,2,3-triazole-4-carboxamide | 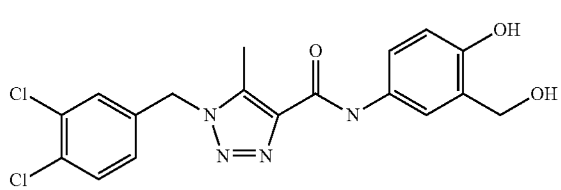 [SMILES: Cc1c(C(=O)Nc2ccc(O)c(CO)c2)nnn1Cc1ccc(Cl)c(Cl)c1] | 1-[(3,4-dichlorophenyl)methyl]-5-methyl-1H-1,2,3-triazole-4-carboxylic acid (Intermediate 11) and 4-amino-2-(hydroxymethyl)phenol | HRMS calculated for $C_{18}H_{16}Cl_2N_4O_3$ Theo: 407.0677 Found: 407.0683 Rt: 2.57 min MP: 175.6° C. |

TABLE 13-continued

| Compound | Structure | From | Physical data |
|---|---|---|---|
| Example 27 Ethyl {4-[({1-[(3,4-dichlorophenyl)methyl]-5-methyl-1H-1,2,3-triazol-4-yl}carbonyl)amino]phenyl}acetate | 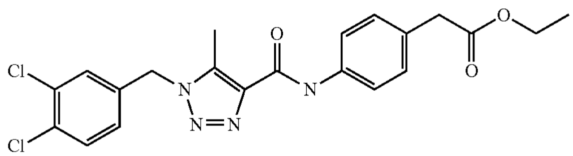 [SMILES: CCOC(=O)Cc1ccc(NC(=O)c2nnn(Cc3ccc(Cl)c(Cl)c3)c2C)cc1] | 1-[(3,4-dichlorophenyl)methyl]-5-methyl-1H-1,2,3-triazole-4-carboxylic acid (Intermediate 11) and ethyl (4-aminophenyl) acetate | HRMS calculated for $C_{21}H_{20}Cl_2N_4O_3$ Theo: 447.0990 Found: 447.0975 Rt: 3.25 min MP: 139° C. |
| Example 28 Methyl 4-[({1-[{3,4-dichlorophenyl)methyl]-5-methyl-1H-1,2,3-triazol-4-yl}carbonyl)amino]-2-(methyloxy)benzoate | 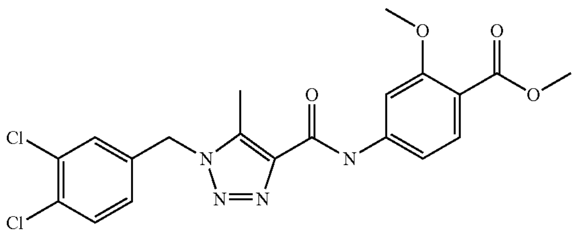 [SMILES: COC(=O)c1ccc(NC(=O)c2nnn(Cc3ccc(Cl)c(Cl)c3)c2C)cc1OC] | 1-[(3,4-dichlorophenyl)methyl]-5-methyl-1H-1,2,3-triazole-4-carboxylic acid (Intermediate 11) and methyl 4-amino-2-(methyloxy)benzoate | HRMS calculated for $C_{20}H_{18}Cl_2N_4O_4$ Theo: 449.0783 Found: 449.0787 Rt: 3.1 min MP: 175.9° C. |
| Example 29 Methyl 5-[({1-[(3,4-dichlorophenyl)methyl]-5-methyl-1H-1,2,3-triazol-4-yl}carbonyl)amino]-2-hydroxybenzoate | | 1-[(3,4-dichlorophenyl)methyl]-5-methyl-1H-1,2,3-triazole-4-carboxylic acid (Intermediate 11) and methyl 5-amino-2-hydroxybenzoate | HRMS calculated for $C_{19}H_{16}Cl_2N_4O_4$ Theo: 435.0627 Found: 435.0638 Rt: 3.2 min MP: 180° C. |
| Example 30 Methyl {3-[({1-[(3,4-dichlorophenyl)methyl)-5-methyl-1H-1,2,3-triazol-4-yl}carbonyl)amino]phenyl}acetate | 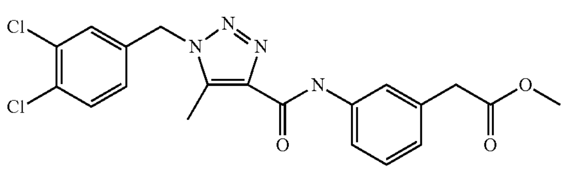 [SMILES: COC(=O)Cc1cccc(NC(=O)c2nnn(Cc3ccc(Cl)c(Cl)c3)c2C)c1] | 1-[(3,4-dichlorophenyl)methyl]-5-methyl-1H-1,2,3-triazole-4-carboxylic acid (Intermediate 11) and methyl (3-aminophenyl) acetate | HRMS calculated for $C_{20}H_{18}Cl_2N_4O_3$ Theo: 433.0834 Found: 433.0825 Rt: 3.14 min MP: 116° C. |
| Example 31 1-[(3,4-Dichlorophenyl)methyl]-N-(3-hydroxyphenyl)-5-methyl-1H-1,2,3-triazole-4-carboxamide | 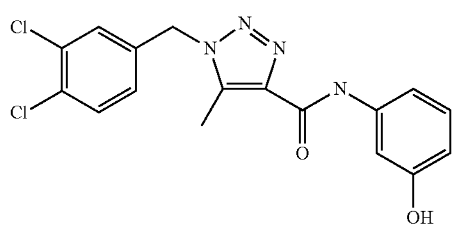 [SMILES: Cc1c(C(=O)Nc2cccc(O)c2)nnn1Cc1ccc(Cl)c(Cl)c1] | 1-[(3,4-dichlorophenyl)methyl]-5-methyl-1H-1,2,3-triazole-4-carboxylic acid (Intermediate 11) and 3-aminophenol | HRMS calculated for $C_{17}H_{14}Cl_2N_4O_2$ Theo: 377.0572 Found: 377.0593 Rt: 2.86 min MP: 192.5° C. |
| Example 32 Methyl 5-[({1-[{3,4-dichlorophenyl)methyl]-5-methyl-1H-1,2,3-triazol-4-yl}carbonyl)amino]-2-fluorobenzoate | 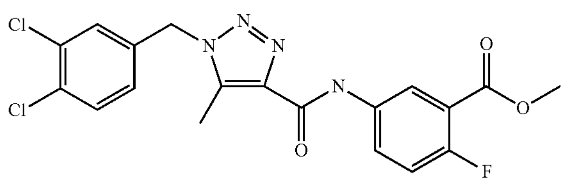 [SMILES: COC(=O)c1cc(NC(=O)c2nnn(Cc3ccc(Cl)c(Cl)c3)c2C)ccc1F] | 1-[(3,4-dichlorophenyl)methyl]-5-methyl-1H-1,2,3-triazole-4-carboxylic acid (Intermediate 11) and methyl 5-amino-2-fluorobenzoate | HRMS calculated for $C_{19}H_{15}Cl_2FN_4O_3$ Theo: 437.0583 Found: 437.0544 Rt: 3.22 min MP: 169.8° C. |
| Example 33 N-[5-(Aminocarbonyl)-2-(methyloxy)phenyl]-1-[(3,4-dichlorophenyl)methyl]-5-methyl-1H-1,2,3-triazole-4-carboxamide | 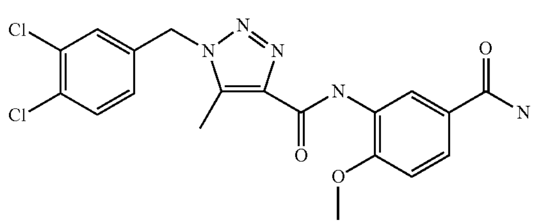 [SMILES: COc1ccc(C(N)=O)cc1NC(=O)c1nnn(Cc2ccc(Cl)c(Cl)c2)c1C] | 1-[(3,4-dichlorophenyl)methyl]-5-methyl-1H-1,2,3-triazole-4-carboxylic acid (Intermediate 11) and 3-amino-4-(methyloxy)benzamide | HRMS calculated for $C_{19}H_{17}Cl_2N_5O_3$ Theo: 434.0786 Found: 434.0773 Rt: 2.77 min MP: 218.2° C. |

TABLE 13-continued

| Compound | Structure | From | Physical data |
|---|---|---|---|
| Example 34 Methyl 4-chloro-3-[({1-[(3,4-dichlorophenyl)methyl]-5-methyl-1H-1,2,3-triazol-4-yl}carbonyl)amino]benzoate | 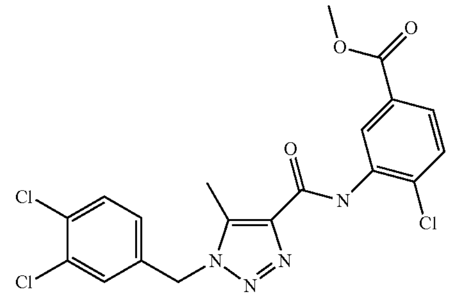 | 1-[(3,4-dichlorophenyl)methyl]-5-methyl-1H-1,2,3-triazole-4-carboxylic acid (Intermediate 11) and methyl 3-amino-4-chlorobenzoate | HRMS calculated for $C_{19}H_{15}Cl_3N_4O_3$ Theo: 453.0288 Found: 453.0330 Rt: 3.59 min MP: 206.4° C. |
| Example 35 Methyl [3-[({1-[(3,4-dichlorophenyl)methyl]-5-methyl-1H-1,2,3-triazol-4-yl}carbonyl)amino]-4-(methyloxy)phenyl]acetate | 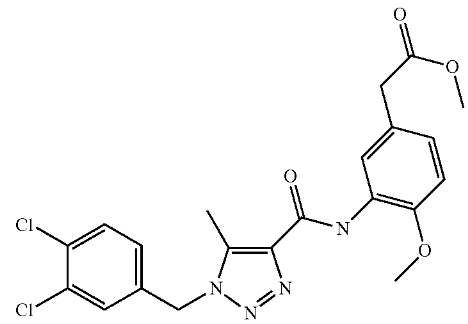 [SMILES: COC(=O)Cc1ccc(OC)c(NC(=O)c2nnn(Cc3ccc(Cl)c(Cl)c3)c2C)c1] | 1-[(3,4-dichlorophenyl)methyl]-5-methyl-1H-1,2,3-triazole-4-carboxylic acid (Intermediate 11) and methyl [3-amino-4-(methyloxy)phenyl]acetate | HRMS calculated for $C_{21}H_{20}Cl_2N_4O_4$ Theo: 463.0940 Found: 463.0985 Rt: 3.29 min MP: 133° C. |
| Example 36 Methyl 3-[({1-[(3,4-dichlorophenyl)methyl]-5-methyl-1H-1,2,3-triazol-4-yl}carbonyl)amino]-4-fluorobenzoate | 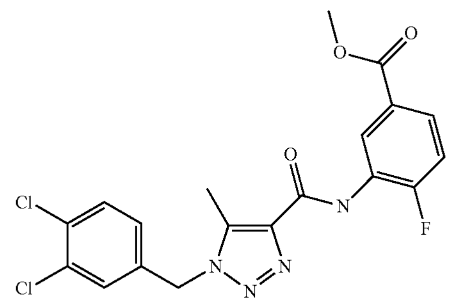 [SMILES: COC(=O)c1ccc(F)c(NC(=O)c2nnn(Cc3ccc(Cl)c(Cl)c3)c2C)c1] | 1-[(3,4-dichlorophenyl)methyl]-5-methyl-1H-1,2,3-triazole-4-carboxylic acid (Intermediate 11) and methyl 3-amino-4-fluorobenzoate | HRMS calculated for $C_{19}H_{15}Cl_2FN_4O_3$ Theo: 437.0583 Found: 437.0624 Rt: 3.37 min MP: 195.7° C. |
| Example 37 N-[3-(Hydroxymethyl)phenyl]-5-methyl-1-(phenylmethyl)-1H-1,2,3-triazole-4-carboxamide | 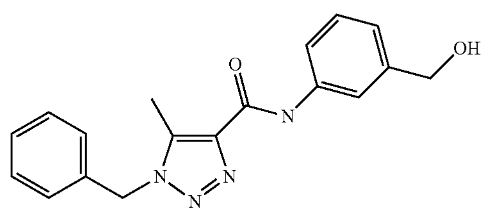 [SMILES: Cc1c(C(=O)Nc2cccc(CO)c2)nnn1Cc1ccccc1] | 5-methyl-1-(phenylmethyl)-1H-1,2,3-triazole-4-carboxylic acid (commercially available) and (3-aminophenyl)methanol | HRMS calculated for $C_{18}H_{18}N_4O_2$ Theo: 323.1508 Found: 323.1529 Rt: 2.45 min MP: 105.8° C. |
| Example 38 N-[4-(Hydroxymethyl)phenyl]-5-methyl-1-(phenylmethyl)-1H-1,2,3-triazole-4-carboxamide | 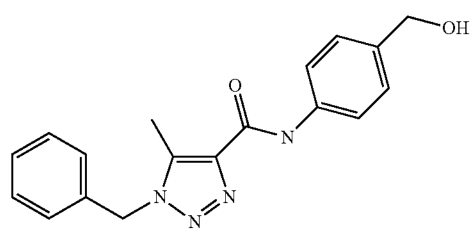 [SMILES: Cc1c(C(=O)Nc2ccc(CO)cc2)nnn1Cc1ccccc1] | 5-methyl-1-(phenylmethyl)-1H-1,2,3-triazole-4-carboxylic acid (commercially available) and (4-aminophenyl)methanol | HRMS calculated for $C_{18}H_{18}N_4O_2$ Theo: 323.1508 Found: 323.1504 Rt: 2.42 min MP: 149.1° C. |
| Example 39 N-[3-(Hydroxymethyl)-2-methylphenyl]-5-methyl-1-(phenylmethyl)-1H-1,2,3-triazole-4-carboxamide | 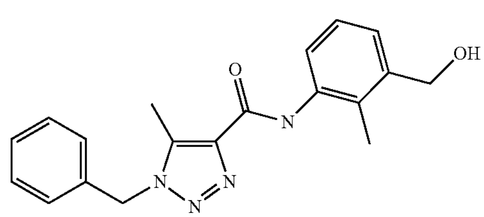 [SMILES: Cc1c(CO)cccc1NC(=O)c1nnn(Cc2ccccc2)c1C] | 5-methyl-1-(phenylmethyl)-1H-1,2,3-triazole-4-carboxylic acid (commercially available) and (3-amino-2-methylphenyl)methanol | HRMS calculated for $C_{19}H_{20}N_4O_2$ Theo: 337.1664 Found: 337.1654 Rt: 2.44 min MP: 157° C. |

TABLE 13-continued

| Compound | Structure | From | Physical data |
|---|---|---|---|
| Example 40 1-[(3,5-Dichlorophenyl)methyl]-N-[3-(hydroxymethyl)phenyl]-5-methyl-1H-1,2,3-triazole-4-carboxamide | 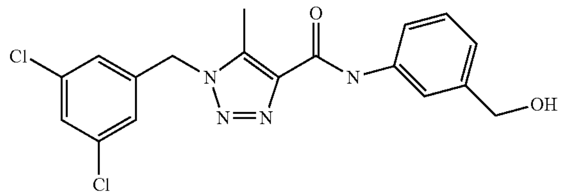 [SMILES: Cc1c(C(=O)Nc2cccc(CO)c2)nnn1Cc1cc(Cl)cc(Cl)c1] | 1-[(3,5-dichlorophenyl)methyl]-5-methyl-1H-1,2,3-triazole-4-carboxylic acid (Intermediate 12) and (3-aminophenyl)methanol | HRMS calculated for $C_{18}H_{16}Cl_2N_4O_2$ Theo: 391.0728 Found: 391.0726 Rt: 2.84 min MP: 159° C. |
| Example 41 Methyl 3-[({1-[{3,5-dichlorophenyl)methyl]-5-methyl-1H-1,2,3-triazol-4-yl}carbonyl)amino]-4-(methyloxy)benzoate | 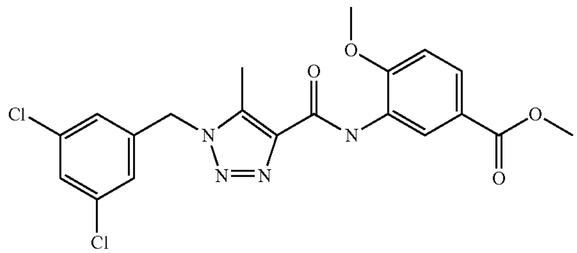 [SMILES: COC(=O)c1ccc(OC)c(NC(=O)c2nnn(Cc3cc(Cl)cc(Cl)c3)c2C)c1] | 1-[(3,5-dichlorophenyl)methyl]-5-methyl-1H-1,2,3-triazole-4-carboxylic acid (Intermediate 12) and methyl 3-amino-4-(methyloxy)benzoate | HRMS calculated for $C_{20}H_{18}Cl_2N_4O_4$ Theo: 449.0783 Found: 449.0783 Rt: 3.44 min MP: 213° C. |
| Example 42 1-[(3,5-Dichlorophenyl)methyl]-N-[3-(hydroxymethyl)-2-methylphenyl]-5-methyl-1H-1,2,3-triazole-4-carboxamide | 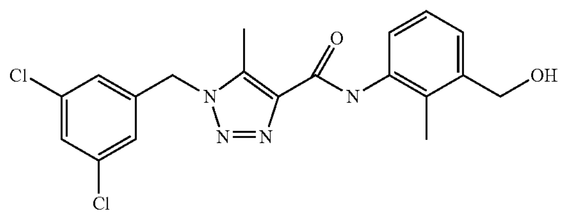 [SMILES: Cc1c(CO)cccc1NC(=O)c1nnn(Cc2cc(Cl)cc(Cl)c2)c1C] | 1-[(3,5-dichlorophenyl)methyl]-5-methyl-1H-1,2,3-triazole-4-carboxylic acid (Intermediate 12) and (3-amino-2-methylphenyl)methanol | HRMS calculated for $C_{19}H_{18}Cl_2N_4O_2$ Theo: 405.0885 Found: 405.0860 Rt: 2.83 min MP: 185° C. |
| Example 43 N-{3-[(Acetylamino)methyl]phenyl}-1-[(3,4-dichlorophenyl)methyl]-5-methyl-1H-1,2,3-triazole-4-carboxamide | 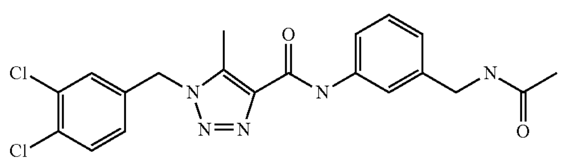 [SMILES: CC(=O)NCc1cccc(NC(=O)c2nnn(Cc3ccc(Cl)c(Cl)c3)c2C)c1] | 1-[(3,4-dichlorophenyl)methyl]-5-methyl-1H-1,2,3-triazole-4-carboxylic acid (Intermediate 11) and N-[(3-aminophenyl)methyl]acetamide | HRMS calculated for $C_{20}H_{19}Cl_2N_5O_2$ Theo: 432.0994 Found: 432.1003 Rt: 2.83 min MP: 188.4° C. |
| Example 44 1-[(3,4-Dichlorophenyl)methyl]-N-[3-(1-hydroxyethyl)phenyl]-5-methyl-1H-1,2,3-triazole-4-carboxamide | 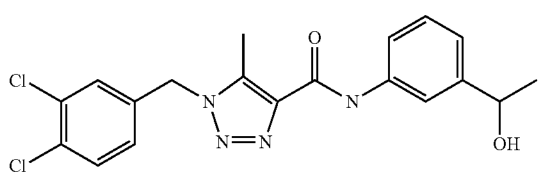 [SMILES: Cc1c(C(=O)Nc2cccc(C(C)O)c2)nnn1Cc1ccc(Cl)c(Cl)c1] | 1-[(3,4-dichlorophenyl)methyl]-5-methyl-1H-1,2,3-triazole-4-carboxylic acid (Intermediate 11) and 1-(3-aminophenyl)ethanol | HRMS calculated for $C_{19}H_{18}Cl_2N_4O_2$ Theo: 405.0885 Found: 405.0869 Rt: 2.97 min MP: 145° C. |
| Example 45 N-[4-Chloro-3-(hydroxymethyl)phenyl]-1-[(3,4-dichlorophenyl)methyl]-5-methyl-1H-1,2,3-triazole-4-carboxamide | 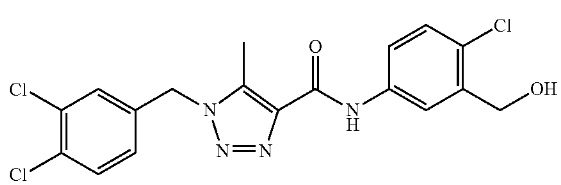 [SMILES: Cc1c(C(=O)Nc2ccc(Cl)c(CO)c2)nnn1Cc1ccc(Cl)c(Cl)c1] | 1-[(3,4-dichlorophenyl)methyl]-5-methyl-1H-1,2,3-triazole-4-carboxylic acid (Intermediate 11) and (5-amino-2-chlorophenyl)methanol | HRMS calculated for $C_{18}H_{15}Cl_3N_4O_2$ Theo: 425.0339 Found: 425.0315 Rt: 3.12 min MP: 190.3° C. |
| Example 46 Dimethyl 4-[({1-[(3,4-dichlorophenyl)methyl)-5-methyl-1H-1,2,3-triazol-4-yl}carbonyl)amino]-1,2-benzene dicarboxylate | 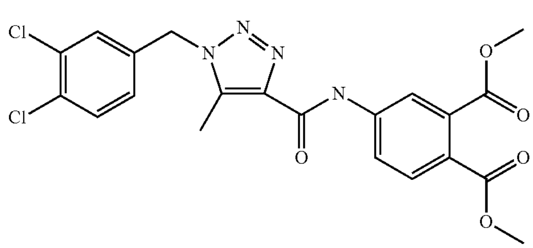 [SMILES: COC(=O)c1ccc(NC(=O)c2nnn(Cc3ccc(Cl)c(Cl)c3)c2C)cc1C(=O)OC] | 1-[(3,4-dichlorophenyl)methyl]-5-methyl-1H-1,2,3-triazole-4-carboxylic acid (Intermediate 11) and dimethyl 4-amino-1,2-benzene dicarboxylate | HRMS calculated for $C_{21}H_{18}Cl_2N_4O_5$ Theo: 477.0732 Found: 477.0703 Rt: 3.23 min MP: 148° C. |

TABLE 13-continued

| Compound | Structure | From | Physical data |
|---|---|---|---|
| Example 47 Methyl 5-[({1-[(3,5-dichlorophenyl)methyl]-5-methyl-1H-1,2,3-triazol-4-yl}carbonyl)amino]-2-fluorobenzoate | 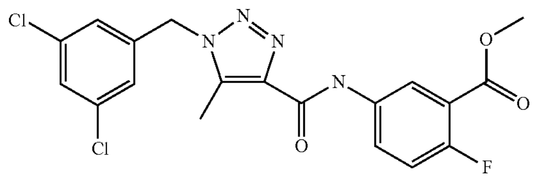 [SMILES: COC(=O)c1cc(NC(=O)c2nnn(Cc3cc(Cl)cc(Cl)c3)c2C)ccc1F] | 1-[(3,5-dichlorophenyl)methyl]-5-methyl-1H-1,2,3-triazole-4-carboxylic acid (Intermediate 12) and methyl 5-amino-2-fluorobenzoate | HRMS calculated for $C_{19}H_{15}Cl_2FN_4O_3$ Theo: 437.0583 Found: 437.0562 Rt: 3.29 min MP: 191° C. |
| Example 48 Ethyl 4-[({1-[(3,4-dichlorophenyl)methyl]-5-methyl-1H-1,2,3-triazol-4-yl}carbonyl)amino]benzoate | 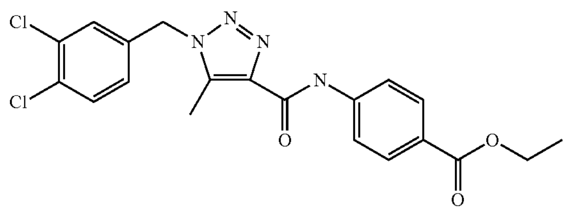 [SMILES: CCOC(=O)c1ccc(NC(=O)c2nnn(Cc3ccc(Cl)c(Cl)c3)c2C)cc1] | 1-[(3,4-dichlorophenyl)methyl]-5-methyl-1H-1,2,3-triazole-4-carboxylic acid (Intermediate 11) and ethyl 4-aminobenzoate | HRMS calculated for $C_{20}H_{18}Cl_2N_4O_3$ Theo: 433.0834 Found: 433.0830 Rt: 3.37 min MP: 167° C. |

Example 49

1-[(3,4-Dichlorophenyl)methyl]-N-[4-(hydroxymethyl)-2-(methyloxy)phenyl]-5-methyl-1H-1,2,3-triazole-4-carboxamide

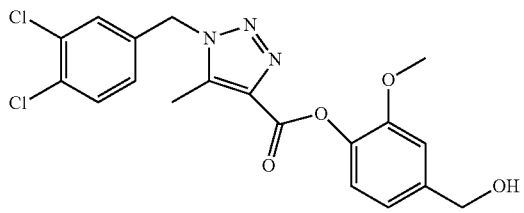 [SMILES: COc1cc(CO)ccc1OC(=O)c1nnn(Cc2ccc(Cl)c(Cl)c2)c1C]

To a solution of methyl 4-[({1-[(3,4-dichlorophenyl)methyl]-5-methyl-1H-1,2,3-triazol-4-yl}carbonyl)amino]-3-(methyloxy)benzoate (Example 17) (0.1 g, 0.2 mmol) in THF was added a 1M solution of DIBAL-H in THF (800 μL, 4 eq) and the reaction was stirred to room temperature for 2 hours. Solid NH$_4$Cl was added followed by water and a 1N HCl solution. The aqueous phase was extracted with ether and AcOEt, dried over sodium sulphate and evaporated. After recrystallisation from acetonitrile, the title compound was obtained as a white solid (30 mg, 35%). HRMS calculated for $C_{19}H_{18}Cl_2N_4O_3$ (M+H)$^+$ 421.0834. found: 421.0834, Rt: 2.94 min. MP: 136° C.

The following compounds were similarly prepared by analogous method to that described for Example 49:

TABLE 14

| Compound | Structure | From | Physical data |
|---|---|---|---|
| Example 50 1-[(3,4-Dichlorophenyl)methyl]-N-[4-(2-hydroxyethyl)phenyl]-5-methyl-1H-1,2,3-triazole-4-carboxamide | 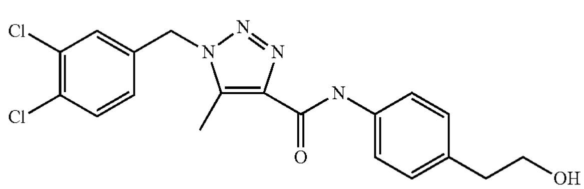 [SMILES: Cc1c(C(=O)Nc2ccc(CCO)cc2)nnn1Cc1ccc(Cl)c(Cl)c1] | Ethyl {4-[({1-[(3,4-dichlorophenyl)methyl]-5-methyl-1H-1,2,3-triazol-4-yl}carbonyl)amino]phenyl}acetate (Example 27) | HRMS calculated for $C_{19}H_{18}Cl_2N_4O_2$ Theo: 405.0885 Found: 405.0885 Rt: 2.79 min. MP: 144° C. |
| Example 51 1-[(3,4-Dichlorophenyl)methyl]-N-[5-(hydroxymethyl)-2-(methyloxy)phenyl]-5-methyl-1H-1,2,3-triazole-4-carboxamide | 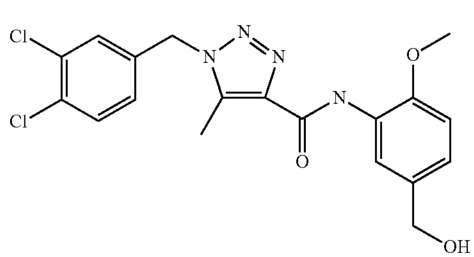 [SMILES: COc1ccc(CO)cc1NC(=O)c1nnn(Cc2ccc(Cl)c(Cl)c2)c1C] | Methyl 3-[({1-[(3,4-dichlorophenyl)methyl]-5-methyl-1H-1,2,3-triazol-4-yl}carbonyl)amino]-4-(methyloxy)benzoate (Example 25) | HRMS calculated for $C_{19}H_{18}Cl_2N_4O_3$ Theo: 421.0834 Found: 421.0794 Rt: 2.91 min. MP: 198° C. |

Example 52

N-[3,5-bis(Hydroxymethyl)phenyl]-1-[(3,4-dichlorophenyl)methyl]-5-methyl-1H-1,2,3-triazole-4-carboxamide

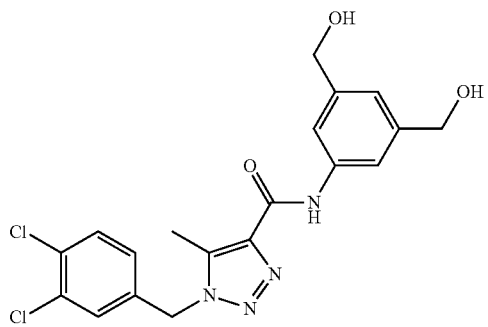 [SMILES: Cc1c(C(=O)Nc2cc(CO)cc(CO)c2)nnn1Cc1ccc(Cl)c(Cl)c1]

To a solution of dimethyl 5-[({1-[(3,4-dichlorophenyl)methyl]-5-methyl-1H-1,2,3-triazol-4-yl}carbonyl)amino]-1,3-benzenedicarboxylate (Intermediate 14) (0.65 g, 1.3 mmol) in THF (40 mL), was added a 1M solution of DIBAL-H in toluene (10 mL, 7 eq) and the reaction was stirred to room temperature for 2 hours. Solid NH$_4$Cl was added and the reaction mixture was stirred at RT for 30 min. The aqueous phase was extracted with ether and AcOEt, dried over sodium sulphate and evaporated. After recrystallisation from acetonitrile, the title compound was obtained as a white solid (240 mg, 44%). HRMS calculated for $C_{19}H_{18}Cl_2N_4O_3$ (M+H)+ 421.0834. found: 421.0833, Rt: 2.51 min. MP: 194.5° C.

The following compounds were similarly prepared by analogous method to that described for Example 49:

TABLE 15

| Compound | Structure | From | Physical data |
|---|---|---|---|
| Example 53<br>1-[(3,4-Dichlorophenyl)methyl]-N-[4-fluoro-3-(hydroxymethyl)phenyl]-5-methyl-1H-1,2,3-triazole-4-carboxamide | | methyl 5-[({1-[(3,4-dichlorophenyl)methyl]-5-methyl-1H-1,2,3-triazol-4-yl}carbonyl)amino]-2-fluorobenzoate (Example 32) | HRMS calculated for $C_{18}H_{15}Cl_2FN_4O_2$<br>Theo: 409.0634<br>Found: 409.0617<br>Rt: 2.87 min.<br>MP: 189.7° C. |
| Example 54<br>1-[(3,4-Dichlorophenyl)methyl]-N-[5-(2-hydroxyethyl)-2-(methyloxy)phenyl]-5-methyl-1H-1,2,3-triazole-4-carboxamide | | methyl [3-[({1-[(3,4-dichlorophenyl)methyl]-5-methyl-1H-1,2,3-triazol-4-yl}carbonyl)amino]-4-(methyloxy)phenyl]acetate (Example 35) | HRMS calculated for $C_{20}H_{20}Cl_2N_4O_3$<br>Theo: 435.0991<br>Found: 435.0975<br>Rt: 3.01 min.<br>MP: 138° C. |
| Example 55<br>1-[(3,4-Dichlorophenyl)methyl]-N-[2-fluoro-5-(hydroxymethyl)phenyl]-5-methyl-1H-1,2,3-triazole-4-carboxamide | | methyl 3-[({1-[(3,4-dichlorophenyl)methyl]-5-methyl-1H-1,2,3-triazol-4-yl}carbonyl)amino]-4-fluorobenzoate (Example 36) | HRMS calculated for $C_{18}H_{15}Cl_2FN_4O_2$<br>Theo: 409.0634<br>Found: 409.0624<br>Rt: 2.92 min.<br>MP: 210.5° C. |
| Example 56<br>N-[2-Chloro-5-(hydroxymethyl)phenyl]-1-[(3,4-dichlorophenyl)methyl]-5-methyl-1H-1,2,3-triazole-4-carboxamide | | methyl 4-chloro-3-[({1-[(3,4-dichlorophenyl)methyl]-5-methyl-1H-1,2,3-triazol-4-yl}carbonyl)amino]benzoate (Example 34) | HRMS calculated for $C_{18}H_{15}Cl_3N_4O_2$<br>Theo: 425.0339<br>Found: 425.0339<br>Rt: 3.11 min.<br>MP: 220° C. |

TABLE 15-continued

| Compound | Structure | From | Physical data |
| --- | --- | --- | --- |
| Example 57<br>1-[(3,5-Dichlorophenyl) methyl]-N-[5-(hydroxymethyl)-2-(methyloxy)phenyl]-5-methyl-1H-1,2,3-triazole-4-carboxamide | | methyl 3-[({1-[(3,5-dichlorophenyl) methyl]-5-methyl-1H-1,2,3-triazol-4-yl}carbonyl)amino]-4-(methyloxy) benzoate (Example 41) | HRMS calculated for $C_{19}H_{18}Cl_2N_4O_3$<br>Theo: 421.0834<br>Found: 421.0807<br>Rt: 2.99 min.<br>MP: 214° C. |
| Example 58<br>N-[3,4-bis(Hydroxymethyl) phenyl]-1-[(3,4-dichlorophenyl)methyl]-5-methyl-1H-1,2,3-triazole-4-carboxamide | | dimethyl 4-[({1-[(3,4-dichlorophenyl) methyl]-5-methyl-1H-1,2,3-triazol-4-yl}carbonyl)amino]-1,2-benzene dicarboxylate (Example 46) | HRMS calculated for $C_{19}H_{18}Cl_2N_4O_3$<br>Theo: 421.0834<br>Found: 421.0875<br>Rt: 2.60 min.<br>MP: 203° C. |
| Example 59<br>1-[(3,5-Dichlorophenyl)methyl]-N-[4-fluoro-3-(hydroxymethyl) phenyl]-5-methyl-1H-1,2,3-triazole-4-carboxamide | | methyl 5-[({1-[(3,5-dichlorophenyl) methyl]-5-methyl-1H-1,2,3-triazol-4-yl}carbonyl)amino]-2-fluorobenzoate (Example 47) | HRMS calculated for $C_{18}H_{15}Cl_2FN_4O_2$<br>Theo: 409.0634<br>found: 409.0630<br>Rt: 2.92 min.<br>MP: 178° C. |
| Example 60<br>N-[3,5-bis(Hydroxymethyl) phenyl]-5-methyl-1-(phenylmethyl)-1H-1,2,3-triazole-4-carboxamide | | dimethyl 5-({[5-methyl-1-(phenylmethyl)-1H-1,2,3-triazol-4-yl]carbonyl}amino)-1,3-benzene dicarboxylate (Intermediate 15) | HRMS calculated for $C_{19}H_{20}N_4O_3$<br>Theo: 353.1613<br>Found: 353.1628<br>Rt: 2.21 min.<br>MP: 148.2° C. |
| Example 61-[3,5-bis(Hydroxymethyl) phenyl]-1-[(3-chlorophenyl)methyl]-5-methyl-1H-1,2,3-triazole-4-carboxamide | | dimethyl 5-[({1-[(3-chlorophenyl)methyl]-5-methyl-1H-1,2,3-triazol-4-yl}carbonyl)amino]-1,3-benzene dicarboxylate (Intermediate 16) | HRMS calculated for $C_{19}H_{19}ClN_4O_3$<br>Theo: 387.1224<br>Found: 387.1198<br>Rt: 2.37 min.<br>MP: 192.7° C. |

TABLE 15-continued

| Compound | Structure | From | Physical data |
|---|---|---|---|
| Example 62<br>1-[(3,4-Dichlorophenyl)methyl]-N-[3-(2-hydroxyethyl)phenyl]-5-methyl-1H-1,2,3-triazole-4-carboxamide | | methyl {3-[({1-[(3,4-dichlorophenyl)methyl]-5-methyl-1H-1,2,3-triazol-4-yl}carbonyl)amino]phenyl}acetate (Example 30) | HRMS calculated for $C_{19}H_{18}Cl_2N_4O_2$<br>Theo: 405.0885<br>Found: 405.0869<br>Rt: 2.84 min.<br>MP: 142° C. |

Example 63
3-[({1-[(3,4-Dichlorophenyl)methyl]-5-methyl-1H-1,2,3-triazol-4-yl}carbonyl)amino]benzoic acid

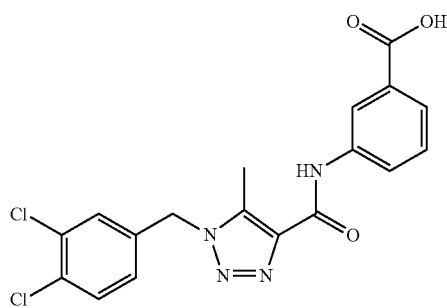 [SMILES: Cc1c(C(=O)Nc2cccc(C(=O)O)c2)nnn1Cc1ccc(Cl)c(Cl)c1]

A mixture of ethyl 3-[({1-[(3,4-dichlorophenyl)methyl]-5-methyl-1H-1,2,3-triazol-4-yl}carbonyl)amino]benzoate (Example 20) (0.06 g, 0.138 mmol) and a 1N NaOH solution (2 mL, 2 mmol) in ethanol (5 mL) was stirred at 40° C. for 4 hours. The solvent was evaporated and the residue was acidified with a 1N HCl solution. The precipitate formed was filtered and dried. The title compound was obtained as a white solid (53 mg, 96%). HRMS calculated for $C_{18}H_{14}Cl_2N_4O_5$ (M+H)$^+$: 405.0521. found: 405.0520, Rt: 2.23 min. MP: 267.6° C.

The following compounds were similarly prepared by analogous method to that described for Example 63:

TABLE 16

| Compound | Structure | From | Physical data |
|---|---|---|---|
| Example 64<br>3-[({1-[(3,4-Dichlorophenyl)methyl]-5-methyl-1H-1,2,3-triazol-4-yl}carbonyl)amino]-4-(methyloxy)benzoic acid | | methyl 3-[({1-[(3,4-dichlorophenyl)methyl]-5-methyl-1H-1,2,3-triazol-4-yl}carbonyl)amino]-4-(methyloxy)benzoate (Example 25) | HRMS calculated for $C_{19}H_{16}Cl_2N_4O_4$<br>Theo: 435.0627<br>Found: 435.0630<br>Rt: 2.41min<br>MP: 243.9° C. |
| Example 65<br>5-({[5-Methyl-1-(phenylmethyl)-1H-1,2,3-triazol-4-yl]carbonyl}amino)-1,3-benzene dicarboxylic acid | | dimethyl 5-({[5-methyl-1-(phenylmethyl)-1H-1,2,3-triazol-4-yl]carbonyl}amino)-1,3-benzene dicarboxylate (Intermediate 15) | HRMS calculated for $C_{19}H_{16}N_4O_5$<br>Theo: 381.1199<br>Found: 381.1231<br>Rt: 1.59 min<br>MP: 307.2° C. |
| Example 66<br>4-[({1-[(3,4-Dichlorophenyl)methyl]-5-methyl-1H-1,2,3-triazol-4-yl}carbonyl)amino]benzoic acid | | ethyl 4-[({1-[(3,4-dichlorophenyl)methyl]-5-methyl-1H-1,2,3-triazol-4-yl}carbonyl)amino]benzoate (Example 48) | HRMS calculated for $C_{18}H_{14}Cl_2N_4O_3$<br>Theo: 405.0521<br>Found: 405.0531<br>Rt: 2.33 min<br>MP >260° C. |

Example 67

1-[(3,4-Dichlorophenyl)methyl]-N-{3-[(ethylamino)carbonyl]phenyl}-5-methyl-1H-1,2,3-triazole-4-carboxamide

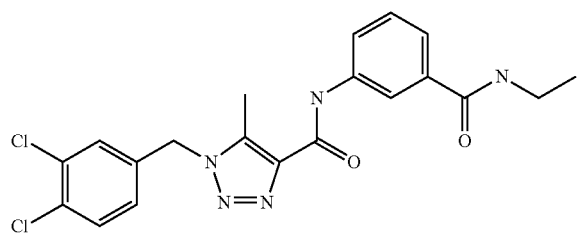 [SMILES: CCNC(=O)c1cccc(NC(=O)c2nnn(Cc3ccc(Cl)c(Cl)c3)c2C)c1]

A mixture of 3-[({1-[(3,4-dichlorophenyl)methyl]-5-methyl-1H-1,2,3-triazol-4-yl}carbonyl)amino]benzoic acid (Example 63) (0.143 g, 0.35 mmol), ethylamine in THF, 2M solution (1.75 mL, 0.35 mmol), HATU (0.199 g, 0.52 mmol) and DIPEA (0.09 mL, 0.52 mmol) in DMF was stirred at 40° C. for 1 week. The solvent was evaporated and the residue was washed with water and extracted with DCM. The organic phase was dried over sodium sulphate, filtered and concentrated. The title compound was obtained after recrystallisation from acetonitrile as white solid (49 mg, 32%). HRMS calculated for $C_{20}H_{19}Cl_2N_5O_2$ (M+H)$^+$ 432.0994. found: 432.0957, Rt: 2.82 min. MP: 192.2° C.

The following compounds were similarly prepared by analogous method to that described for Example 67:

Example 70

{3-[({1-[(3,4-Dichlorophenyl)methyl]-5-methyl-1H-1,2,3-triazol-4-yl}carbonyl)amino]phenyl}methyl acetate

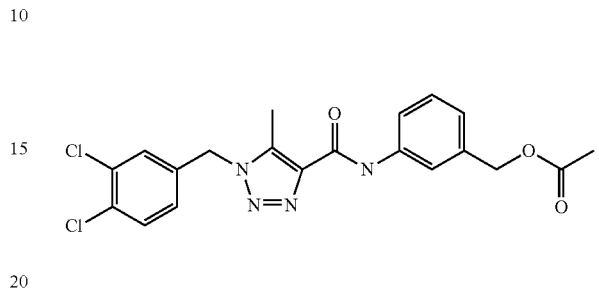

To a solution of 1-[(3,4-dichlorophenyl)methyl]-N-[3-(hydroxymethyl)phenyl]-5-methyl-1H-1,2,3-triazole-4-carboxamide (Example 24) (0.1 g, 0.25 mmol) in a mixture of DCM/THF were added NEt$_3$ (75 µL, 2 eq) and acetyl chloride (25 µL, 1.2 eq). The reaction was stirred at room temperature for 2 hours. Water was added and the product was extracted with ether, dried over sodium sulphate and evaporated in vacuo. The title compound was obtained as a white solid after recrystallisation from isopropyl ether (a couple drops of DCM) (60 mg, 54.5%). HRMS calculated for $C_{20}H_{18}Cl_2N_4O_3$ (M+H)$^+$433.0834. found: 433.0812, Rt: 3.14 min. MP: >70° C. (sticky).

The following compounds were similarly prepared by a method analogous to that described for Example 70:

TABLE 17

| Compound | Structure | From | Physical data |
| --- | --- | --- | --- |
| Example 68<br>1-[(3,4-Dichlorophenyl)methyl]-N-(3-{[(2-hydroxyethyl)amino]carbonyl}phenyl)-5-methyl-1H-1,2,3-triazole-4-carboxamide | 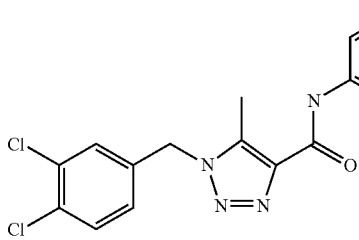 | 3-[({1-[(3,4-dichlorophenyl)methyl]-5-methyl-1H-1,2,3-triazol-4-yl}carbonyl)amino]benzoic acid (Example 63) and 2-aminoethanol | HRMS calculated for $C_{20}H_{19}Cl_2N_5O_3$<br>Theo: 448.0943<br>Found: 448.0940<br>Rt: 2.57 min.<br>MP: 190.7° C. |
| Example 69<br>1-[(3,4-Dichlorophenyl)methyl]-5-methyl-N-[5-[(methylamino)carbonyl]-2-(methyoxy)phenyl]-1H-1,2,3-triazole-4-carboxamide | 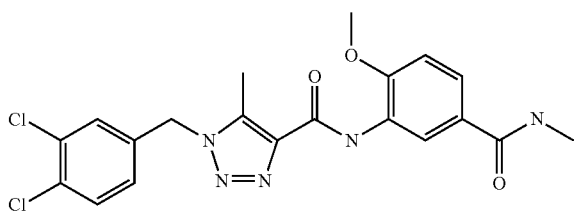 [SMILES: CNC(=O)c1ccc(OC)c(NC(=O)c2nnn(Cc3ccc(Cl)c(Cl)c3)c2C)c1] | 3-[({1-[(3,4-dichlorophenyl)methyl]-5-methyl-1H-1,2,3-triazol-4-yl}carbonyl)amino]-4-(methyloxy)benzoic acid (Example 64) and methyl amine | HRMS calculated for $C_{20}H_{19}Cl_2N_5O_3$<br>Theo: 448.0943<br>Found: 448.0935<br>Rt: 2.87 min.<br>MP: 222.2° C. |

TABLE 18

| Compound | Structure | From | Physical data |
|---|---|---|---|
| Example 71 {3-[({1-[(3,5-Dichlorophenyl)methyl]-5-methyl-1H-1,2,3-triazol-4-yl}carbonyl)amino]phenyl}methyl acetate | 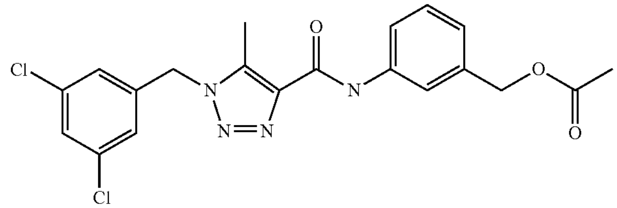 [SMILES: CC(=O)OCc1cccc(NC(=O)c2nnn(Cc3cc(Cl)cc(Cl)c3)c2C)c1] | 1-[(3,5-dichlorophenyl)methyl]-N-[3-(hydroxymethyl)phenyl]-5-methyl-1H-1,2,3-triazole-4-carboxamide (Example 40) | HRMS calculated for $C_{20}H_{18}Cl_2N_4O_3$ Theo: 433.0834 Found: 433.0801 Rt: 3.24 min. MP: 124° C. |
| Example 72 {3-[({1-[(3,4-Dichlorophenyl)methyl]-5-methyl-1H-1,2,3-triazol-4-yl}carbonyl)amino]phenyl}methyl benzoate | 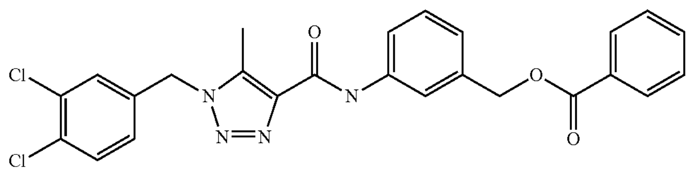 [SMILES: Cc1c(C(=O)Nc2cccc(COC(=O)c3ccccc3)c2)nnn1Cc1ccc(Cl)c(Cl)c1] | 1-[(3,4-dichlorophenyl)methyl]-N-[3-(hydroxymethyl)phenyl]-5-methyl-1H-1,2,3-triazole-4-carboxamide (Example 24) and benzoyl chloride | HRMS calculated for $C_{25}H_{20}Cl_2N_4O_3$ Theo: 495.0991 Found: 495.0982 Rt: 3.58 min. MP: 140° C. |
| Example 73 {3-[({1-[(3,5-Dichlorophenyl)methyl]-5-methyl-1H-1,2,3-triazol-4-yl}carbonyl)amino]phenyl}methyl benzoate | 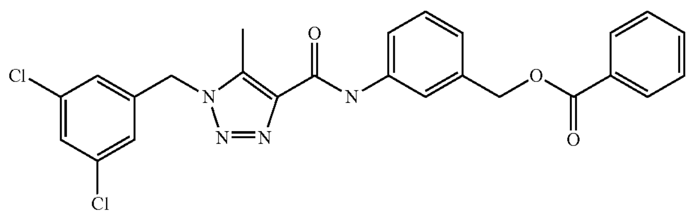 [SMILES: Cc1c(C(=O)Nc2cccc(COC(=O)c3ccccc3)c2)nnn1Cc1cc(Cl)cc(Cl)c1] | 1-[(3,5-dichlorophenyl)methyl]-N-[3-(hydroxymethyl)phenyl]-5-methyl-1H-1,2,3-triazole-4-carboxamide (Example 40) and benzoyl chloride | HRMS calculated for $C_{25}H_{20}Cl_2N_4O_3$ Theo: 495.0991 Found: 495.1003 Rt: 3.71 min. MP: 85-95° C. |

Example 74

1-[(3,4-Dichlorophenyl)methyl]-N-{4-[(2-hydroxyethyl)oxy]phenyl}-5-methyl-1H-1,2,3-triazole-4-carboxamide

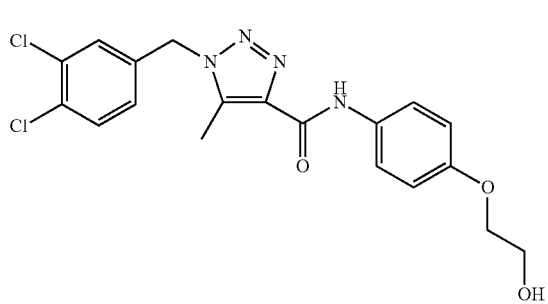 [SMILES: Cc1c(C(=O)Nc2ccc(OCCO)cc2)nnn1Cc1ccc(Cl)c(Cl)c1]

To a solution of the crude 1-[(3,4-dichlorophenyl)methyl]-5-methyl-N-(4-{[2-(tetrahydro-2H-pyran-2-yloxy)ethyl]oxy}phenyl)-1H-1,2,3-triazole-4-carboxamide (Intermediate 19) in methanol was added a saturated solution of HCl in ethyl acetate. The reaction was stirred to 60° C. for 18 hours. After evaporation, the title compound was obtained as a cream solid after recrystallisation from methanol (0.23 g, 54% from intermediate 6). HRMS calculated for $C_{19}H_{18}Cl_2N_4O_3$ (M+H)$^+$ 421.0834. found: 421.0837, Rt: 2.76 min. MP: 140° C.

Example 75

1-[(3,4-Dichlorophenyl)methyl]-5-methyl-N-[4-(1-methylethenyl)-2-(methyloxy)phenyl]-1H-1,2,3-triazole-4-carboxamide

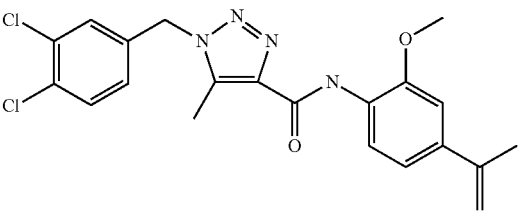 [SMILES: C=C(C)c1ccc(NC(=O)c2nnn(Cc3ccc(Cl)c(Cl)c3)c2C)c(OC)c1]

To a solution of methyl 4-[({1-[(3,4-dichlorophenyl)methyl]-5-methyl-1H-1,2,3-triazol-4-yl}carbonyl)amino]-3-(methyloxy)benzoate (Example 17) (0.2 g, 0.45 mmol) in THF (30 mL) was added a 1M solution of methyl magnesium bromide in THF (5 eq). The reaction was stirred at room temperature for 2 hours and heated to 60° C. for 2 hours. After cooling, water was added followed by a 1N HCl solution and the compound was extracted with ether, dried over sodium sulphate and evaporated. After purification by flash chromatography eluting with DCM and DCM/MeOH 92/8, the title compound was obtained as a white solid (0.02 g, 10%). HRMS calculated for $C_{21}H_{20}Cl_2N_4O_2$ (M+H)$^+$431.1042. found: 431.1028, Rt: 3.69 min. MP: 170° C.

The following compounds were similarly prepared by analogous method to that described for Example 75:

TABLE 19

| Compound | Structure | From | Physical data |
|---|---|---|---|
| Example 76<br>1-[(3,4-Dichlorophenyl)methyl]-N-[3-(1-hydroxy-1-methylethyl)phenyl]-5-methyl-1H-1,2,3-triazole-4-carboxamide | 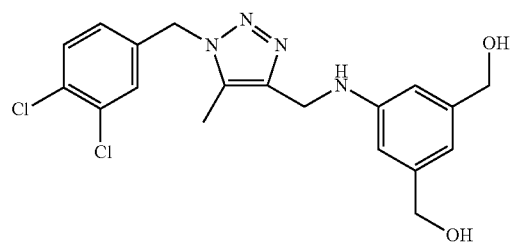 | ethyl 3-[({1-[(3,4-dichlorophenyl)methyl]-5-methyl-1H-1,2,3-triazol-4-yl}carbonyl)amino]benzoate (Example 20) | HRMS calculated for $C_{20}H_{20}Cl_2N_4O_2$<br>Theo: 417.0885<br>Found: 417.0886<br>Rt: 2.95 min.<br>MP: 58° C. |

Example 77

1-[(3,4-Dichlorophenyl)methyl]-N-[4-{[2-(dimethylamino)ethyl]oxy}-3-(hydroxymethyl)phenyl]-5-methyl-1H-1,2,3-triazole-4-carboxamide

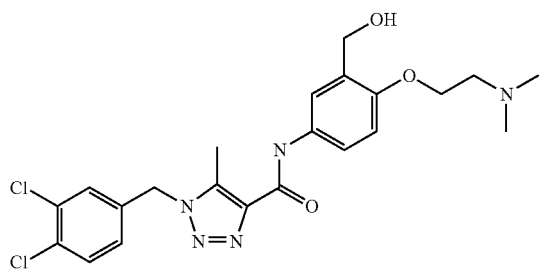 [SMILES: Cc1c(C(=O)Nc2ccc(OCCN(C)C)c(CO)c2)nnn1Cc1ccc(Cl)c(Cl)c1]

To a solution of 1-[(3,4-dichlorophenyl)methyl]-N-[4-hydroxy-3-(hydroxymethyl)phenyl]-5-methyl-1H-1,2,3-triazole-4-carboxamide (Example 26) (0.1 g, 0.245 mmol) in DMF (10 mL), were added potassium carbonate (0.07 g, 2 eq) and (2-chloroethyl)dimethylamine hydrochloride (0.07 g, 2 eq). The reaction was heated at 40° C. for 3 days. After evaporation, the residue was diluted with DCM, washed with water and dried over sodium sulphate. After purification by flash chromatography eluting with DCM/MeOH (90/10) and recrystallisation from methanol, the title compound was obtained as a white solid (18 mg, 16%). HRMS calculated for $C_{22}H_{25}Cl_2N_5O_3$ $(M+H)^+$ 478.1413. found: 478.1435, Rt: 2.47 min. MP: 163.1° C.

Example 78

1-[(3,4-Dichlorophenyl)methyl]-N-{3-[(2-hydroxyethyl)oxy]phenyl}-5-methyl-1H-1,2,3-triazole-4-carboxamide

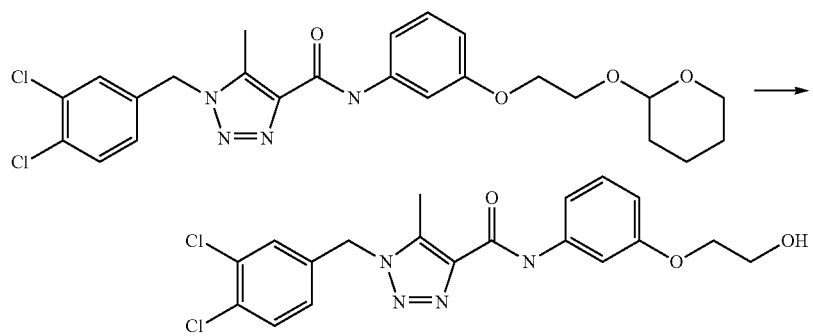

To a solution of 1-[(3,4-dichlorophenyl)methyl]-N-(3-hydroxyphenyl)-5-methyl-1H-1,2,3-triazole-4-carboxamide (Example 31) (0.1 g, 0.29 mmol) in acetonitrile (10 mL) and a couple of drops of DMF, were added 2-[(2-bromoethyl)oxy]tetrahydro-2H-pyran (0.09 µl, 2 eq) and potassium carbonate (0.08 g, 2 eq). The reaction was heated at 40° C. for 1 week. After evaporation, the residue was dissolved in DCM, washed with water and dried over sodium sulphate. After purification by flash chromatography eluting with DCM/MeOH, 98/2, the crude compound was dissolved in MeOH and some drops of a concentrated HCl solution in AcOEt were added and the solution was stirred at room temperature for 3 hours. After evaporation, the compound was recrystallised (twice) from methanol and washed with a mixture of ether and pentane. The title compound was obtained as a green solid (45 mg, 36%). HRMS calculated for $C_{19}H_{18}Cl_2N_4O_3$ $(M+H)^+$ 421.0834. found: 421.0804, Rt: 2.87 min. MP: 144.9° C.

Example 79

{5-[({1-[(3,4-Dichlorophenyl)methyl]-5-methyl-1H-1,2,3-triazol-4-yl}methyl)amino]benzene-1,3-diyl}dimethanol This compound was obtained as a by product of the reduction of dimethyl 5-[({1-[(3,4-dichlorophenyl)methyl]-5-methyl-1H-1,2,3-triazol-4-yl}carbonyl)amino]-1,3-benzenedicarboxylate (Intermediate 14) in the preparation of N-[3,5- bis(hydroxymethyl)phenyl]-1-[(3,4-dichlorophenyl)methyl]-5-methyl-1H-1,2,3-triazole-4-carboxamide (Example 52). It was obtained as a white solid (5%) via recrystallisation from acetonitrile. HRMS calculated for $C_{19}H_{20}Cl_2N_4O_2$ (M+H)$^+$ 407.1042. found: 407.1022, Rt: 2.40 min. MP: 120° C.

The following compounds were similarly prepared by analogous method to that described for Example 49:

TABLE 20

| Compound | Structure | From | Physical data |
| --- | --- | --- | --- |
| Example 80 N-[3,4-bis(Hydroxymethyl)phenyl]-5-methyl-1-(phenylmethyl)-1H-1,2,3-triazole-4-carboxamide | 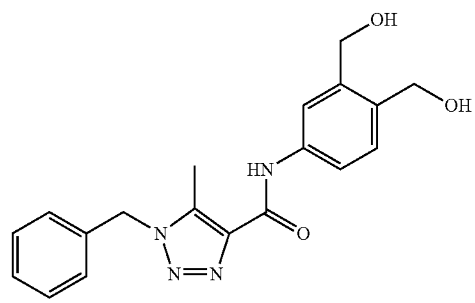 [SMILES: Cc1c(C(=O)Nc2ccc(CO)c(CO)c2)nnn1Cc1ccccc1] | dimethyl 4-({[5-methyl-1-(phenylmethyl)-1H-1,2,3-triazol-4-yl]carbonyl}amino)-1,2-benzene dicarboxylate (Intermediate 20) | HRMS calculated for $C_{19}H_{20}N_4O_3$ Theo: 353.1613 Found: 353.1593 Rt: 2.23 min. MP: 171.4° C. |
| Example 81 N-[3,5-bis(Hydroxymethyl)phenyl]-1-[(4-fluorophenyl)methyl]-5-methyl-1H-1,2,3-triazole-4-carboxamide | 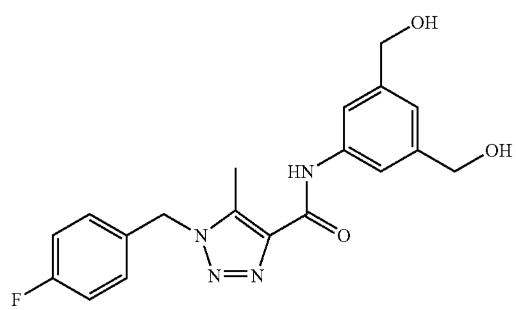 [SMILES: Cc1c(C(=O)Nc2cc(CO)cc(CO)c2)nnn1Cc1ccc(F)cc1] | dimethyl 5-[({1-[(4-fluorophenyl)methyl]-5-methyl-1H-1,2,3-triazol-4-yl}carbonyl)amino]-1,3-benzene dicarboxylate (Intermediate 21) | HRMS calculated for $C_{19}H_{19}FN_4O_3$ Theo: 371.1519 Found: 371.1537 Rt: 2.22 min. MP: 180.3° C. |
| Example 82 N-[3,4-bis(Hydroxymethyl)phenyl]-1-[(3-chlorophenyl)methyl]-5-methyl-1H-1,2,3-triazole-4-carboxamide | 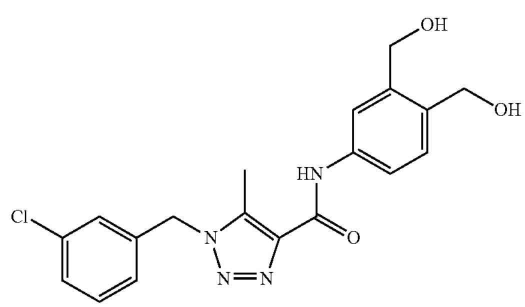 [SMILES: Cc1c(C(=O)Nc2ccc(CO)c(CO)c2)nnn1Cc1cccc(Cl)c1] | dimethyl 4-[({1-[(3-chlorophenyl)methyl]-5-methyl-1H-1,2,3-triazol-4-yl}carbonyl)amino]-1,2-benzene dicarboxylate (Intermediate 22) | HRMS calculated for $C_{19}H_{19}ClN_4O_3$ Theo: 387.1224 Found: 387.1223 Rt: 2.41 min. MP: 157° C. |
| Example 83 N-[3,4-bis(Hydroxymethyl)phenyl]-1-[(4-fluorophenyl)methyl]-5-methyl-1H-1,2,3-triazole-4-carboxamide | 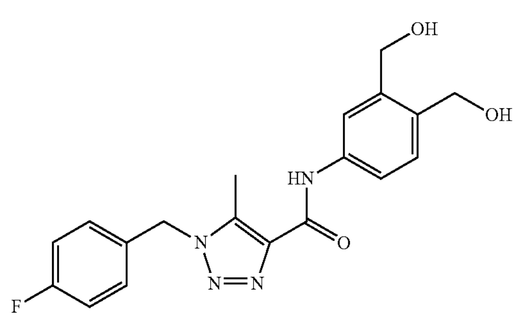 [SMILES: Cc1c(C(=O)Nc2ccc(CO)c(CO)c2)nnn1Cc1ccc(F)cc1] | dimethyl 4-[({1-[(4-fluorophenyl)methyl]-5-methyl-1H-1,2,3-triazol-4-yl}carbonyl)amino]-1,2-benzene dicarboxylate (Intermediate 23) | HRMS calculated for $C_{19}H_{19}FN_4O_3$ Theo: 371.1519 Found: 371.1544 Rt: 2.29 min. MP: 175.5° C. |

TABLE 20-continued

| Compound | Structure | From | Physical data |
|---|---|---|---|
| Example 84<br>N-[3,5-bis(Hydroxymethyl)phenyl]-1-[(3-fluorophenyl)methyl]-5-methyl-1H-1,2,3-triazole-4-carboxamide | | dimethyl 5-[({1-[(3-fluorophenyl)methyl]-5-methyl-1H-1,2,3-triazol-4-yl}carbonyl)amino]-1,3-benzene dicarboxylate (Intermediate 27) | HRMS calculated for $C_{19}H_{19}FN_4O_3$<br>Theo: 369.1363<br>Found: 369.1342<br>Rt: 2.20 min.<br>MP: 173.1° C. |
| Example 85<br>N-[3,4-bis(Hydroxymethyl)phenyl]-1-[(3-fluorophenyl)methyl]-5-methyl-1H-1,2,3-triazole-4-carboxamide | | dimethyl 5-[({1-[(3-fluorophenyl)methyl]-5-methyl-1H-1,2,3-triazol-4-yl}carbonyl)amino]-1,3-benzene dicarboxylate (Intermediate 28) | HRMS calculated for $C_{19}H_{19}FN_4O_3$<br>Theo: 371.1519<br>Found: 371.1533<br>Rt: 2.15 min.<br>MP: 157.2° C. |

The following compounds were similarly prepared by analogous method to that described for Example 1:

TABLE 21

| Compound | Structure | From | Physical data |
|---|---|---|---|
| Example 86<br>1-[(3-Chlorophenyl)methyl]-N-[3-(hydroxymethyl)phenyl]-5-methyl-1H-1,2,3-triazole-4-carboxamide | | 1-[(3-chlorophenyl)methyl]-5-methyl-1H-1,2,3-triazole-4-carboxylic acid (Intermediate 13) and (3-aminophenyl)methanol | HRMS calculated for $C_{18}H_{17}ClN_4O_2$<br>Theo: 355.0962<br>Found: 355.0927<br>Rt: 2.64 min<br>MP: 151.9° C. |
| Example 87<br>1-[(4-Fluorophenyl)methyl]-N-[3-(hydroxymethyl)phenyl]-5-methyl-1H-1,2,3-triazole-4-carboxamide | | 1-[(4-fluorophenyl)methyl]-5-methyl-1H-1,2,3-triazole-4-carboxylic acid and (3-aminophenyl)methanol | HRMS calculated for $C_{18}H_{17}FN_4O_2$<br>Theo: 339.1257<br>Found: 339.1264<br>Rt: 2.67 min<br>MP: 142.1° C. |

TABLE 21-continued

| Compound | Structure | From | Physical data |
|---|---|---|---|
| Example 88<br>1-[(3-Chlorophenyl)methyl]-N-[4-(hydroxymethyl)phenyl]-5-methyl-1H-1,2,3-triazole-4-carboxamide | 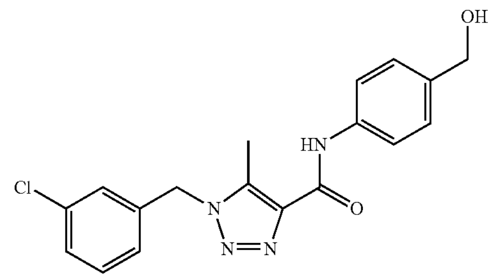 [SMILES: Cc1c(C(=O)Nc2ccc(CO)cc2)nnn1Cc1cccc(Cl)c1] | 1-[(3-chlorophenyl)methyl]-5-methyl-1H-1,2,3-triazole-4-carboxylic acid (Intermediate 13) and (4-aminophenyl)methanol | HRMS calculated for $C_{18}H_{17}ClN_4O_2$<br>Theo: 357.1118<br>Found: 357.1109<br>Rt: 2.74 min<br>MP: 136.2° C. |
| Example 89<br>1-[(3-Fluorophenyl)methyl]-N-[3-(hydroxymethyl)phenyl]-5-methyl-1H-1,2,3-triazole-4-carboxamide | 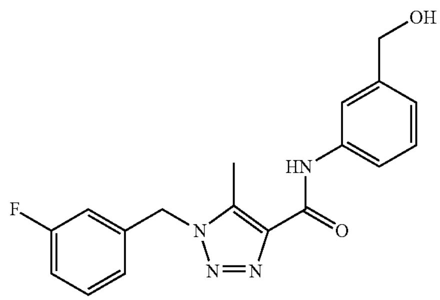 [SMILES: Cc1c(C(=O)Nc2cccc(CO)c2)nnn1Cc1cccc(F)c1] | 1-[(3-fluorophenyl)methyl]-5-methyl-1H-1,2,3-triazole-4-carboxylic acid (Intermediate 26) and (3-aminophenyl)methanol | HRMS calculated for $C_{18}H_{17}FN_4O_2$<br>$(M - H)^+$<br>Theo: 339.1257<br>Found: 339.1272<br>Rt: 2.64 min<br>MP: 124.7° C. |
| Example 90<br>1-[(4-Fluorophenyl)methyl]-N-[4-(hydroxymethyl)phenyl]-5-methyl-1H-1,2,3-triazole-4-carboxamide | 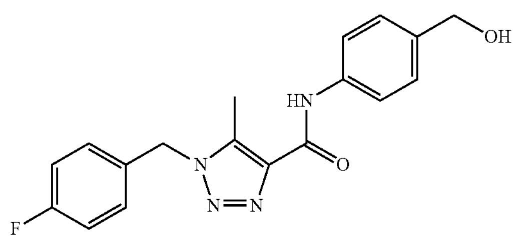 [SMILES: Cc1c(C(=O)Nc2ccc(CO)cc2)nnn1Cc1ccc(F)cc1] | 1-[(4-fluorophenyl)methyl]-5-methyl-1H-1,2,3-triazole-4-carboxylic acid and (4-aminophenyl)methanol | HRMS calculated for $C_{18}H_{17}FN_4O_2$<br>Theo: 341.1414<br>Found: 341.1434<br>Rt: 2.61 min<br>MP: 145.6° C. |
| Example 91<br>1-[(3-Fluorophenyl)methyl]-N-[4-(hydroxymethyl)phenyl]-5-methyl-1H-1,2,3-triazole-4-carboxamide | 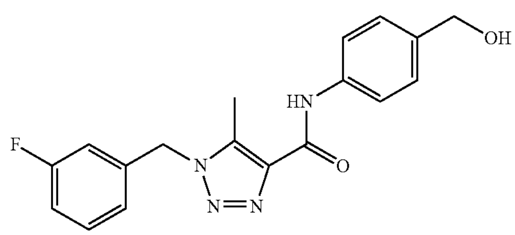 [SMILES: Cc1c(C(=O)Nc2ccc(CO)cc2)nnn1Cc1cccc(F)c1] | 1-[(3-fluorophenyl)methyl]-5-methyl-1H-1,2,3-triazole-4-carboxylic acid (Intermediate 26) and (4-aminophenyl)methanol | HRMS calculated for $C_{18}H_{17}FN_4O_2$<br>Theo: 341.1414<br>Found: 341.1427<br>Rt: 2.57 min<br>MP: 134.3° C. |

Example 92

1-[(3,4-Dichlorophenyl)methyl]-N-{3-(hydroxymethyl)-5-[(methylamino)carbonyl]phenyl}-5-methyl-1H-1,2,3-triazole-4-carboxamide

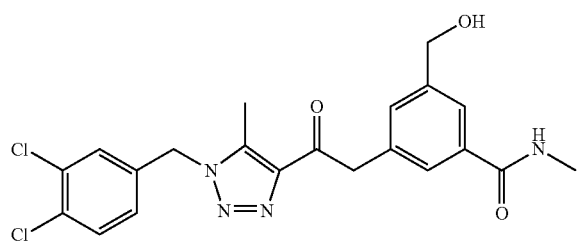 [SMILES: CNC(=O)c1cc(CO)cc(CC(=O)c2nnn(Cc3ccc(Cl)c(Cl)c3)c2C)c1]

To a solution of methyl 3-[({1-[(3,4-dichlorophenyl)methyl]-5-methyl-1H-1,2,3-triazol-4-yl}carbonyl)amino]-5-[(methylamino)carbonyl]benzoate (intermediate 31) (0.206 g, 0.43 mmol) in THF (5 mL), was added a 1M solution of LiAlH$_4$ in THF (0.65 mL, 1.5 eq.). The reaction was stirred at RT for one night. Water was added and the compound was extracted with AcOEt, dried over sodium sulfate and concentrated in vacuo. After trituration from hot methanol, filtration and dry, the title compound was obtained as a white solid (0.03 g, 15.8%). HRMS calculated for $C_{20}H_{19}Cl_2N_5O_3$ $(M+H)^+$ 448.0943. found: 448.0910, Rt: 2.66 min. MP: 223-225° C.

The following compound was similarly prepared by analogous method to that described for Example 49:

TABLE 22

| Compound | Structure | From | Physical data |
|---|---|---|---|
| Example 93 N-{1-[(3,4-Dichlorophenyl)methyl]-5-methyl-1H-1,2,3-triazol-4-yl}-4-(hydroxymethyl)benzamide | 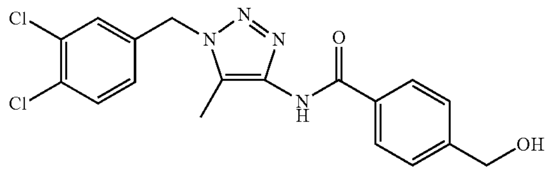 [SMILES: Cc1c(NC(=O)c2ccc(CO)cc2)nnn1Cc1ccc(Cl)c(Cl)c1] | methyl 4-[({1-[(3,4-dichlorophenyl)methyl]-5-methyl-1H-1,2,3-triazol-4-yl}amino)carbonyl]benzoate (Intermediate 34) | HRMS calculated for $C_{18}H_{16}Cl_2N_4O_2$ Theo: 391.0728 Found: 391.0740 Rt: 2.47 min. MP: 160° C. |

Biological Assay

The compounds of the present invention may be analysed in vitro for SCD activity using an assay based on the production of [$^3$H]H$_2$O, which is released during the enzyme-catalyzed generation of the monounsaturated fatty acyl CoA product. The assay is performed in a 96-well filtration plates. The titrated substrate used in the assay is the [9,10-$^3$H] stearoyl Coenzyme A. After incubation for 6 minutes of SCD-containing rat microsomes (2 μg protein) and substrate (1 μM), the labelled fatty acid acyl-CoA species and microsomes are absorbed with charcoal and separated from [$^3$H]H$_2$O by centrifugation. The formation of [$^3$H]H$_2$O is used as a measure of SCD activity. Compounds at concentrations starting at 10 μM to 0.1 nM or vehicle (DMSO) are preincubated for 5 minutes with the microsomes before addition of the substrate. The concentration-responses are fitted with sigmoidal curves to obtain IC$_{50}$ values.

All of the synthetic Example compounds I-93 tested by the above described in vitro assay for SCD activity were found to exhibit an average pIC$_{50}$ value of greater than 5.5.

The following compounds were also prepared and when tested by the above described in vitro assay for SCD activity were found to exhibit an average pIC$_{50}$ value of less than 5.

| Name | Structure |
|---|---|
| 1-(4-Biphenylylmethyl)-5-methyl-N-{4-[(3-methylbutyl)oxy]phenyl}-1H-1,2,3-triazole-4-carboxamide | 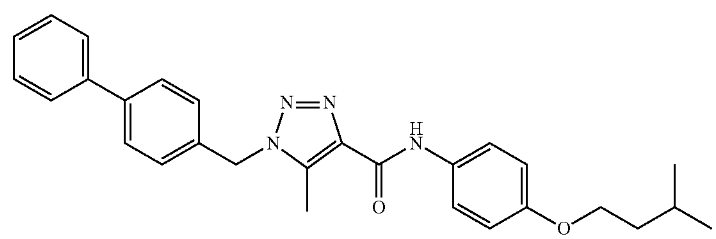 [SMILES: Cc1c(C(=O)Nc2ccc(OCCC(C)C)cc2)nnn1Cc1ccc(-c2ccccc2)cc1] |
| N-[3,4-Bis(methyloxy)phenyl]-5-methyl-1-{[4-(1-methylethyl)phenyl]methyl}-1H-1,2,3-triazole-4-carboxamide | 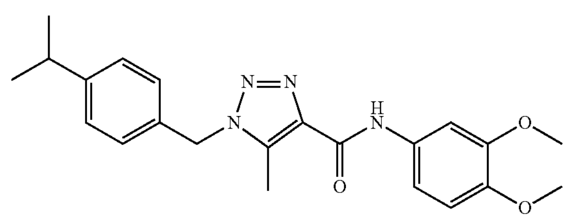 [SMILES: COc1ccc(NC(=O)c2nnn(Cc3ccc(C(C)C)cc3)c2C)cc1OC] |
| Methyl 5-[({1-[(3,4-dichlorophenyl)methyl]-5-methyl-1H-1,2,3-triazol-4-yl}carbonyl)amino]-2-(methyloxy)benzoate | 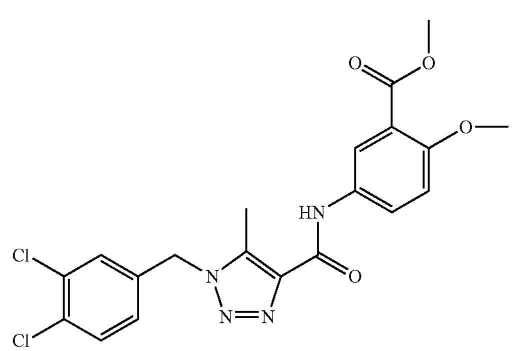 [SMILES: COC(=O)c1cc(NC(=O)c2nnn(Cc3ccc(Cl)c(Cl)c3)c2C)ccc1OC] |

| Name | Structure |
|---|---|
| Dimethyl 5-({[5-methyl-1-(phenylmethyl)-1H-1,2,3-triazol-4-yl]carbonyl}amino)-1,3-benzenedicarboxylate | 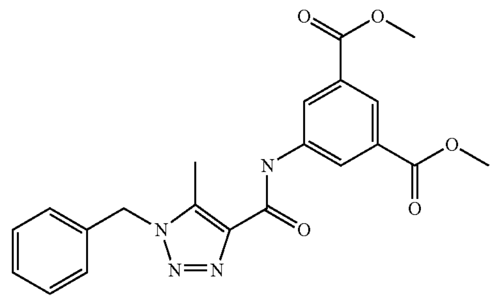 [SMILES: COC(=O)c1cc(NC(=O)c2nnn(Cc3ccccc3)c2C)cc(C(=O)OC)c1] |
| Dimethyl 5-[({1-[(3-chlorophenyl)methyl]-5-methyl-1H-1,2,3-triazol-4-yl}carbonyl)amino]-1,3-benzenedicarboxylate | 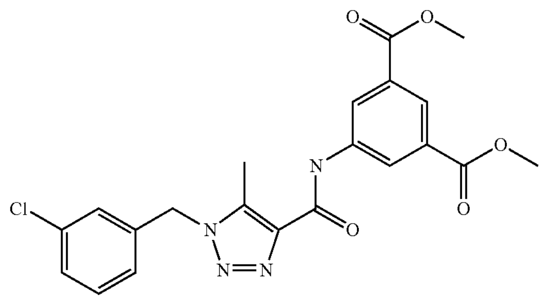 [SMILES: COC(=O)c1cc(NC(=O)c2nnn(Cc3cccc(Cl)c3)c2C)cc(C(=O)OC)c1] |
| 5-[({1-[(3-Chlorophenyl)methyl]-5-methyl-1H-1,2,3-triazol-4-yl}carbonyl)amino]-1,3-benzenedicarboxylic acid | 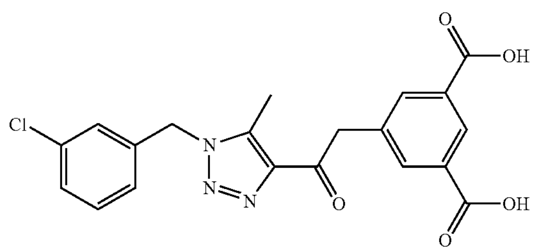 [SMILES: Cc1c(C(=O)Cc2cc(C(=O)O)cc(C(=O)O)c2)nnn1Cc1cccc(Cl)c1] |
| Methyl 3-[({1-[(3,4-dichlorophenyl)methyl]-5-methyl-1H-1,2,3-triazol-4-yl}carbonyl)amino]-2-methylbenzoate | 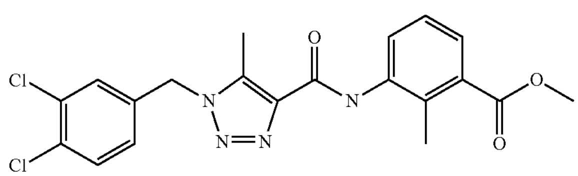 [SMILES: COC(=O)c1cccc(NC(=O)c2nnn(Cc3ccc(Cl)c(Cl)c3)c2C)c1C] |
| Dimethyl 5-[({1-[(3,4-dichlorophenyl)methyl]-5-methyl-1H-1,2,3-triazol-4-yl}carbonyl)amino]-1,3-benzenedicarboxylate | 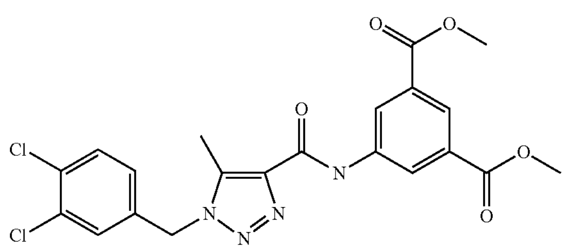 [SMILES: COC(=O)c1cc(NC(=O)c2nnn(Cc3ccc(Cl)c(Cl)c3)c2C)cc(C(=O)OC)c1] |
| 5-[({1-[(3,4-Dichlorophenyl)methyl]-5-methyl-1H-1,2,3-triazol-4-yl}carbonyl)amino]-N,N'-dimethyl-1,3-benzenedicarboxamide | 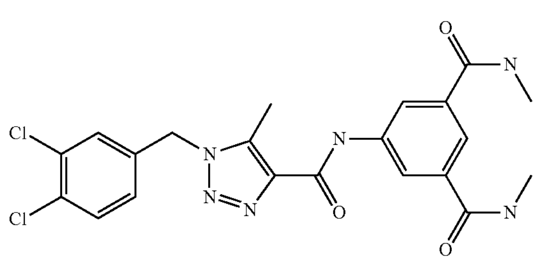 [SMILES: CNC(=O)c1cc(NC(=O)c2nnn(Cc3ccc(Cl)c(Cl)c3)c2C)cc(C(=O)NC)c1] |

| Name | Structure |
|---|---|
| Dimethyl 4-({[5-methyl-1-(phenylmethyl)-1H-1,2,3-triazol-4-yl]carbonyl}amino)-1,2-benzenedicarboxylate | 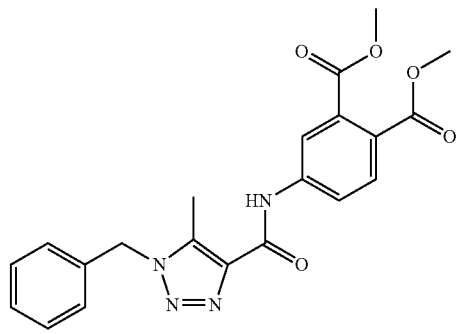 [SMILES: COC(=O)c1ccc(NC(=O)c2nnn(Cc3ccccc3)c2C)cc1C(=O)OC] |
| Dimethyl 5-[({1-[(4-fluorophenyl)methyl]-5-methyl-1H-1,2,3-triazol-4-yl}carbonyl)amino]-1,3-benzenedicarboxylate | 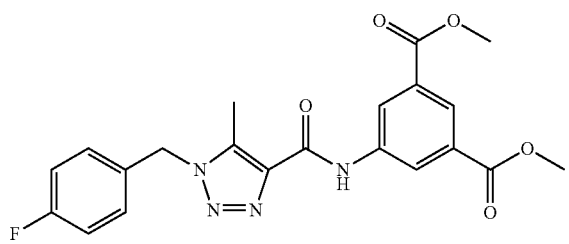 [SMILES: COC(=O)c1cc(NC(=O)c2nnn(Cc3ccc(F)cc3)c2C)cc(C(=O)OC)c1] |
| 1-[(3,4-dichlorophenyl)methyl]-5-methyl-N-{2-methyl-3-[(methylamino)carbonyl]phenyl}-1H-1,2,3-triazole-4-carboxamide | 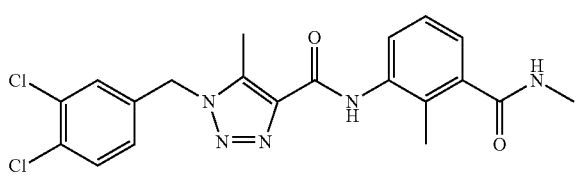 [SMILES: CNC(=O)c1cccc(NC(=O)c2nnn(Cc3ccc(Cl)c(Cl)c3)c2C)c1C] |

The following compounds were also prepared and when tested by the above described in vitro assay for SCD activity were found to exhibit an average pIC$_{50}$ value of between 5 and 5.5.

| Name | Structure |
|---|---|
| 1-[(4-fluorophenyl)methyl]-5-methyl-N-(5,6,7,8-tetrahydro-2-naphthalenyl)-1H-1,2,3-triazole-4-carboxamide | 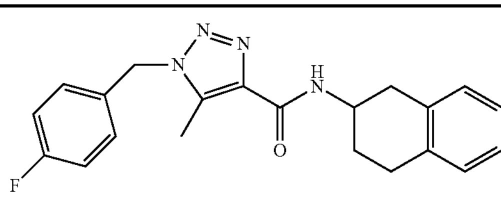 |

The invention claimed is:

1. A method of treating a disease or a condition susceptible to amelioration by an SCD inhibitor in a human in need thereof, comprising administering to said human an effective amount of a compound of formula (I) or a pharmaceutically acceptable salt thereof:

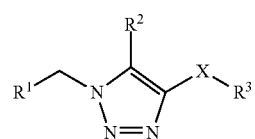

(I)

wherein:

X represents —CONH—, —NHCO— or —CH$_2$NH—;

R$^1$ represents a —C$_{6-10}$aryl optionally substituted by one, two or three groups independently selected from:
- (a) —C$_{1-6}$alkyl, —OCH$_3$, —C$_{1-6}$haloalkyl, —OC$_{1-6}$haloalkyl, —C$_{3-6}$cycloalkyl, —OC$_{3-6}$cycloalkyl or halogen;
- (b) phenyl optionally substituted by one, two or three groups independently selected from: halogen;

R$^2$ represents —C$_{1-6}$alkyl;

R$^3$ represents a —C$_{6-10}$aryl optionally substituted by one, two or three groups independently selected from:
- (a) —C$_{1-6}$alkyl, —C$_{1-6}$alkenyl, —C$_{1-6}$alkoxy, —O(CH$_2$)$_m$R$^4$, —(CH$_2$)$_m$OC(=O)R$^4$, —(CH$_2$)$_n$CO$_2$R$^5$, —(CH$_2$)$_n$OC(=O)R$^5$, —C$_{0-6}$alkylOH, —C(=O)NHR$^6$, —(CH$_2$)$_p$NHC(=O)R$^7$, —O(CH$_2$)$_q$NR$^8$R$^9$, —OC$_{1-6}$alkylOH, —C$_{1-6}$haloalkyl, —OC$_{1-6}$haloalkyl, —C$_{3-6}$cycloalkyl, —OC$_{3-6}$cycloalkyl or halogen;
- (b) oxazole;

R$^4$ represents —C$_{6-10}$aryl;

R$^5$ represents —H or —C$_{1-6}$alkyl;

R$^6$ represents —H or —C$_{1-3}$alkyl or —C$_{1-3}$alkylOH;

R$^7$ represents —H or —C$_{1-3}$alkyl;

R$^8$ represents —H or —C$_{1-3}$alkyl;

R$^9$ represents —H or —C$_{1-3}$alkyl;

m represents 1-3;

n represents 0-3;

p represents 0-3; and q represents 1-3;

or a pharmaceutically acceptable salt thereof.

2. The method according to claim 1 wherein X represents —CONH— or —CH$_2$NH—.

3. The method according to claim 1 wherein R$^1$ represents phenyl optionally substituted by one, two or three groups independently selected from
- (a) —C$_{1-6}$alkyl, —OCH$_3$, —C$_{1-6}$haloalkyl, —OC$_{1-6}$haloalkyl, —C$_{3-6}$cycloalkyl, —OC$_{3-6}$cycloalkyl or halogen;
- (b) phenyl optionally substituted by one, two or three groups independently selected from halogen; and wherein R$^3$ represents phenyl optionally substituted by one, two or three groups independently selected from
- (a) —C$_{1-6}$alkyl, —C$_{1-6}$alkenyl, —C$_{1-6}$alkoxy, —O(CH$_2$)$_m$R$^4$, —(CH$_2$)$_m$OC(=O)R$^4$, —(CH$_2$)$_n$CO$_2$R$^5$, —(CH$_2$)$_n$OC(=O)R$^5$, —C$_{0-6}$alkylOH, —C(=O)NHR$^6$, —(CH$_2$)$_p$NHC(=O)R$^7$, —O(CH$_2$)$_q$NR$^8$R$^9$, —OC$_{1-6}$alkylOH, —C$_{1-6}$haloalkyl, —OC$_{1-6}$haloalkyl, —C$_{3-6}$cycloalkyl, —OC$_{3-6}$cycloalkyl or halogen;
- (b) oxazole.

4. The method according to claim 3 wherein R$^2$ represents —C$_{1-3}$alkyl.

5. The method according to claim 1 wherein the compound of formula (I) is selected from the group consisting of:

N-[3,4-bis(methyloxy)phenyl]-1-[(4-fluorophenyl)methyl]-5-methyl-1H-1,2,3-triazole-4-carboxamide, N-[3,4-bis(methyloxy)phenyl]-1-[(4-bromophenyl)methyl]-5-methyl-1H-1,2,3-triazole-4-carboxamide, 1-[(4-Bromophenyl)methyl]-5-methyl-N-{4-[(phenylmethyl)oxy]phenyl}-1H-1,2,3-triazole-4-carboxamide, 1-[(4-Fluorophenyl)methyl]-5-methyl-N-{4-[(phenylmethyl)oxy]phenyl}-1H-1,2,3-triazole-4-carboxamide, 1-[(4-Fluorophenyl)methyl]-5-methyl-N-{4-[(3-methylbutyl)oxy]phenyl}-1H-1,2,3-triazole-4-carboxamide, 1-[(4-Bromophenyl)methyl]-5-methyl-N-{4-[(3-methylbutyl)oxy]phenyl}-1H-1,2,3-triazole-4-carboxamide, 5-Methyl-1-(phenylmethyl)-N-{4-[(phenylmethyl)oxy]phenyl}-1H-1,2,3-triazole-4-carboxamide, 5-Methyl-N-{4-[(3-methylbutyl)oxy]phenyl}-1-(phenylmethyl)-1H-1,2,3-triazole-4-carboxamide, 1-[(2'-Chloro-4-biphenylyl)methyl]-5-methyl-N-{4-[(3-methylbutyl)oxy]phenyl}-1H-1,2,3-triazole-4-carboxamide, 5-Methyl-N-{4-[(3-methylbutyl)oxy]phenyl}-1-[(4-methylphenyl)methyl]-1H-1,2,3-triazole-4-carboxamide, 5-Methyl-N-{4-[(3-methylbutyl)oxy]phenyl}-1-{[4-(1-methylethyl)phenyl]methyl}-1H-1,2,3-triazole-4-carboxamide, N-[3,4-Bis(methyloxy)phenyl]-5-methyl-1-[(4-methylphenyl)methyl]-1H-1,2,3-triazole-4-carboxamide, 1-(2-Biphenylylmethyl)-N-[3,4-bis(methyloxy)phenyl]-5-methyl-1H-1,2,3-triazole-4-carboxamide, 1-[(3,4-Dichlorophenyl)methyl]-5-methyl-N-[4-(1,3-oxazol-2-yl)phenyl]-1H-1,2,3-triazole-4-carboxamide, 1-[(3,4-Dichlorophenyl)methyl]-N-[4-(hydroxymethyl)phenyl]-5-methyl-1H-1,2,3-triazole-4-carboxamide, Methyl 4-[({1-[(3,4-dichlorophenyl)methyl]-5-methyl-1H-1,2,3-triazol-4-yl}carbonyl)amino]-3-(methyloxy)benzoate, 1-[(3,4-Dichlorophenyl)methyl]-5-methyl-N-{3-[(methylamino)carbonyl]phenyl}-1H-1,2,3-triazole-4-carboxamide, 1-[(3,4-Dichlorophenyl)methyl]-5-methyl-N-{4-[(methylamino)carbonyl]phenyl}-1H-1,2,3-triazole-4-carboxamide, Ethyl 3-[({1-[(3,4-dichlorophenyl)methyl]-5-methyl-1H-1,2,3-triazol-4-yl}carbonyl)amino]benzoate, N-[3-(acetylamino)phenyl]-1-[(3,4-dichlorophenyl)methyl]-5-methyl-1H-1,2,3-triazole-4-carboxamide, N-[4-(acetylamino)phenyl]-1-[(3,4-dichlorophenyl)methyl]-5-methyl-1H-1,2,3-triazole-4-carboxamide, 1-[(3,4-Dichlorophenyl)methyl]-N-[3-(hydroxymethyl)-2-methylphenyl]-5-methyl-1H-1,2,3-triazole-4-carboxamide, 1-[(3,4-Dichlorophenyl)methyl]-N-[3-(hydroxymethyl)phenyl]-5-methyl-1H-1,2,3-triazole-4-carboxamide, Methyl 3-[({1-[(3,4-dichlorophenyl)methyl]-5-methyl-1H-1,2,3-triazol-4-yl}carbonyl)amino]-4-(methyloxy)benzoate, 1-[(3,4-Dichlorophenyl)methyl]-N-[4-hydroxy-3-(hydroxymethyl)phenyl]-5-methyl-1H-1,2,3-triazole-4-carboxamide, Ethyl {4-[({1-[(3,4-dichlorophenyl)methyl]-5-methyl-1H-1,2,3-triazol-4-yl}carbonyl)amino]phenyl}acetate, Methyl 4-[({1-[(3,4-dichlorophenyl)methyl]-5-methyl-1H-1,2,3-triazol-4-yl}carbonyl)amino]-2-(methyloxy)benzoate, Methyl 5-[({1-[(3,4-dichlorophenyl)methyl]-5-methyl-1H-1,2,3-triazol-4-yl}carbonyl)amino]-2-hydroxybenzoate, Methyl {3-[({1-[(3,4-dichlorophenyl)methyl]-5-methyl-1H-1,2,3-triazol-4-yl}carbonyl)amino]phenyl}acetate, 1-[(3,4-Dichlorophenyl)methyl]-N-(3-hydroxyphenyl)-5-methyl-1H-1,2,3-triazole-4-carboxamide, Methyl 5-[({1-[(3,4-dichlorophenyl)methyl]-5-methyl-1H-1,2,3-triazol-4-yl}carbonyl)amino]-2-fluorobenzoate, N-[5-(Aminocarbonyl)-2-(methyloxy)phenyl]-1-[(3,4-dichlorophenyl)methyl]-5-methyl-1H-1,2,3-triazole-4-carboxamide, Methyl 4-chloro-3-[({1-[(3,4-dichlorophenyl)methyl]-5-methyl-1H-1,2,3-triazol-4-yl}carbonyl)amino]benzoate, Methyl [3-[({1-[(3,4-dichlorophenyl)methyl]-5-methyl-1H-1,2,3-triazol-4-yl}carbonyl)amino]-4-(methyloxy) phenyl]acetate,
Methyl 3-[({1-[(3,4-dichlorophenyl)methyl]-5-methyl-1H-1,2,3-triazol-4-yl}carbonyl)amino]-4-fluorobenzoate,
N-[3-(hydroxymethyl)phenyl]-5-methyl-1-(phenylmethyl)-1H-1,2,3-triazole-4-carboxamide,
N-[4-(hydroxymethyl)phenyl]-5-methyl-1-(phenylmethyl)-1H-1,2,3-triazole-4-carboxamide,
N-[3-(hydroxymethyl)-2-methylphenyl]-5-methyl-1-(phenylmethyl)-1H-1,2,3-triazole-4-carboxamide,
1-[(3,5-Dichlorophenyl)methyl]-N-[3-(hydroxymethyl)phenyl]-5-methyl-1H-1,2,3-triazole-4-carboxamide,
Methyl 3-[({1-[(3,5-dichlorophenyl)methyl]-5-methyl-1H-1,2,3-triazol-4-yl}carbonyl)amino]-4-(methyloxy)benzoate,
1-[(3,5-Dichlorophenyl)methyl]-N-[3-(hydroxymethyl)-2-methylphenyl]-5-methyl-1H-1,2,3-triazole-4-carboxamide,
N-{3-[(Acetylamino)methyl]phenyl}-1-[(3,4-dichlorophenyl)methyl]-5-methyl-1H-1,2,3-triazole-4-carboxamide,
1-[(3,4-Dichlorophenyl)methyl]-N-[3-(1-hydroxyethyl)phenyl]-5-methyl-1H-1,2,3-triazole-4-carboxamide,
N-[4-chloro-3-(hydroxymethyl)phenyl]-1-[(3,4-dichlorophenyl)methyl]-5-methyl-1H-1,2,3-triazole-4-carboxamide,
Dimethyl 4-[({1-[(3,4-dichlorophenyl)methyl]-5-methyl-1H-1,2,3-triazol-4-yl}carbonyl)amino]-1,2-benzenedicarboxylate,
Methyl 5-[({1-[(3,5-dichlorophenyl)methyl]-5-methyl-1H-1,2,3-triazol-4-yl}carbonyl)amino]-2-fluorobenzoate,
Ethyl 4-[({1-[(3,4-dichlorophenyl)methyl]-5-methyl-1H-1,2,3-triazol-4-yl}carbonyl)amino]benzoate,
1-[(3,4-Dichlorophenyl)methyl]-N-[4-(hydroxymethyl)-2-(methyloxy)phenyl]-5-methyl-1H-1,2,3-triazole-4-carboxamide,
1-[(3,4-Dichlorophenyl)methyl]-N-[4-(2-hydroxyethyl)phenyl]-5-methyl-1H-1,2,3-triazole-4-carboxamide,
1-[(3,4-Dichlorophenyl)methyl]-N-[5-(hydroxymethyl)-2-(methyloxy)phenyl]-5-methyl-1H-1,2,3-triazole-4-carboxamide,
N-[3,5-Bis(hydroxymethyl)phenyl]-1-[(3,4-dichlorophenyl)methyl]-5-methyl-1H-1,2,3-triazole-4-carboxamide,
1-[(3,4-Dichlorophenyl)methyl]-N-[4-fluoro-3-(hydroxymethyl)phenyl]-5-methyl-1H-1,2,3-triazole-4-carboxamide,
1-[(3,4-Dichlorophenyl)methyl]-N-[5-(2-hydroxyethyl)-2-(methyloxy)phenyl]-5-methyl-1H-1,2,3-triazole-4-carboxamide,
1-[(3,4-Dichlorophenyl)methyl]-N-[2-fluoro-5-(hydroxymethyl)phenyl]-5-methyl-1H-1,2,3-triazole-4-carboxamide,
N-[2-chloro-5-(hydroxymethyl)phenyl]-1-[(3,4-dichlorophenyl)methyl]-5-methyl-1H-1,2,3-triazole-4-carboxamide,
1-[(3,5-Dichlorophenyl)methyl]-N-[5-(hydroxymethyl)-2-(methyloxy)phenyl]-5-methyl-1H-1,2,3-triazole-4-carboxamide,
N-[3,4-Bis(hydroxymethyl)phenyl]-1-[(3,4-dichlorophenyl)methyl]-5-methyl-1H-1,2,3-triazole-4-carboxamide,
1-[(3,5-Dichlorophenyl)methyl]-N-[4-fluoro-3-(hydroxymethyl)phenyl]-5-methyl-1H-1,2,3-triazole-4-carboxamide,
N-[3,5-bis(hydroxymethyl)phenyl]-5-methyl-1-(phenylmethyl)-1H-1,2,3-triazole-4-carboxamide,
N-[3,5-bis(hydroxymethyl)phenyl]-1-[(3-chlorophenyl)methyl]-5-methyl-1H-1,2,3-triazole-4-carboxamide,
1-[(3,4-Dichlorophenyl)methyl]-N-[3-(2-hydroxyethyl)phenyl]-5-methyl-1H-1,2,3-triazole-4-carboxamide,
3-[({1-[(3,4-Dichlorophenyl)methyl]-5-methyl-1H-1,2,3-triazol-4-yl}carbonyl)amino]benzoic acid,
3-[({1-[(3,4-Dichlorophenyl)methyl]-5-methyl-1H-1,2,3-triazol-4-yl}carbonyl)amino]-4-(methyloxy)benzoic acid,
5-({[5-Methyl-1-(phenylmethyl)-1H-1,2,3-triazol-4-yl]carbonyl}amino)-1,3-benzenedicarboxylic acid,
4-[({1-[(3,4-Dichlorophenyl)methyl]-5-methyl-1H-1,2,3-triazol-4-yl}carbonyl)amino]benzoic acid,
1-[(3,4-Dichlorophenyl)methyl]-N-{3-[(ethylamino)carbonyl]phenyl}-5-methyl-1H-1,2,3-triazole-4-carboxamide,
1-[(3,4-Dichlorophenyl)methyl]-N-(3-{[(2-hydroxyethyl)amino]carbonyl}phenyl)-5-methyl-1H-1,2,3-triazole-4-carboxamide,
1-[(3,4-Dichlorophenyl)methyl]-5-methyl-N-[5-[(methylamino)carbonyl]-2-(methyloxy)phenyl]-1H-1,2,3-triazole-4-carboxamide,
{3-[({1-[(3,4-Dichlorophenyl)methyl]-5-methyl-1H-1,2,3-triazol-4-yl}carbonyl)amino]phenyl}methyl acetate,
{3-[({1-[(3,5-Dichlorophenyl)methyl]-5-methyl-1H-1,2,3-triazol-4-yl}carbonyl)amino]phenyl}methyl acetate,
{3-[({1-[(3,4-Dichlorophenyl)methyl]-5-methyl-1H-1,2,3-triazol-4-yl}carbonyl)amino]phenyl}methyl benzoate,
{3-[({1-[(3,5-Dichlorophenyl)methyl]-5-methyl-1H-1,2,3-triazol-4-yl}carbonyl)amino]phenyl}methyl benzoate,
1-[(3,4-Dichlorophenyl)methyl]-N-{4-[(2-hydroxyethyl)oxy]phenyl}-5-methyl-1H-1,2,3-triazole-4-carboxamide,
1-[(3,4-Dichlorophenyl)methyl]-5-methyl-N-[4-(1-methylethenyl)-2-(methyloxy)phenyl]-1H-1,2,3-triazole-4-carboxamide,
1-[(3,4-Dichlorophenyl)methyl]-N-[3-(1-hydroxy-1-methylethyl)phenyl]-5-methyl-1H-1,2,3-triazole-4-carboxamide,
1-[(3,4-Dichlorophenyl)methyl]-N-[4-{[2-(dimethylamino)ethyl]oxy}-3-(hydroxymethyl)phenyl]-5-methyl-1H-1,2,3-triazole-4-carboxamide,
1-[(3,4-Dichlorophenyl)methyl]-N-{3-[(2-hydroxyethyl)oxy]phenyl}-5-methyl-1H-1,2,3-triazole-4-carboxamide, and
{5-[({1-[(3,4-Dichlorophenyl)methyl]-5-methyl-1H-1,2,3-triazol-4-yl}methyl)amino]benzene-1,3-diyl}dimethanol,
or a pharmaceutically acceptable salt thereof.

6. The method according to claim 1 wherein the compound of Formula (I) is N-[3,5-bis(hydroxymethyl)phenyl]-1-[(3,4-dichlorophenyl)methyl]-5-methyl-1H-1,2,3-triazole-4-carboxamide or a pharmaceutically acceptable salt thereof.

7. The method according to claim 1 wherein the compound of Formula (I) is 1-[(3,4-Dichlorophenyl)methyl]-N-[4-(hydroxymethyl)phenyl]-5-methyl-1H-1,2,3-triazole-4-carboxamide, or a pharmaceutically acceptable salt thereof.

8. The method according to claim 1 wherein the disease or condition is selected from the group consisting of eczema, acne, psoriasis, skin ageing, keloid scar formation, and diseases related to production or secretions from mucous membranes.

9. The method according to claim 8 wherein the disease or condition is acne.

10. The method according to claim 1 wherein the compound of Formula (I) is N-[3,5-bis(hydroxymethyl)phenyl]-1-[(3,4-dichlorophenyl)methyl]-5-methyl-1H-1,2,3-triazole-4-carboxamide, or a pharmaceutically acceptable salt thereof, and wherein the disease or condition is selected from the group consisting of eczema, acne, psoriasis, skin ageing, keloid scar formation, and diseases related to production or secretions from mucous membranes.

11. The method according to claim 10 wherein the disease or condition is acne.

12. The method according to claim 1 wherein the disease or condition is selected from the group consisting of dyslipidemia, hypoalphalipoproteinemia, hyperbetalipoproteinemia, hypercholesterolemia, hypertriglyceridernia, or familial hypercholesterolemia.

13. The method according to claim 1 wherein the disease or condition is selected from the group consisting of obesity, Type I diabetes, Type II diabetes, vascular complications of diabetes, insulin resistance, hyperinsulinemia and metabolic syndrome.

14. The method according to claim 1 wherein the disease or condition is selected from the group consisting of peripheral vascular disease, reperfusion injury, angioplastic restenosis, and hypertension.

15. The method according to claim 1 wherein the disease or condition is caused by or associated with an abnormal plasma lipid profile.

16. A method according to claim 1 wherein the disease or condition is caused by or associated with an abnormal plasma lipid profile selected from the group consisting of dyslipidemia, hypoalphalipoproteinemia, hyperbetalipoproteinemia, hypercholesterolemia, hypertriglyceridemia, familial hypercholesterolemia, angina, ischemia, cardiac ischemia, stroke, myocardial infarction, atherosclerosis, obesity, Type I diabetes, Type II diabetes, insulin resistance, hyperinsulinemia and metabolic syndrome; peripheral vascular disease, reperfusion injury, angioplastic restenosis, hypertension, vascular complications of diabetes, thrombosis, hepatic steatosis, non-alcoholic steatohepatitis (NASH) and other diseases related to accumulation of lipids in the liver; eczema, acne, psoriasis, skin ageing, keloid scar formation or prevention, and diseases related to production or secretions from mucous membranes; cancer, neoplasia, malignancy, metastases, tumours (benign or malignant), carcinogenesis, hepatomas and the like; mild cognitive impairment (MCI), Alzheimer's Disease (AD), cerebral amyloid angiopathy (CAA) or dementia associated with Down Syndrome (DS) and other neurodegenerative diseases characterized by the formation or accumulation of amyloid plaques comprising Aβ42.

17. The method according to claim 1 wherein the compound of Formula (I) is 1-[(3,4-Dichlorophenyl)methyl]-N-[4-(hydroxymethyl)phenyl]-5-methyl-1H-1,2,3-triazole-4-carboxamide, or a pharmaceutically acceptable salt thereof, and wherein the disease or condition is selected from the group consisting of eczema, acne, psoriasis, skin ageing, keloid scar formation, and diseases related to production or secretions from mucous membranes.

18. The method according to claim 17 wherein the disease or condition is acne.

19. The method according to claim 7 wherein the disease or condition is selected from the group consisting of hepatic steatosis, non-alcoholic steatohepatitis (NASH) and other diseases related to accumulation of lipids in the liver.

20. The method according to claim 19 wherein the disease or condition is non-alcoholic steatohepatitis (NASH).

21. The method according to claim 1 wherein the compound of Formula (I) is N-[3,5-bis(hydroxymethyl)phenyl]-1-[(3,4-dichlorophenyl)methyl]-5-methyl-1H-1,2,3-triazole-4-carboxamide, or a pharmaceutically acceptable salt thereof, or 1-[(3,4-Dichlorophenyl)methyl]-N-[4-(hydroxymethyl)phenyl]-5-methyl-1H-1,2,3-triazole-4-carboxamide, or a pharmaceutically acceptable salt thereof and wherein the disease or condition is caused by or associated with an abnormal plasma lipid profile selected from the group consisting of dyslipidemia, hypoalphalipoproteinemia, hyperbetalipoproteinemia, hypercholesterolemia, hypertriglyceridemia, familial hypercholesterolemia, angina, ischemia, cardiac ischemia, stroke, myocardial infarction, atherosclerosis, obesity, Type I diabetes, Type II diabetes, insulin resistance, hyperinsulinaemia and metabolic syndrome; peripheral vascular disease, reperfusion injury, angioplastic restenosis, hypertension, vascular complications of diabetes, thrombosis, hepatic steatosis, non-alcoholic steatohepatitis (NASH) and other diseases related to accumulation of lipids in the liver; eczema, acne, psoriasis, skin ageing, keloid scar formation or prevention, and diseases related to production or secretions from mucous membranes; cancer, neoplasia, malignancy, metastases, tumours (benign or malignant), carcinogenesis, hepatomas and the like; mild cognitive impairment (MCI), Alzheimer's Disease (AD), cerebral amyloid angiopathy (CAA) or dementia associated with Down Syndrome (DS) and other neurodegenerative diseases characterized by the formation or accumulation of amyloid plaques comprising Aβ42.

* * * * *